US008562985B2

(12) United States Patent
Michaud et al.

(10) Patent No.: US 8,562,985 B2

(45) **Date of Patent: *Oct. 22, 2013**

(54) ANTIBODIES TO C-MET

(75) Inventors: Neil R. Michaud, Pawcatuck, CT (US); Shama Kajiji, Mystic, CT (US); Gary Borzillo, Old Lyme, CT (US); Vahe Bedian, East Lyme, CT (US); Kevin Coleman, Old Lyme, CT (US); Larry L. Green, San Francisco, CA (US); Xiao-Chi Jia, Los Angeles, CA (US)

(73) Assignees: Amgen Fremont Inc., Thousand Oaks, CA (US); Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,356

(22) Filed: Apr. 24, 2012

(65) Prior Publication Data

US 2012/0321614 A1 Dec. 20, 2012

Related U.S. Application Data

(60) Continuation of application No. 12/321,963, filed on Jan. 26, 2009, now Pat. No. 8,163,280, which is a division of application No. 10/910,901, filed on Aug. 3, 2004, now Pat. No. 7,498,420.

(60) Provisional application No. 60/492,432, filed on Aug. 4, 2003.

(51) Int. Cl.
*A61K 39/395* (2006.01)

(52) U.S. Cl.
USPC .................................... 424/130.1; 530/387.1

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,405,712 | A | 9/1983 | Vande Woude et al. |
| 4,510,245 | A | 4/1985 | Cousens et al. |
| 4,634,665 | A | 1/1987 | Axel et al. |
| 4,740,461 | A | 4/1988 | Kaufinan |
| 4,912,040 | A | 3/1990 | Kaufman et al. |
| 4,959,455 | A | 9/1990 | Clark et al. |
| 4,968,615 | A | 11/1990 | Koszinowski et al. |
| 5,151,510 | A | 9/1992 | Stec et al. |
| 5,168,062 | A | 12/1992 | Stinski |
| 5,179,017 | A | 1/1993 | Axel et al. |
| 5,223,409 | A | 6/1993 | Ladner et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,587,458 | A | 12/1996 | King et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,633,425 | A | 5/1997 | Lonberg et al. |
| 5,643,763 | A | 7/1997 | Dunn et al. |
| 5,646,036 | A | 7/1997 | Schwall et al. |
| 5,661,016 | A | 8/1997 | Lonberg et al. |
| 5,686,292 | A | 11/1997 | Schwall et al. |
| 5,693,767 | A | 12/1997 | Klemke et al. |
| 5,721,367 | A | 2/1998 | Kay et al. |
| 5,741,957 | A | 4/1998 | Deboer et al. |
| 5,747,498 | A | 5/1998 | Schnur et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,792,783 | A | 8/1998 | Tang et al. |
| 5,814,318 | A | 9/1998 | Lonberg et al. |
| 5,827,690 | A | 10/1998 | Meade et al. |
| 5,834,504 | A | 11/1998 | Tang et al. |
| 5,861,510 | A | 1/1999 | Piscopio et al. |
| 5,863,949 | A | 1/1999 | Robinson et al. |
| 5,877,305 | A | 3/1999 | Huston et al. |

(Continued)

FOREIGN PATENT DOCUMENTS

| | | |
|---|---|---|
| EP | 0216846 | 4/1987 |
| EP | 0256055 | 2/1988 |

(Continued)

OTHER PUBLICATIONS

Altschul et al., "Basic local alignment search tool," *Journal of Molecular Biology*, 215(1):403-410 (1990).

(Continued)

*Primary Examiner* — Laura B Goddard
*Assistant Examiner* — Meera Natarajan
(74) *Attorney, Agent, or Firm* — Scott Ausenhus

(57) ABSTRACT

The present invention relates to antibodies including human antibodies and antigen-binding portions thereof that specifically bind to c-Met, preferably human c-Met, and that function to inhibit c-Met. The invention also relates to human anti-c-Met antibodies and antigen-binding portions thereof. The invention also relates to antibodies that are chimeric, bispecific, derivatized, single chain antibodies or portions of fusion proteins. The invention also relates to isolated heavy and light chain immunoglobulins derived from human anti-c-Met antibodies and nucleic acid molecules encoding such immunoglobulins. The present invention also relates to methods of making human anti-c-Met antibodies, compositions comprising these antibodies and methods of using the antibodies and compositions for diagnosis and treatment. The invention also provides gene therapy methods using nucleic acid molecules encoding the heavy and/or light immunoglobulin molecules that comprise the human anti-c-Met antibodies. The invention also relates to transgenic animals or plants comprising nucleic acid molecules of the present invention.

21 Claims, 21 Drawing Sheets

(56) References Cited

U.S. PATENT DOCUMENTS

| | | | | |
|---|---|---|---|---|
| 5,883,113 | A | 3/1999 | Tang et al. | |
| 5,886,020 | A | 3/1999 | Tang et al. | |
| 5,916,771 | A | 6/1999 | Hori et al. | |
| 5,939,598 | A | 8/1999 | Kucherlapati et al. | |
| 5,959,177 | A | 9/1999 | Hein et al. | |
| 5,985,615 | A | 11/1999 | Jakobovits et al. | |
| 5,994,619 | A | 11/1999 | Stice et al. | |
| 5,998,209 | A | 12/1999 | Jokobovits et al. | |
| 6,046,037 | A | 4/2000 | Hiatt et al. | |
| 6,075,181 | A | 6/2000 | Kucherlapati et al. | |
| 6,091,001 | A | 7/2000 | Jakobovits et al. | |
| 6,099,841 | A | 8/2000 | Hillan et al. | |
| 6,114,598 | A | 9/2000 | Kucherlapati et al. | |
| 6,130,364 | A | 10/2000 | Jakobovits et al. | |
| 6,150,584 | A | 11/2000 | Kucherlapati et al. | |
| 6,162,963 | A | 12/2000 | Kucherlapati et al. | |
| 6,207,152 | B1 | 3/2001 | Schwall et al. | |
| 6,214,344 | B1 | 4/2001 | Schwall et al. | |
| 6,284,764 | B1 | 9/2001 | Kath et al. | |
| 6,300,064 | B1 | 10/2001 | Knappik et al. | |
| 6,417,429 | B1 | 7/2002 | Hein et al. | |
| 6,465,449 | B1 | 10/2002 | Kath et al. | |
| 6,468,529 | B1 | 10/2002 | Schwall et al. | |
| 6,517,529 | B1 | 2/2003 | Quinn et al. | |
| 6,682,736 | B1 | 1/2004 | Hanson et al. | |
| 6,803,039 | B2 | 10/2004 | Tsuji et al. | |
| 2002/0136721 | A1 | 9/2002 | Schwall et al. | |
| 2003/0124671 | A1 | 7/2003 | Chan et al. | |
| 2003/0211100 | A1 | 11/2003 | Bedian et al. | |
| 2004/0086503 | A1 | 5/2004 | Cohen et al. | |
| 2004/0166544 | A1* | 8/2004 | Morton et al. | 435/7.23 |

FOREIGN PATENT DOCUMENTS

| | | |
|---|---|---|
| EP | 0323997 | 7/1989 |
| EP | 0338841 | 10/1989 |
| EP | 0606046 | 7/1994 |
| EP | 0780386 | 6/1997 |
| EP | 0805203 | 11/1997 |
| EP | 0818442 | 1/1998 |
| EP | 0931788 | 7/1999 |
| EP | 0945864 | 9/1999 |
| EP | 1004578 | 5/2001 |
| WO | WO 90/05719 | 5/1990 |
| WO | WO 91/10741 | 7/1991 |
| WO | WO 91/17271 | 11/1991 |
| WO | WO 92/01047 | 1/1992 |
| WO | WO 92/09690 | 6/1992 |
| WO | WO 92/13097 | 8/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 93/06213 | 4/1993 |
| WO | WO 94/02602 | 2/1994 |
| WO | WO 95119970 | 7/1995 |
| WO | WO 95/21613 | 8/1995 |
| WO | WO 96/27583 | 9/1996 |
| WO | WO 96/33172 | 10/1996 |
| WO | WO 96/33735 | 10/1996 |
| WO | WO 96/34096 | 10/1996 |
| WO | WO 96/38557 | 12/1996 |
| WO | WO 97/13760 | 4/1997 |
| WO | WO 97/22596 | 6/1997 |
| WO | WO 97/32856 | 9/1997 |
| WO | WO 98/00543 | 1/1998 |
| WO | WO 98/02434 | 1/1998 |
| WO | WO 98/02437 | 1/1998 |
| WO | WO 98/02438 | 1/1998 |
| WO | WO 98/03516 | 1/1998 |
| WO | WO 98/07697 | 2/1998 |
| WO | WO 98/14451 | 4/1998 |
| WO | WO 98/16654 | 4/1998 |
| WO | WO 98/24893 | 6/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 98/50356 | 11/1998 |
| WO | WO 98/50433 | 11/1998 |
| WO | WO 98/52976 | 11/1998 |
| WO | WO 98/54093 | 12/1998 |
| WO | WO 99/10349 | 3/1999 |
| WO | WO 99/16755 | 4/1999 |
| WO | WO 99/24440 | 5/1999 |
| WO | WO 99/29667 | 6/1999 |
| WO | WO 99/35132 | 7/1999 |
| WO | WO 99/35146 | 7/1999 |
| WO | WO 99/45031 | 9/1999 |
| WO | WO 99/52889 | 10/1999 |
| WO | WO 99/52910 | 10/1999 |
| WO | WO 99/53049 | 10/1999 |
| WO | WO 99/61422 | 12/1999 |
| WO | WO 99/62890 | 12/1999 |
| WO | WO 00/09560 | 2/2000 |
| WO | WO 00/34317 | 6/2000 |
| WO | WO 00/37504 | 6/2000 |
| WO | WO 01/34650 | 5/2001 |
| WO | WO 02/053596 | 7/2002 |
| WO | WO 03/040170 | 5/2003 |
| WO | WO 03/048731 | 6/2003 |
| WO | WO 2004/072117 | 8/2004 |
| WO | WO 2004/078778 | 9/2004 |
| WO | WO 2005/016382 | 2/2005 |
| WO | WO 2005/017107 | 2/2005 |

OTHER PUBLICATIONS

Altschul et al., "Gapped BLAST and PSI-BLAST: a new generation of protein database search programs," *Nucleic Acids Research*, 25(17):3389-3402 (1997).

Amicone et al., "Transgenic expression in the live of truncated Met blocks apoptosis and permits immortalization ofhepatoeytes," *The EMBO Journal*, 16(3):495-503 (1997).

Babcook et al., "A novel strategy for generating monoclonal antibodies from single, isolated lymphocytes producing antibodies of defined specificities," *PNAS*, 93:7843-7848 (1996).

Barbas et al., "Assembly of combinatorial antibody libraries on phage surfaces: the gene III site," *PNAS*, 88:7978-7982 (1991).

Bendig, "Humanization of rodent monoclonal antibodies by CDR Grafting," *Methods: A Companion to Methods in Enzymology*, 8:83-93 (1995).

Beviglia et al., "Expression of the c-Met1HGF receptor in human breast carcinoma: Correlation with tumor progression," *Int. J. Cancer*, 74:301-309 (1997).

Birchmeier et al., "Met, metastasis, motility and more," *National Reviews Molecular Cell Biology*, 4:915-925 (2003).

Bird et al., "Single-chain antigen bindin proteins," *Science*, 242:423-426 (1988).

Bose et al., "Problems in using statistical analysis of replacement and silent mutations in antibody genes for determining antigen-driven affinity selection," *Immunology*, 116:172-183 (2005).

Bowie et al., "A method to identify protein sequences that fold into a known three-dimensional structure," *Science*, 253. 164-170 (1991).

Bussolino et al., "Hepatocyte growth factor is a potent angiogenic factor which stimulates endothelial cell motility and growth," *The Journal of Cell Biology*, 119(3):629-641 (1992).

Cao et al., "Neutralizing monoclonal antibodies to hepatocyte growth factor/scatter factor (HGF/SF) display antitumor activity in animal models," *Proceedings of the NationalAcademy a/Sciences of the United States of America*, 98(13):7443-7448 (2001).

Casset et al. Biochemical and Biophysical Research Communications, 307:198-205, 2003.

Chan et al., "Identification of a competitive HGF antagonist encoded by an alternative transcript," *Science*, 254:1382-1385 (1991).

Chothia et al., "Canonical structures for the hypervariable regions of immunoglobulins," *Journal of Molecular Biology*, 196:901-917 (1987).

(56) References Cited

OTHER PUBLICATIONS

Chothia et al "Conformations of immunoglobulin hypervariable regions," *Nature*, 342:877-883 (1989).
Christensen et al., "A selective small molecule inhibitor of c-Met kinase inhibits c-Metdependent phenotypes in vitro and exhibits cytoreductive antitumor activity in vivo, "*Cancer Research*, 63:7345-7355 (2003).
Clackson et al., "Making antibody fragments using phage display libraries," *Nature*, 352:624-628 (1991).
Colman, "Effects of amino acid sequence changes on antibody-antigen interactions," *Research in Immunology*, 145:33-36 (1994).
Corps et al., "Hepatocyte growth factor stimulates motility, chemotaxis and mitogenesis in ovarian carcinoma cells expression high levels of c-MET," *Int J. Cancer*, 73:151-155 (1997).
Date et al., "HGFINK4 is a specific antagonist for pielotrophic actions hepatocyte growth factor," *FEBS Letters*, 420: 1-6 (1997).
David et al., "A study of the structural correlates of affinity maturation: antibody affinity as a function of chemical interactions, structural plasticity and stability," *Molecular Immunology*, 44: 1342-1351 (2007).
Ebert et al., "Coexpression of the *c-met* proto-oncogene and hepatocyte growth factor in human pancreatic cancer," *Cancer Research*, 54:5775-5778 (1994).
Evans et al., "Design of non pep tidal ligands for a peptide receptor: Cholecystokinin antagonists," *Journal of Medicinal Chemistry*, 30: 1229-1239 (1987).
Fauchere, "Elements for the rational drug design of pep tides drugs," *Advances in Drug Research*, 15:29-69 (1986).
Fishwild et al., "High-avidityhuman IgG kappa monoclonal antibodies from a novel strain of mini locus transgenic mice," *Nature Blotecnnology*, 14:845-851 (1996).
Fuchs et al., "Targeting recombinant antibodies to the surface of *Escherichia coli*: fusion to a peptidoglycan associated lipoprotein," *Biotechnology*, 9: 1369-1372 (1991).
Galfre et al., "Preparation of monoclonal antibodies: strategies and procedures," *Methods in Enzyinology*, 73:3-46 (1981).
Garrard et al., "F AB assembly and enrichment in a monovalent phage display system," *Biotechnology*, 9:1373-1377 (1991).
Gonnet et al., "Exhaustive matching of the entire protein sequence database," *Science*, 256:1443-1445 (1992).
Gram et al., "In vitro selection and affinity maturation of antibodies from a naive combinatorial immunoglobulin library," *PNAS*, 89:3576-3580 (1992).
Green et al., "Regulation of B cell development by variable gene complexity in mice reconstituted with human immunoglobulin yeast artificial chromosomes," *Journal of Experimental Medicine*, 188(3):483-495 (1998).
Green et al., "Antigen-specific human monoclonal antibodies from mice engineered with human 19 heavy and light chain Y ACs," *Nature Genetics*, 7: 13-21 (1994).
Green, "Antibody engineering via genetic engineering of the mouse: Xenomouse stra1ns are a vehicle for the facile generation of therapeutic human monoclonal antibodies," *Journal of Immunological Methods*, 231: 11-23 (1999).
Griffiths et al., "Human anti-self antibodies with high specificity from phage display libraries," *The EMBO Journal*, 12(2):725-734 (1993).
Griffiths et al., "Isolation of high aftiinity human antibodies directly from large synthetic repertoires," *The EMBO Journal*, 13(14):3245-3260 (1994).
Harvey et al., "Immunoreactivity for hepatocyte growth factor/scatter factor and its receptor, met, in human lung carcinomas and malignant mesotheliomas," *Journal of Pathology*, 180:389-394 (1996).
Hawkins et al., "Selection of phage antibodies by binding itfmity mimicking affinity maturation," *Journal of Molecular Biology*, 226:889-896 (1992).
Hay et al., "Bacteriophage cloning and *Escherichia coli* expression of a human IgM Fab," *Hum. Antibod Hybridomas*, 3:81-85 (1992).
Hiscox et al., "Expression of the HGF/SF receptor/ *c-met*, and its ligand in human color ectal cancers," *Cancer Investigation*, 15(6):513-521 (1997).
Holliger et al., "Diabodies; small bivalent and bispecific antibody fragments," *PNAS*, 90:6444-6448 (1993).
Hoogenboom et al., "Multi-subunit proteins on the surface of filamentous phage: methodologies for displaying antibody (Fab) heavy and light cha1ns," *Nucleic Acids Research*, 19(15):4133-4137 (1991).
Huse et al., "Generation of a large combinatorial library of the immunoglobulin repertoire in phage lambda," *Science*, 246:1275-1281 (1989).
Huston et al., "Protein engineering of antibody binding sites: recovery of specific activity in an anti-digoxin single-cha1n Fv analogue produced in *Escherichia coli," PNAS*, 85:5879-5883 (1988).
Ibragimova et al., "Stability of the beta-sheet of the WW domain: A molecular dynamic simulation study," *Biophysical Journal*, 77:2192-2198 (1999).
III et al., "Design and construction of a hybrid immunoglobulin domaln with properties of both heavy and light chain variable regions," *Protein Engineering*, 10(8): 949-957 (1997).
Jeffers et al., "Activating mutations for the Met tyrosine kinase receptor in human cancer," *PNAS*, 94: 11445-11450 (1997).
Jeffers et al., "Hepatocyte growth factor/scatter factor-Met signaling in tumorigenicity and invasion/metastasis," *J. Mol. Med*, 74:505-513 (1996).
Johnsson et al., "Comparison of methods for immobilization to carboxymethyl dextran sensor surfaces by analysis of the specific activity of monoclonal antibodies," *Journal of Molecular Recognition*, 8: 125-131 (1995).
Johnsson et al., "Immobolization of proteins to a carboxymethyldextranmoditied gold surface for biospecific interaction analysis in surface Plasmon resonance sensors," *Analytical Biochemistry*, 198:268-277 (1991).
Jonsson et al., "Introducing a biosensor based technology for real-time biospecific interaction analysis," *Ann. Biologie Clinique.*, 51:19-26 (1993).
Jonsson et al., "Real-time biospecific interaction analysis using surface plasmon resonance and a sensor chip technology," *BioTechniques*, 11(5):620-627 (1991).
Kaji et al, "Participation of *c-met* in the progression of human gastric cancers: *Anti-c-met* oligonucleotides inhibit proliferation or invasiveness of gastric cancer cells," *Cancer Gene Therapy*, 3(6):393-404 (1996).
Kan et al., "Hepatocyte growth factorihepatopoietin a stimulates the growth of rat kidney proximal tubule epithelial cells (RPTE), rat nonparenchymalliver cells, human melanoma cells, mouse keratinocytes, and stimulates anchorageindpendent growth of SV-40 transformed RPTE," *Biochemical and Biophysical Research Communications*, 174(1):331-337 (1991).
Klominek et al., "Hepatocyte growth factor/scatter factor simulates chemotaxis and growth of malignant mesothelioma cells through c-met receptor," *Int. J. Cancer*, 76:240-249 (1998).
Kong-Beltran et al., "The Serna domain of Met is necessary for receptor dimerization and activation", *Cancer Cell*, 6:75-84 (2004).
Koochekpour et al., "Met and hepatocyte growth factor/scatter factor expression in human gliomas," *Cancer Research*, 57:5391-5398 (1997).
Kostelny et al., "Formation of a hispecific antibody by the use of leucine zippers," The Journal ofImmunology 148:1547-1553 (1992).
Ladner et al., "Phage display-derived peptides as therapeutic alternatives to antibodies," *Drug Discovery Today*, 9(12):525-529 (2004).
LaPlanche et al., "Phosphorothiolate-modified oligodeoxyribonucleotides, III. NMR and UV spectroscopic studies of the Rp-Rp, Sp-Sp, and Rp-Sp duplexes, [d(GGsAATTCc)h, derived from diastereomeric O-ethyl phosphorothioates," *Nucleic Acids Research*, 14(22):9081-9093 (1986).
Lewin et al, Genes IV , Oxford University Press, p. 810, 1990.
Li et al., "Hepatocyte growth factor stimulates the invasion of gallbladder carcinoma cell ines in vitro," *Clin. Exp. Metastasis*, 16:74-82 (1998).

(56) References Cited

OTHER PUBLICATIONS

Ma et al., "A selective small molecule c-MET inhibitor. PHA665752, cooperates with rapamycin," *Clinical Cancer Research*, 11 (6):2312-2319 (2005).
MacCallum et al., "Antibody-antigen interactions: contact analysis and binding site topography:" *Journal of Molecular Biology*, 262:732-745 (1996).
Maggiora et al., "Control of invasive growth by the HGF receptor family," *Journal of Cellular Physiology*, 173: 183-186 (1997).
Maina et al., "Uncoupling of Grb2 from the Met receptor in vivo reveals complex roles in muscle development," *Celll*, 87:531-542 (1996).
Marks et al., "Oligonucleotide primers for polymerase cha1n reaction amplification of human immunoglobulin variable genes and design of family-specific oligonucleotide probes." *European Journal of Immunology*, 21:985-991 (1991).
Marshall of al., "Overexpression of scatter factor and its receptor (c-met) in oral scutamous cell carcinoma," *The Laryngoscope*, 108: 1413-1417 (1998).
Martin et al., "The affinity-selection of a minibody polypeptide inhibitor of human interleukin-6," *The EMBO Journal*, 13(22): 5303-5309 (1994).
Matsumoto et al., "Hepatocyte growth factor (HGF) as a tissue organizer for organogenesis and regeneration," *Biochemical and Biophysical Research Communications*, 239:639-644 (1997).
Matsumoto et al., "NK4 (HGF-antagonistlangiogenesis inhibitor) in cancer biology and therapeutics," *Cancer Science*9441:321-327 (2003).
McCafferty et al., "Phage antibodies: filamentous phage displaying antibody variable domains," *Nature*, 348:552-554 (1990).
Mendez et al., "Functional transplant of mega base human immunoglobulin loci recapitulates human antibody response in mice," *Nature Genetics*, 15: 146-156 (1997).
Morton et al., "In vitro and in vivo activity of fully-human monoclonal antibodies to c-Met protein tyrosine kinase," *Proceedings of the American Associationfor Cancer Research*, 44:1116 (2003).
Nagy et al., "Expression and loss of heterozygosity of c-met proto-oncogene in primarybeasat cancer," *Journal of Surgical Oncology*, 60(2):95-99 (1995).
Nagy et al., Hepatocyte growth factor/scatter factor expression and *c-met* in primary breast cancer, *Surgical Oncology*5:15-21 (1996).
Natali et al., "Expression of the met/HGF receptor in renal cell carcinomas," *Int. J. Cancer*, 69:212-217 (1996).
Nissim et al., "Antibody fragments from a 'single pot' phage display library as immunochemical reagents," *The EMBO Journal*, 13(3):692-698 (1994).
Paul, William E. , *Fundamental Immunology*, 3rd Edition, Raven Press, pp. 292-295 (1993).
Pearson, "Effective protein sequence comparison," *Methods in Enzymology*, 266:227-258 (1996).
Pearson, "Empirical statistical estimates for sequence simiarity, searches," *Journal of Molecular Biology*, 276:71-84 (1998).
Pearson, "Flexible sequence similarity searching with the FASTA3 program package," *Methods in Molecular Biology*, 132:185-219 (2000).
Pearson, "Rapid and sensitive sequence comparison with FASTP and FASTA," *Methods in Enzymolology*, 183:63-98 (1990).
Pearson, "Using the F ASTA program to search protein and DNA sequence databases," *Methods in Molecular Biology*, 24:307-331 (1994).
Poljak, "Production and structure of diabodies," *Structure*, 2: 1121-1123 (1994).
Pollack et al., "Inhibition of epidermal growth factor receptor-associated tyrosine phosphorylation in human carcinomas with CP-358,774: Dynamics of receptor inhibition in situ and antitumor effects in athymie mice," *Journal of Pharmacology and Experimental Therapeutics*, 291 :739-748 (1999).
Ponzetto et al., A multifunctional docking site mediates signaling and transformation by the hepatocyte growth factor/scatter factor receptor family, *Cell*, 77:261-271 (1994).
Riechmann et al., "Reshaping human antibodies for therapy," *Nature* 332(6162):323-327 (1988).
Rizo et al., "Constralned peptides: models ofbioactive peptides and protein substructures," *Annual Review of Biochemistry*, 61: 3 87-418 (1992).
Roeffen et al., "Recombinant human antibodies specific for the Pfs48/45 protein of the malaria parasite *Plasmodium falciparum," The Journal of Biological Chemistry*, 276(23):19807-19811 (2001).
Rong et al. "Tumorigenicity of the *met* proto-oncogene and the gene for hepatocyte growth factor," *Molecular Cell Biology*, 12(11):5152-5158 (1992).
Rubin et al., "A broad-spectrum human lung fibroblast-derived mitogen is a variant of hepatocyte growth factor," *PNAS*, 88:514-419 (1991).
Rudikoff et al., "Single amino acid substitution altering antigen-binding specificity," *PNAS*, 79(6):1979-1983 (1982).
Sattler et al., "Therapeutic targeting of the receptor tyrosine kinase Met," *Cancer Treatment Research*, 119:121-138 (2004).
Sattler et al., "A novel small molecule Met inhibitor induces apoptosis in cells transformed by the oncogenic TPR-MET tyrosine kinase," *Cancer Research*, 63(17):5462-5469 (2003).
Saucier et al., "The Shc adaptor protein is critical for VEGF induction by MetIHGF and ErbB2 receptors and for early onset of tumor angiogenesis," *Proceedings of the National Academy of Sciences of the United States of America*, 101(8):2345-2350 (2004).
Schmidt et al., :Germline and somatic mutations in the tyrosine kinase domaln of the *MET* proto-oncogene in papillary renal carcinomas, *Nature Genetics*, 16:68-73 (1997).
Skolnick et al., "From genes to protein structure and function: novel applications of computational approaches in the genomic era," *Trends in Biotechnology*, 18(1 ):34-39 (2000).
Songsivilal et al, "Bispecific antibody: a tool for diagnosis and treatment of disease," *Clinical and Experimental Immunology*, 79: 315-321 (1990).
Stec et al., "Automated solid-phase synthesis, separation, and stereochemistry of phosphorothioate analogues of oligodeoxyribonucleotides," *Journal of the American Chemical Society*, 106(20):6077-6079 (1984).
Stein et al., "Physiochemical properties ofphosphorothioate oligodeoxynucleotides," *Nucleic Acids Research*, 16(8):3209-3221 (1988).
Suzuki et al. "Expression of the *c-met* protooncogene in human hepatocellular carcinoma," *Hepatology*, 20(5): 1231-1236 (1994).
Taniguchi et al., "The relation between the growth patterns of gastric carcinoma and the expression of hepatocyte growth factor receptor (*c-met*), autocrine motility factor receptor, and urokinase-typre plasminogen activator receptor," *Cancer*, 82(11):2112-2122 (1998).
Thornton et al., "Prediction of progress at last," *Nature*, 354(14): 105-106 (1991).
Tolnay et al., "Hepatocyte growth factor/scatter and its receptor c-met are overexpressed and associated with an increased microvessel density in malignant pleural mesothelioma,", 124:291-296 (1998).
Traunecker et al., "Bispecific single chain molecules (Janusins) target cytotoxic lymphocytes on HIV infected cells," *The EMBO Journal*, 10(12):3655-3659 (1991).
Traunecker et al., "Janusin: new molecular design for bispecific reagents," *International Journal of Cancer*, 7:51-52 (1992).
Trusolino et al., "Scatter-factor and semaphorin receptors: cell signalling for invasive growth," *Nature Reviews Cancer*, 2:289-300 (2002).
Tuck et al., "Coexpression of hepatocyte growth factor and receptor (met) in human breast carcinonia," *American Journal of Pathology*, 148(1):225-232 (1996).
Uhlmann et al., "Antisense oligonucleotides: a new therapeutic principle," *Chemical Reviews*, 90(4):543-584 (1990).
Veber et al., "The design of metabolically-stable peptide analogs," *TINS*, 8(9):392-396 (1985).
Ward et al., "Binding activities of a repertoire of single immunoglobulin variable domalns secreted from *Escherichia coil," Nature*, 341 :544-546 (1989).

(56) References Cited

OTHER PUBLICATIONS

Weins et al., "Harmful somatic mutations: lessons from the dark side.," *Immunological Reviews* 162: 197-209 (1998).
Zbar et al., "Hereditaty papillary renal cell carcinoma," *The Journal of Urology*, 151:561-566 (1994).
Zon et al., "Phosphorothioate oligonucleotides," *Oligonucleotides and Analogues: A Practical Approach*, 87-108 (F. Eckstein, Ed., Oxford University Press, Oxford England (1991).
Zon et al., "Phosphorothioate oligonucleotides: chemistry, purification, analysis, scale-up and future directions," *Anti-Cancer Drug Design*, 6:539-568 (1991).

* cited by examiner

FIG. 3A

Germline V=L5, J=JK4

91

13.3.2 MDMRVPAQLLGLLLLWFPGSRCDIQMTQSPSSVSASVGDRVTITCRASQGINTWLAWYQQKPGKAPKLLIYAASSLKSGVPSRFSGSGSGADFTLTISSLQPEDFATYYCQQANSFPLTFGGGTKVEIK 13.3.2 A91T MDMRVPAQLLGLLLLWFPGSRCDIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIK

Germ MDMRVPAQLLGLLLLWFPGSRCDIQMTQSPSSVSASVGDRVTITCRASQGISSWLAWYQQKPGKAPKLLIYAASSLQSGVPSRFSGSGSGTDFTLTISSLQPEDFATYYCQQANSFPLTFGGGTKVEIK Signal peptide CDR1 CDR2 CDR3

FIG. 3B

Germline V=A27, J=JK2

9.1.2 METPAQLLFLLLLWLPDTTGEIVLTQSPGTLSLSPGERATLSCRASQSVSNNYLAWYQQKPGQAPRLLIFGASSRATGIPDRFSGSGSGTDFTLTISRLEPEDFAVYYCQQYDISPMYSFGQGTKLEMK

Germ METPAQLLFLLLLWLPDTTGEIVLTQSPGTLSLSPGERATLSCRASQSVSSSYLAWYQQKPGQAPRLLIYGASSRATGIPDRFSGSGSGTDFTLTISRLEPEDFAVYYCQQYGSSP-YTFGQGTKLEIK Signal peptide CDR1 CDR2 CDR3

FIG. 3C

Germline V=L5, J=JK3

8.70.2 MDMRVPAQLLGLLLLWFPGSRCDIQMTQSPSSVSASVGDRVTITCRASQGISSWLAWYQQKPGKAPKLLIYAASSLQSGVPSRFSGSGSGTDFTLTISSLQSEDFATYYCQQANSFPITFGPGTKVEIK

Germ MDMRVPAQLLGLLLLWFPGSRCDIQMTQSPSSVSASVGDRVTITCRASQGISSWLAWYQQKPGKAPKLLIYAASSLQSGVPSRFSGSGSGTDFTLTISSLQPEDFATYYCQQANSFPFTFGPGTKVDIK Signal peptide CDR1 CDR2 CDR3

FIG. 3D

Germline V=L5, J=JK1

8.90.3 MDMRVPAQLLGLLLLWFPGSRCDIQMTQSPSSVSASVGDRVIITCRASQGISSWLAWYQQKPGKAPKLLIYAASSLKSGVPSRFSGSGSGTDFTVTISSLQPEDFATYYCQQSNSLPWTFGQGTKVEIK

Germ MDMRVPAQLLGLLLLWFPGSRCDIQMTQSPSSVSASVGDRVTITCRASQGISSWLAWYQQKPGKAPKLLIYAASSLQSGVPSRFSGSGSGTDFTLTISSLQPEDFATYYCQQANSFPWTFGQGTKVEIK Signal peptide CDR1 CDR2 CDR3

FIG. 3E

Germline V=1-18, D=D2-15, J=JH4b 13.3.2 MDWTWSILFLVAAATGAHSQVQLVQSGAEVKKPGASVKVSCEASGYTFTSYGFSWVRQAPGQGLEWMGWISASNGNTYYAQKLQGRVTMTTDTSTSSAYMELRSLRSDDTAVYYCARVYADYADYWGQGTLVTVSS 13.3.2 E42K MDWTWSILFLVAAATGAHSQVQLVQSGAEVKKPGASVKVSCKASGYTFTSYGFSWVRQAPGQGLEWMGWISASNGNTYYAQKLQGRVTMTTDTSTSSAYMELRSLRSDDTAVYYCARVYADYADYWGQGTLVTVSS 13.3.2 E42K,S97T MDWTWSILFLVAAATGAHSQVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS 13.3.2 A14P MDWTWSILFLVAAPTGAHSQVQLVQSGAEVKKPGASVKVSCEASGYTFTSYGFSWVRQAPGQGLEWMGWISASNGNTYYAQKLQGRVTMTTDTSTSSAYMELRSLRSDDTAVYYCARVYADYADYWGQGTLVTVSS 13.3.2 A14P, E42K MDWTWSILFLVAAPTGAHSQVQLVQSGAEVKKPGASVKVSCKASGYTFTSYGFSWVRQAPGQGLEWMGWISASNGNTYYAQKLQGRVTMTTDTSTSSAYMELRSLRSDDTAVYYCARVYADYADYWGQGTLVTVSS 13.3.2 A14P, E42K,S97T MDWTWSILFLVAAPTGAHSQVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS Germ MDWTWSILFLVAAPTGAHSQVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR-YS-YFDYWGQGTLVTVSS Signal peptide CDR1 CDR2 CDR3

FIG. 3F

Germline V=4-31, D=D2-2+D7-27, J=JH6b 9.1.2 MKHLWFFLLLVAAPRWVLSQVQLQESGPGLVKPSQTLSLTCTVSGGSISSGGYYWSWIRQHPGKGLEWIGYIYYSGSTYYNPSLKSRVTISVDTSKNQFSLKLSSVTAADTAVYYCARDGPLGYCSSTSCPVTGE-YYYYGMDVWGQGTTVTVSS Germ MKHLWFFLLLVAAPRWVLSQVQLQESGPGLVKPSQTLSLTCTVSGGSISSGGYYWSWIRQHPGKGLEWIGYIYYSGSTYYNPSLKSRVTISVDTSKNQFSLKLSSVTAADTAVYYCAR----GYCSSTSC -TGDYYYYYGMDVWGQGTTVTVSS Signal peptide CDR1 CDR2 CDR3

FIG. 3G

Germline V=4-39, D=D2-2, J=JH4b 8.70.2 MKHLWFFLLLVAAPRWVLSQLQLQESGPGLVKPSETLSLTCTVSGGSISSSSYYGGWIRQPPGKGLDWIGSIYYSGNTYYNPSLKSRVTISVDTSKNQFSLKLSSVTAADTAVYYCARHSWDYFDYWDQGTLVTVSS Germ MKHLWFFLLLVAAPRWVLSQLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCAR-SC-YFDYWGQGTLVTVSS Signal peptide CDR1 CDR2 CDR3

FIG. 3H

Germline V=3-48, D=D4-17, J=JH4b 8.90.3 MELGLCWVFLVAILEGVQCEVQLVESGGGLVQPGGSLRLSCAASGFTFSRYSMNWVRQAPGKGLEWVSYISSRSSTIYYADSVKGRFTMSRDNAKNSLYMQMNSLRDEDTAVYYCG-YGDYDYFDYWGQGTLVTVSS Germ MELGLCWVFLVAILEGVQCEVQLVESGGGLVQPGGSLRLSCAASGFTFSSYSMNWVRQAPGKGLEWVSYISSSSSTIYYADSVKGRFTISRDNAKNSLYLQMNSLRDEDTAVYYCARYGDY-YFDYWGQGTLVTVSS Signal peptide CDR1 CDR2 CDR3

FIG. 6A atggactggacctggagcatccttttcttggtggcagca$X_5$caacaggtgcccactccCAGGTTCAGCTGGT

GCAGTCTGGAGCTGAGGTGAAGAAGCCTGGGGCCTCAGTGAAGGTCTCCT

GC$X_1$AGGCTTCTGGTTACACCTTTACCAGCTATGGTTTCAGCTGGGTGCGA
CDR1

CAGGCCCCTGGACAAGGGCTTGAGTGGATGGGATGGATCAGCGCTTCCAA
CDR2

TGGTAACACATACTATGCACAGAAGCTCCAGGGCAGAGTCACCATGACCA
CDR2 (continued (con't))

CAGACACATCCACGAGC$X_3$CAGCCTACATGGAGCTGAGGAGCCTGAGATC

TGACGACACGGCCGTGTATTACTGTGCGAGAGTCTACGCCGACTACGCTG
CDR3

ACTACTGGGGCCAGGGAACCCTGGTCACCGTCTCCTCAgcctccaccaagggcccat
CDR3 con't cggtcttcccctggcgccctgctccaggagcacctccgagagcacagcggccctgggctgcctggtcaaggactacttc cccgaaccggtgacggtgtcgtggaactcaggcgctctgaccagcggcgtgcacaccttcccagctgtcctacagtcctc aggactctactccctcagcagcgtggtgaccgtgccctccagcaacttcggcacccagacctacacctgcaacgtagatca caagcccagcaacaccaaggtggacaagacagttgagcgcaaatgttgtgtcgagtgcccaccgtgcccagcaccacct gtggcaggaccgtcagtcttcctcttccccccaaaacccaaggacaccctcatgatctcccggacccctgaggtcacgtgc gtggtggtggacgtgagccacgaagaccccgaggtccagttcaactggtacgtggacggcgtggaggtgcataatgcca agacaaagccacgggaggagcagttcaacagcacgttccgtgtggtcagcgtcctcaccgttgtgcaccaggactggctg aacggcaaggagtacaagtgcaaggtctccaacaaaggcctcccagcccccatcgagaaaaccatctccaaaaccaaag ggcagccccgagaaccacaggtgtacaccctgcccccatcccgggaggagatgaccaagaaccaggtcagcctgacct gcctggtcaaaggcttctaccccagcgacatcgccgtggagtgggagagcaatgggcagccggagaacaactacaaga ccacacctcccatgctggactccgacggctccttcttcctctacagcaagctcaccgtggacaagagcaggtggcagcag gggaacgtcttctcatgctccgtgatgcatgaggctctgcacaaccactacacgcagaagagcctctccctgtctccgggta aatga $X_1$: G or A
$X_3$:T or A
$X_5$:G or C

FIG. 6B mdwtwsilflvaa$X_6$tgahsQVQLVQSGAEVKKPGASVKVSC$X_2$ASGYTFTSYGFSWV
CDR1

RQAPGQGLEWMGWISASNGNTYYAQKLQGRVTMTTDTSTS$X_4$AYMELRSLR
CDR2

SDDTAVYYCARVYADYADYWGQGTLVTVSSastkgpsvfplapcsrstsestaalgclvkdyf
CDR3 pepvtvswnsgaltsgvhtfpavlqssglyslssvvtvpssnfgtqtytcnvdhkpsntkvdktverkccvecppcpap pvagpsvflfppkpkdtlmisrtpevtcvvvdvshedpevqfnwyvdgvevhnaktkpreeqfnstfrvvsvltvvh qdwlngkeykckvsnkglpapiektisktkgqprepqvytlppsreemtknqvsltclvkgfypsdiavewesngqp ennykttppmldsdgsfflyskltvdksrwqqgnvfscsvmhealhnhytqkslslspgk $X_2$:E or K
$X_4$:S or T
$X_6$:A or P

FIG. 6C atggacatgagggtccccgctcagctcctggggctcctgctgctctggttcccaggttccagatgcGACATCCAG

ATGACCCAGTCTCCATCTTCCGTGTCTGCATCTGTAGGAGACAGAGTCACC

ATCACTTGTCGGGCGAGTCAGGGTATTAACACCTGGTTAGCCTGGTATCA
CDR1

GCAGAAACCAGGGAAAGCCCCTAAACTCCTGATCTATGCTGCATCCAGTT
CDR2

TGAAAAGTGGGGTCCCATCAAGGTTCAGCGGCAGTGGATCTGGG$X_7$CAGA
CDR2 con't

TTTCACTCTCACCATCAGCAGCCTGCAGCCTGAAGATTTTGCAACTTACTA

TTGTCAACAGGCTAACAGTTTCCCTCTCACTTTCGGCGGAGGGACCAAGGT
CDR3

GGAGATCAAAcgaactgtggctgcaccatctgtcttcatcttcccgccatctgatgagcagttgaaatctggaactg cctctgttgtgtgcctgctgaataacttctatcccagagaggccaaagtacagtggaaggtggataacgccctccaatcggg taactcccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagagcttc aacaggggagagtgttag

$X_7$: G or A

FIG. 6D mdmrvpaqllgllllwfpgsrcDIQMTQSPSSVSASVGDRVTITCRASQGINTWLAWYQ
CDR1

QKPGKAPKLLIYAASSLKSGVPSRFSGSGSG$X_8$DFTLTISSLQPEDFATYYCQQ
CDR2 CDR3

ANSFPLTFGGGTKVEIKrtvaapsvfifppsdeqlksgtasvvcllnnfypreakvqwkvdnalqsgnsqe
CDR3 con't svteqdskdstyslsstltlskadyekhkvyacevthqglsspvtksfnrgec

$X_8$: A or T

*FIG. 6E* atgaaacacctgtggttcttcctcctgctggtggcagctcccagatgggtcctgtccCAGGTGCAGCTGCAGG

AGTCGGGCCCAGGACTGGTGAAGCCTTCACAGACCCTGTCCCTCACCTGC

ACTGTCTCTGGTGGCTCCATCAGCAGTGGTGGTTACTACTGGAGCTGGATC
CDR1

CGCCAGCACCCAGGGAAGGGCCTGGAGTGGATTGGGTACATCTATTACAG
CDR2

TGGGAGCACCTACTACAACCCGTCCCTCAAGAGTCGAGTTACCATATCAG
CDR2 con't

TAGACACGTCTAAGAACCAGTTCTCCCTGAAGCTGAGCTCTGTGACTGCC

GCGGACACGGCCGTGTATTACTGTGCGAGAGATGGGCCCCTAGGATATTG
CDR3

TAGTAGTACCAGCTGCCCGGTAACTGGGGAATACTACTACTACGGTATGG
CDR3 con't

ACGTCTGGGGCCAAGGGACCACGGTCACCGTCTCCTCAgcctccaccaagggcccat
CDR3 con't cggtcttccccctggcgccctgctccaggagcacctccgagagcacagcggccctgggctgcctggtcaaggactacttc cccgaaccggtgacggtgtcgtggaactcaggcgctctgaccagcggcgtgcacaccttcccagctgtcctacagtcctc aggactctactccctcagcagcgtggtgaccgtgccctccagcaacttcggcacccagacctacacctgcaacgtagatca caagcccagcaacaccaaggtggacaagacagttgagcgcaaatgttgtgtcgagtgcccaccgtgcccagcaccacct gtggcaggaccgtcagtcttcctcttccccccaaaacccaaggacaccctcatgatctcccggacccctgaggtcacgtgc gtggtggtggacgtgagccacgaagaccccgaggtccagttcaactggtacgtggacggcgtggaggtgcataatgcca agacaaagccacgggaggagcagttcaacagcacgttccgtgtggtcagcgtcctcaccgttgtgcaccaggactggctg aacggcaaggagtacaagtgcaaggtctccaacaaaggcctcccagcccccatcgagaaaaccatctccaaaaccaaag ggcagccccgagaaccacaggtgtacaccctgcccccatcccgggaggagatgaccaagaaccaggtcagcctgacct gcctggtcaaaggcttctaccccagcgacatcgccgtggagtgggagagcaatgggcagccggagaacaactacaaga ccacacctcccatgctggactccgacggctccttcttcctctacagcaagctcaccgtggacaagagcaggtggcagcag gggaacgtcttctcatgctccgtgatgcatgaggctctgcacaaccactacacgcagaagagcctctccctgtctccgggta aatga

FIG. 6F mkhlwfflllvaaprwvlsQVQLQESGPGLVKPSQTLSLTCTVSGGSISSGGYYWSWIR
CDR1

QHPGKGLEWIGYIYYSGSTYYNPSLKSRVTISVDTSKNQFSLKLSSVTAADTA
CDR2

VYYCARDGPLGYCSSTSCPVTGEYYYYGMDVWGQGTTVTVSSastkgpsvfplapc
CDR3 srstsestaalgclvkdyfpepvtvswnsgaltsgvhtfpavlqssglyslssvvtvpssnfgtqtytcnvdhkpsntkvd ktverkccvecppcpappvagpsvflfppkpkdtlmisrtpevtcvvvdvshedpevqfnwyvdgvevhnaktkpr eeqfnstfrvvsvltvvhqdwlngkeykckvsnkglpapiektisktkgqprepqvytlppsreemtknqvsltclvkg fypsdiavewesngqpennykttppmldsdgsfflyskltvdksrwqqgnvfscsvmhealhnhytqkslslspgk

FIG. 6G atggaaaccccagcgcagcttctcttcctcctgctactctggctcccagataccaccggaGAAATTGTGTTGAC

GCAGTCTCCAGGCACCCTGTCTTTGTCTCCAGGGGAAAGAGCCACCCTCTC

CTGCAGGGCCAGTCAGAGTGTTAGCAACAACTACTTAGCCTGGTACCAGC
CDR1

AGAAACCTGGCCAGGCTCCCAGGCTCCTCATCTTTGGTGCATCCAGCAGG
CDR2

GCCACTGGCATCCCAGACAGGTTCAGTGGCAGTGGGTCTGGGACAGACTT
CDR2 con't

CACTCTCACCATCAGCAGACTGGAGCCTGAAGATTTTGCAGTGTATTACTG

TCAGCAGTATGATATCTCACCTATGTACAGTTTTGGCCAGGGGACCAAGCT
CDR3

GGAGATGAAAcgaactgtggctgcaccatctgtcttcatcttcccgccatctgatgagcagttgaaatctggaactg cctctgttgtgtgcctgctgaataacttctatcccagagaggccaaagtacagtggaaggtggataacgccctccaatcggg taactcccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagagcttc aacaggggagagtgttag

FIG. 6H metpaqllfllllwlpdttgEIVLTQSPGTLSLSPGERATLSC<u>RASQSVSNNYLA</u>WYQQKP
                                                                                 CDR1

GQAPRLLIF<u>GASSRAT</u>GIPDRFSGSGSGTDFTLTISRLEPEDFAVYYC<u>QQYDISP</u>
          CDR2                                                                      CDR3

<u>MYSF</u>GQGTKLEMKrtvaapsvfifppsdeqlksgtasvvcllnnfypreakvqwkvdnalqsgnsqesvte
CDR3 con't qdskdstyslsstltlskadyekhkvyacevthqglsspvtksfnrgec

*FIG. 6I* atgaagcacctgtggttcttcctcctgctggtggcggctcccagatgggtcctgtccCAGCTGCAGCTGCAG

GAGTCGGGCCCAGGACTGGTGAAGCCTTCGGAGACCCTGTCCCTCACCTG

CACTGTCTCTGGTGGCTCCATCAGCAGTAGTAGTTACTACGGGGGCTGGAT
CDR1

CCGCCAGCCCCCAGGGAAGGGGCTGGATTGGATTGGGAGTATCTATTATA
CDR2

GTGGGAACACCTACTACAACCCGTCCCTCAAGAGTCGAGTCACCATATCC
CDR2 con't

GTAGACACGTCCAAGAACCAGTTCTCCCTGAAGCTGAGTTCTGTGACCGC

CGCAGACACGGCTGTGTATTACTGTGCGAGACATAGCTGGGACTACTTTG
CDR3

ACTACTGGGACCAGGGAACCCTGGTCACCGTCTCCTCAgcctccaccaagggcccat
CDR3 con't cggtcttccccctggcgccctgctccaggagcacctccgagagcacagcggccctgggctgcctggtcaaggactacttc cccgaaccggtgacggtgtcgtggaactcaggcgctctgaccagcggcgtgcacaccttcccagctgtcctacagtcctc aggactctactccctcagcagcgtggtgaccgtgccctccagcaacttcggcacccagacctacacctgcaacgtagatca caagcccagcaacaccaaggtggacaagacagttgagcgcaaatgttgtgtcgagtgcccaccgtgcccagcaccacct gtggcaggaccgtcagtcttcctcttccccccaaaacccaaggacaccctcatgatctcccggacccctgaggtcacgtgc gtggtggtggacgtgagccacgaagaccccgaggtccagttcaactggtacgtggacggcgtggaggtgcataatgcca agacaaagccacgggaggagcagttcaacagcacgttccgtgtggtcagcgtcctcaccgttgtgcaccaggactggctg aacggcaaggagtacaagtgcaaggtctccaacaaaggcctcccagcccccatcgagaaaaccatctccaaaaccaaag ggcagccccgagaaccacaggtgtacaccctgcccccatcccgggaggagatgaccaagaaccaggtcagcctgacct gcctggtcaaaggcttctaccccagcgacatcgccgtggagtgggagagcaatgggcagccggagaacaactacaaga ccacacctcccatgctggactccgacggctccttcttcctctacagcaagctcaccgtggacaagagcaggtggcagcag gggaacgtcttctcatgctccgtgatgcatgaggctctgcacaaccactacacgcagaagagcctctccctgtctccgggta aatga

FIG. 6J mkhlwfflllvaaprwvlsQLQLQESGPGLVKPSETLSLTCTVSGGSISSSSYYGGWIRQ
CDR1

PPGKGLDWIGSIYYSGNTYYNPSLKSRVTISVDTSKNQFSLKLSSVTAADTAV
CDR2

YYCARHSWDYFDYWDQGTLVTVSSastkgpsvfplapcsrstsestaalgclvkdyfpepvtvswn
CDR3 sgaltsgvhtfpavlqssglyslssvvtvpssnfgtqtytcnvdhkpsntkvdktverkccvecppcpappvagpsvflf ppkpkdtlmisrtpevtcvvvdvshedpevqfnwyvdgvevhnaktkpreeqfnstfrvvsvltvvhqdwlngkey kckvsnkglpapiektisktkgqprepqvytlppsreemtknqvsltclvkgfypsdiavewesngqpennykttpp mldsdgsfflyskltvdksrwqqgnvfscsvmhealhnhytqkslslspgk

FIG. 6K atggacatgagggtccccgctcagctcctggggctcctgctgctctggttcccaggttccagatgcGACATCCAG

ATGACCCAGTCTCCATCTTCCGTGTCTGCATCTGTAGGAGACAGAGTCACC

ATCACTTGTCGGGCGAGTCAGGGTATTAGCAGCTGGTTAGCCTGGTATCA
CDR1

GCAGAAACCAGGGAAAGCCCCTAAGCTCCTGATCTATGCTGCATCCAGTT
CDR2

TGCAAAGTGGGGTCCCATCAAGGTTCAGCGGCAGTGGATCTGGGACAGAT
CDR2 con't

TTCACTCTCACCATCAGCAGCCTGCAGTCTGAAGATTTTGCAACTTACTAT

TGTCAACAGGCTAACAGTTTCCCAATCACTTTCGGCCCTGGGACCAAAGT
CDR3

GGAAATCAAAcgaactgtggctgcaccatctgtcttcatcttcccgccatctgatgagcagttgaaatctggaactg cctctgttgtgtgcctgctgaataacttctatcccagagaggccaaagtacagtggaaggtggataacgccctccaatcggg taactcccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagagcttc aacaggggagagtgttag

FIG. 6L mdmrvpaqllgllllwfpgsrcDIQMTQSPSSVSASVGDRVTITC<u>RASQGISSWLA</u>WYQQ
                                                                         CDR1

KPGKAPKLLIY<u>AASSLQS</u>GVPSRFSGSGSGTDFTLTISSLQSEDFATYYC<u>QQAN</u>
           CDR2                                                                CDR3

<u>SFPIT</u>FGPGTKVEIKrtvaapsvfifppsdeqlksgtasvvcllnnfypreakvqwkvdnalqsgnsqesvte
CDR3 con't qdskdstyslsstltlskadyekhkvyacevthqglsspvtksfnrgec

*FIG. 6M* atggagttggggctgtgctgggttttccttgttgctattttagaaggtgtccagtgtGAGGTGCAGCTGGTGGA

GTCTGGGGGAGGCTTGGTACAGCCTGGGGGGTCCCTGAGACTCTCCTGTG

CAGCCTCTGGATTCACCTTCAGTAGATATAGCATGAATTGGGTCCGCCAG

CDR1

GCTCCAGGGAAGGGGCTGGAGTGGGTTTCATACATTAGTAGTAGAAGTAG

CDR2

TACCATATACTACGCAGACTCTGTGAAGGGCCGATTCACCATGTCCAGAG

CDR2 con't

ACAATGCCAAGAACTCACTGTATATGCAAATGAACAGCCTGAGAGACGAG

GACACGGCTGTGTATTACTGTGGCTACGGTGACTACGACTACTTTGACTAT

CDR3

TGGGGCCAGGGAACCCTGGTCACCGTCTCCTCAgcctccaccaagggcccatcggtcttcc ccctggcgccctgctccaggagcacctccgagagcacagcggccctgggctgcctggtcaaggactacttccccgaacc ggtgacggtgtcgtggaactcaggcgctctgaccagcggcgtgcacaccttcccagctgtcctacagtcctcaggactcta ctccctcagcagcgtggtgaccgtgccctccagcaacttcggcacccagacctacacctgcaacgtagatcacaagccca gcaacaccaaggtggacaagacagttgagcgcaaatgttgtgtcgagtgcccaccgtgcccagcaccacctgtggcagg accgtcagtcttcctcttccccccaaaacccaaggacaccctcatgatctcccggacccctgaggtcacgtgcgtggtggtg gacgtgagccacgaagaccccgaggtccagttcaactggtacgtggacggcgtggaggtgcataatgccaagacaaag ccacgggaggagcagttcaacagcacgttccgtgtggtcagcgtcctcaccgttgtgcaccaggactggctgaacggcaa ggagtacaagtgcaaggtctccaacaaaggcctcccagcccccatcgagaaaaccatctccaaaaccaaagggcagcc ccgagaaccacaggtgtacaccctgcccccatcccgggaggagatgaccaagaaccaggtcagcctgacctgcctggtc aaaggcttctaccccagcgacatcgccgtggagtgggagagcaatgggcagccggagaacaactacaagaccacacct cccatgctggactccgacggctccttcttcctctacagcaagctcaccgtggacaagagcaggtggcagcaggggaacgt cttctcatgctccgtgatgcatgaggctctgcacaaccactacacgcagaagagcctctccctgtctccgggtaaatga

FIG. 6N melglcwvflvailegvqcEVQLVESGGGLVQPGGSLRLSCAASGFTFSRYSMNWVRQ
CDR1

APGKGLEWVSYISSRSSTIYYADSVKGRFTMSRDNAKNSLYMQMNSLRDEDT
CDR2

AVYYCGYGDYDYFDYWGQGTLVTVSSastkgpsvfplapcsrstsestaalgclvkdyfpepvtv
CDR3 swnsgaltsgvhtfpavlqssglyslssvvtvpssnfgtqtytcnvdhkpsntkvdktverkccvecppcpappvagps vflfppkpkdtlmisrtpevtcvvvdvshedpevqfnwyvdgvevhnaktkpreeqfnstfrvvsvltvvhqdwlng keykckvsnkglpapiektisktkgqprepqvytlppsreemtknqvsltclvkgfypsdiavewesngqpennyktt ppmldsdgsfflyskltvdksrwqqgnvfscsvmhealhnhytqkslslspgk

FIG. 6O atggacatgagggtccccgctcagctcctggggctcctgctgctctggttcccaggttccagatgcGACATCCAG

ATGACCCAGTCTCCATCTTCCGTGTCTGCATCTGTAGGAGACAGAGTCATA

ATCACTTGTCGGGCGAGTCAGGGTATTAGCAGCTGGTTAGCCTGGTATCA
CDR1

GCAGAAACCAGGGAAAGCCCCTAAGCTCCTGATCTATGCTGCATCCAGTT
CDR2

TGAAAAGTGGGGTCCCATCAAGGTTCAGCGGCAGTGGATCTGGGACAGAT
CDR2 con't

TTCACTGTCACCATCAGCAGCCTGCAGCCTGAAGATTTTGCAACTTACTAT

GTCAACAGTCTAACAGTTTACCGTGGACGTTCGGCCAAGGGACCAAGGT
CDR3

GGAAATCAAAcgaactgtggctgcaccatctgtcttcatcttcccgccatctgatgagcagttgaaatctggaactg cctctgttgtgtgcctgctgaataacttctatcccagagaggccaaagtacagtggaaggtggataacgccctccaatcggg taactcccaggagagtgtcacagagcaggacagcaaggacagcacctacagcctcagcagcaccctgacgctgagcaa agcagactacgagaaacacaaagtctacgcctgcgaagtcacccatcagggcctgagctcgcccgtcacaaagagcttc aacaggggagagtgttag

FIG. 6P mdmrvpaqllgllllwfpgsrcDIQMTQSPSSVSASVGDRVIITC<u>RASQGISSWLA</u>WYQQ
                                                                                           CDR1

KPGKAPKLLIY<u>AASSLKS</u>GVPSRFSGSGSGTDFTVTISSLQPEDFATYYC<u>QQSN</u>
                 CDR2                                                                 CDR3

<u>SLPWT</u>FGQGTKVEIKrtvaapsvfifppsdeqlksgtasvvcllnnfypreakvqwkvdnalqsgnsqesvt
CDR3 con't eqdskdstyslsstltlskadyekhkvyacevthqglsspvtksfnrgec

SEQUENCE LISTING

```
<160> NUMBER OF SEQ ID NOS: 34

<210> SEQ ID NO 1
<211> LENGTH: 1389
<212> TYPE: DNA
<213> ORGANISM: Homo sapiens

<400> SEQUENCE: 1

atggactgga cctggagcat ccttttcttg gtggcagcas caacaggtgc ccactcccag      60

gttcagctgg tgcagtctgg agctgaggtg aagaagcctg gggcctcagt gaaggtctcc     120

tgcraggctt ctggttacac ctttaccagc tatggtttca gctgggtgcg acaggcccct     180

ggacaagggc ttgagtggat gggatggatc agcgcttcca atggtaacac atactatgca     240

cagaagctcc agggcagagt caccatgacc acagacacat ccacgagcwc agcctacatg     300

gagctgagga gcctgagatc tgacgacacg gccgtgtatt actgtgcgag agtctacgcc     360

gactacgctg actactgggg ccagggaacc ctggtcaccg tctcctcagc ctccaccaag     420

ggcccatcgg tcttcccct ggcgccctgc tccaggagca cctccgagag cacagcggcc      480

ctgggctgcc tggtcaagga ctacttcccc gaaccggtga cggtgtcgtg gaactcaggc     540

gctctgacca gcggcgtgca caccttccca gctgtcctac agtcctcagg actctactcc     600

ctcagcagcg tggtgaccgt gccctccagc aacttcggca cccagaccta cacctgcaac     660

gtagatcaca agcccagcaa caccaaggtg gacaagacag ttgagcgcaa atgttgtgtc     720

gagtgcccac cgtgcccagc accacctgtg gcaggaccgt cagtcttcct cttcccccca     780

aaacccaagg acaccctcat gatctcccgg acccctgagg tcacgtgcgt ggtggtggac     840

gtgagccacg aagaccccga ggtccagttc aactggtacg tggacggcgt ggaggtgcat     900

aatgccaaga caaagccacg ggaggagcag ttcaacagca cgttccgtgt ggtcagcgtc     960
```

```
ctcaccgttg tgcaccagga ctggctgaac ggcaaggagt acaagtgcaa ggtctccaac   1020

aaaggcctcc cagcccccat cgagaaaacc atctccaaaa ccaaagggca gccccgagaa   1080

ccacaggtgt acaccctgcc cccatcccgg gaggagatga ccaagaacca ggtcagcctg   1140

acctgcctgg tcaaaggctt ctaccccagc gacatcgccg tggagtggga gagcaatggg   1200

cagccggaga acaactacaa gaccacacct cccatgctgg actccgacgg ctccttcttc   1260

ctctacagca agctcaccgt ggacaagagc aggtggcagc aggggaacgt cttctcatgc   1320

tccgtgatgc atgaggctct gcacaaccac tacacgcaga agagcctctc cctgtctccg   1380

ggtaaatga                                                           1389


<210> SEQ ID NO 2
<211> LENGTH: 462
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: Ala or Pro
<220> FEATURE:
<221> NAME/KEY: MOD_RES
<222> LOCATION: (42)..(42)
<223> OTHER INFORMATION: Glu or Lys
<220> FEATURE:
<221> NAME/KEY: MOD_RES
<222> LOCATION: (97)..(97)
<223> OTHER INFORMATION: Ser or Thr

<400> SEQUENCE: 2

Met Asp Trp Thr Trp Ser Ile Leu Phe Leu Val Ala Ala Xaa Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Xaa Ala Ser Gly Tyr Thr Phe
        35                  40                  45

Thr Ser Tyr Gly Phe Ser Trp Val Arg Gln Ala Pro Gly Gln Gly Leu
    50                  55                  60

Glu Trp Met Gly Trp Ile Ser Ala Ser Asn Gly Asn Thr Tyr Tyr Ala
65                  70                  75                  80

Gln Lys Leu Gln Gly Arg Val Thr Met Thr Thr Asp Thr Ser Thr Ser
                85                  90                  95

Xaa Ala Tyr Met Glu Leu Arg Ser Leu Arg Ser Asp Asp Thr Ala Val
            100                 105                 110

Tyr Tyr Cys Ala Arg Val Tyr Ala Asp Tyr Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240
```

-continued

Glu Cys Pro Pro Cys Pro Ala Pro Pro Val Ala Gly Pro Ser Val Phe
245 250 255

Leu Phe Pro Pro Lys Pro Lys Asp Thr Leu Met Ile Ser Arg Thr Pro
260 265 270

Glu Val Thr Cys Val Val Val Asp Val Ser His Glu Asp Pro Glu Val
275 280 285

Gln Phe Asn Trp Tyr Val Asp Gly Val Glu Val His Asn Ala Lys Thr
290 295 300

Lys Pro Arg Glu Glu Gln Phe Asn Ser Thr Phe Arg Val Val Ser Val
305 310 315 320

Leu Thr Val Val His Gln Asp Trp Leu Asn Gly Lys Glu Tyr Lys Cys
325 330 335

Lys Val Ser Asn Lys Gly Leu Pro Ala Pro Ile Glu Lys Thr Ile Ser
340 345 350

Lys Thr Lys Gly Gln Pro Arg Glu Pro Gln Val Tyr Thr Leu Pro Pro
355 360 365

Ser Arg Glu Glu Met Thr Lys Asn Gln Val Ser Leu Thr Cys Leu Val
370 375 380

Lys Gly Phe Tyr Pro Ser Asp Ile Ala Val Glu Trp Glu Ser Asn Gly
385 390 395 400

Gln Pro Glu Asn Asn Tyr Lys Thr Thr Pro Pro Met Leu Asp Ser Asp
405 410 415

Gly Ser Phe Phe Leu Tyr Ser Lys Leu Thr Val Asp Lys Ser Arg Trp
420 425 430

Gln Gln Gly Asn Val Phe Ser Cys Ser Val Met His Glu Ala Leu His
435 440 445

Asn His Tyr Thr Gln Lys Ser Leu Ser Leu Ser Pro Gly Lys
450 455 460

<210> SEQ ID NO 3
<211> LENGTH: 711
<212> TYPE: DNA
<213> ORGANISM: Homo sapiens

<400> SEQUENCE: 3
atggacatga gggtccccgc tcagctcctg gggctcctgc tgctctggtt cccaggttcc 60
agatgcgaca tccagatgac ccagtctcca tcttccgtgt ctgcatctgt aggagacaga 120
gtcaccatca cttgtcgggc gagtcagggt attaacacct ggttagcctg gtatcagcag 180
aaaccaggga aagcccctaa actcctgatc tatgctgcat ccagtttgaa aagtggggtc 240
ccatcaaggt tcagcggcag tggatctggg rcagatttca ctctcaccat cagcagcctg 300
cagcctgaag attttgcaac ttactattgt caacaggcta acagtttccc tctcactttc 360
ggcggaggga ccaaggtgga gatcaaacga actgtggctg caccatctgt cttcatcttc 420
ccgccatctg atgagcagtt gaaatctgga actgcctctg ttgtgtgcct gctgaataac 480
ttctatccca gagaggccaa agtacagtgg aaggtggata acgccctcca atcgggtaac 540
tcccaggaga gtgtcacaga gcaggacagc aaggacagca cctacagcct cagcagcacc 600
ctgacgctga gcaaagcaga ctacgagaaa cacaaagtct acgcctgcga agtcacccat 660
cagggcctga gctcgcccgt cacaaagagc ttcaacaggg gagagtgtta g 711

<210> SEQ ID NO 4
<211> LENGTH: 236
<212> TYPE: PRT
<213> ORGANISM: Homo sapiens
<220> FEATURE:
<221> NAME/KEY: MOD_RES
<222> LOCATION: (91)..(91)
<223> OTHER INFORMATION: Ala or Thr

<400> SEQUENCE: 4

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Asn Thr Trp Leu Ala Trp Tyr Gln Gln Lys Pro Gly Lys
    50                  55                  60

Ala Pro Lys Leu Leu Ile Tyr Ala Ala Ser Ser Leu Lys Ser Gly Val
65                  70                  75                  80

Pro Ser Arg Phe Ser Gly Ser Gly Ser Gly Xaa Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 5
<211> LENGTH: 1443
<212> TYPE: DNA
<213> ORGANISM: Homo sapiens

<400> SEQUENCE: 5

```
atgaaacacc tgtggttctt cctcctgctg gtggcagctc ccagatgggt cctgtcccag      60

gtgcagctgc aggagtcggg cccaggactg gtgaagcctt cacagaccct gtccctcacc     120

tgcactgtct ctggtggctc catcagcagt ggtggttact actggagctg gatccgccag     180

cacccaggga agggcctgga gtggattggg tacatctatt acagtgggag cacctactac     240

aacccgtccc tcaagagtcg agttaccata tcagtagaca cgtctaagaa ccagttctcc     300

ctgaagctga gctctgtgac tgccgcggac acggccgtgt attactgtgc gagagatggg     360

cccctaggat attgtagtag taccagctgc ccggtaactg gggaatacta ctactacggt     420

atggacgtct ggggccaagg gaccacggtc accgtctcct cagcctccac caagggccca     480

tcggtcttcc ccctggcgcc ctgctccagg agcacctccg agagcacagc ggccctgggc     540

tgcctggtca aggactactt ccccgaaccg gtgacggtgt cgtggaactc aggcgctctg     600
```

accagcggcg tgcacacctt cccagctgtc ctacagtcct caggactcta ctccctcagc 660
agcgtggtga ccgtgccctc cagcaacttc ggcacccaga cctacacctg caacgtagat 720
cacaagccca gcaacaccaa ggtggacaag acagttgagc gcaaatgttg tgtcgagtgc 780
ccaccgtgcc cagcaccacc tgtggcagga ccgtcagtct tcctcttccc cccaaaaccc 840
aaggacaccc tcatgatctc ccggacccct gaggtcacgt gcgtggtggt ggacgtgagc 900
cacgaagacc ccgaggtcca gttcaactgg tacgtggacg gcgtggaggt gcataatgcc 960
aagacaaagc cacgggagga gcagttcaac agcacgttcc gtgtggtcag cgtcctcacc 1020
gttgtgcacc aggactggct gaacggcaag gagtacaagt gcaaggtctc caacaaaggc 1080
ctcccagccc ccatcgagaa aaccatctcc aaaaccaaag ggcagccccg agaaccacag 1140
gtgtacaccc tgcccccatc ccgggaggag atgaccaaga accaggtcag cctgacctgc 1200
ctggtcaaag gcttctaccc cagcgacatc gccgtggagt gggagagcaa tgggcagccg 1260
gagaacaact acaagaccac acctcccatg ctggactccg acggctcctt cttcctctac 1320
agcaagctca ccgtggacaa gagcaggtgg cagcagggga acgtcttctc atgctccgtg 1380
atgcatgagg ctctgcacaa ccactacacg cagaagagcc tctccctgtc tccgggtaaa 1440
tga 1443

<210> SEQ ID NO 6
<211> LENGTH: 480
<212> TYPE: PRT
<213> ORGANISM: Homo sapiens

<400> SEQUENCE: 6

Met Lys His Leu Trp Phe Phe Leu Leu Leu Val Ala Ala Pro Arg Trp
1 5 10 15

Val Leu Ser Gln Val Gln Leu Gln Glu Ser Gly Pro Gly Leu Val Lys
20 25 30

Pro Ser Gln Thr Leu Ser Leu Thr Cys Thr Val Ser Gly Gly Ser Ile
35 40 45

Ser Ser Gly Gly Tyr Tyr Trp Ser Trp Ile Arg Gln His Pro Gly Lys
50 55 60

Gly Leu Glu Trp Ile Gly Tyr Ile Tyr Tyr Ser Gly Ser Thr Tyr Tyr
65 70 75 80

Asn Pro Ser Leu Lys Ser Arg Val Thr Ile Ser Val Asp Thr Ser Lys
85 90 95

Asn Gln Phe Ser Leu Lys Leu Ser Ser Val Thr Ala Ala Asp Thr Ala
100 105 110

Val Tyr Tyr Cys Ala Arg Asp Gly Pro Leu Gly Tyr Cys Ser Ser Thr
115 120 125

Ser Cys Pro Val Thr Gly Glu Tyr Tyr Tyr Tyr Gly Met Asp Val Trp
130 135 140

Gly Gln Gly Thr Thr Val Thr Val Ser Ser Ala Ser Thr Lys Gly Pro
145 150 155 160

Ser Val Phe Pro Leu Ala Pro Cys Ser Arg Ser Thr Ser Glu Ser Thr
165 170 175

Ala Ala Leu Gly Cys Leu Val Lys Asp Tyr Phe Pro Glu Pro Val Thr
180 185 190

Val Ser Trp Asn Ser Gly Ala Leu Thr Ser Gly Val His Thr Phe Pro
195 200 205

Ala Val Leu Gln Ser Ser Gly Leu Tyr Ser Leu Ser Ser Val Val Thr
210 215 220

-continued

```
Val Pro Ser Ser Asn Phe Gly Thr Gln Thr Tyr Thr Cys Asn Val Asp
225                 230                 235                 240

His Lys Pro Ser Asn Thr Lys Val Asp Lys Thr Val Glu Arg Lys Cys
                245                 250                 255

Cys Val Glu Cys Pro Pro Cys Pro Ala Pro Pro Val Ala Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Gln Phe Asn Trp Tyr Val Asp Gly Val Glu Val His Asn Ala
305                 310                 315                 320

Lys Thr Lys Pro Arg Glu Glu Gln Phe Asn Ser Thr Phe Arg Val Val
                325                 330                 335

Ser Val Leu Thr Val Val His Gln Asp Trp Leu Asn Gly Lys Glu Tyr
            340                 345                 350

Lys Cys Lys Val Ser Asn Lys Gly Leu Pro Ala Pro Ile Glu Lys Thr
        355                 360                 365

Ile Ser Lys Thr Lys Gly Gln Pro Arg Glu Pro Gln Val Tyr Thr Leu
    370                 375                 380

Pro Pro Ser Arg Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Met Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480


<210> SEQ ID NO 7
<211> LENGTH: 711
<212> TYPE: DNA
<213> ORGANISM: Homo sapiens

<400> SEQUENCE: 7

atggaaaccc cagcgcagct tctcttcctc ctgctactct ggctcccaga taccaccgga     60

gaaattgtgt tgacgcagtc tccaggcacc ctgtctttgt ctccagggga aagagccacc    120

ctctcctgca gggccagtca gagtgttagc aacaactact tagcctggta ccagcagaaa    180

cctggccagg ctcccaggct cctcatcttt ggtgcatcca gcagggccac tggcatccca    240

gacaggttca gtggcagtgg gtctgggaca gacttcactc tcaccatcag cagactggag    300

cctgaagatt ttgcagtgta ttactgtcag cagtatgata tctcacctat gtacagtttt    360

ggccagggga ccaagctgga gatgaaacga actgtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgtta g             711
```

<210> SEQ ID NO 8
<211> LENGTH: 236
<212> TYPE: PRT
<213> ORGANISM: Homo sapiens

<400> SEQUENCE: 8

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Asn Asn Tyr Leu Ala Trp Tyr Gln Gln Lys Pro Gly Gln Ala
    50                  55                  60

Pro Arg Leu Leu Ile Phe Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Ile Ser Pro Met Tyr Ser Phe Gly Gln Gly Thr Lys Leu Glu Met
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 9
<211> LENGTH: 1392
<212> TYPE: DNA
<213> ORGANISM: Homo sapiens

<400> SEQUENCE: 9

```
atgaagcacc tgtggttctt cctcctgctg gtggcggctc ccagatgggt cctgtcccag      60

ctgcagctgc aggagtcggg cccaggactg gtgaagcctt cggagaccct gtccctcacc     120

tgcactgtct ctggtggctc catcagcagt agtagttact acgggggctg gatccgccag     180

cccccaggga aggggctgga ttggattggg agtatctatt atagtgggaa cacctactac     240

aacccgtccc tcaagagtcg agtcaccata tccgtagaca cgtccaagaa ccagttctcc     300

ctgaagctga gttctgtgac cgccgcagac acggctgtgt attactgtgc gagacatagc     360

tgggactact ttgactactg gggccaggga accctggtca ccgtctcctc agcctccacc     420

aagggcccat cggtcttccc cctggcgccc tgctccagga gcacctccga gagcacagcg     480

gccctgggct gcctggtcaa ggactacttc cccgaaccgg tgacggtgtc gtggaactca     540

ggcgctctga ccagcggcgt gcacaccttc ccagctgtcc tacagtcctc aggactctac     600
```

```
tccctcagca gcgtggtgac cgtgccctcc agcaacttcg gcacccagac ctacacctgc    660

aacgtagatc acaagcccag caacaccaag gtggacaaga cagttgagcg caaatgttgt    720

gtcgagtgcc caccgtgccc agcaccacct gtggcaggac cgtcagtctt cctcttcccc    780

ccaaaaccca aggacaccct catgatctcc cggacccctg aggtcacgtg cgtggtggtg    840

gacgtgagcc acgaagaccc cgaggtccag ttcaactggt acgtggacgg cgtggaggtg    900

cataatgcca agacaaagcc acgggaggag cagttcaaca gcacgttccg tgtggtcagc    960

gtcctcaccg ttgtgcacca ggactggctg aacggcaagg agtacaagtg caaggtctcc   1020

aacaaaggcc tcccagcccc catcgagaaa accatctcca aaaccaaagg gcagccccga   1080

gaaccacagg tgtacaccct gcccccatcc cgggaggaga tgaccaagaa ccaggtcagc   1140

ctgacctgcc tggtcaaagg cttctacccc agcgacatcg ccgtggagtg ggagagcaat   1200

gggcagccgg agaacaacta caagaccaca cctcccatgc tggactccga cggctccttc   1260

ttcctctaca gcaagctcac cgtggacaag agcaggtggc agcaggggaa cgtcttctca   1320

tgctccgtga tgcatgaggc tctgcacaac cactacacgc agaagagcct ctccctgtct   1380

ccgggtaaat ga                                                       1392
```

<210> SEQ ID NO 10
<211> LENGTH: 463
<212> TYPE: PRT
<213> ORGANISM: Homo sapiens

<400> SEQUENCE: 10

```
Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Tyr Gly Gly Trp Ile Arg Gln Pro Pro Gly Lys
    50                  55                  60

Gly Leu Asp Trp Ile Gly Ser Ile Tyr Tyr Ser Gly Asn Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg His Ser Trp Asp Tyr Phe Asp Tyr Trp Asp
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
```

-continued

```
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

```
<210> SEQ ID NO 11
<211> LENGTH: 711
<212> TYPE: DNA
<213> ORGANISM: Homo sapiens

<400> SEQUENCE: 11

atggacatga gggtccccgc tcagctcctg gggctcctgc tgctctggtt cccaggttcc      60

agatgcgaca tccagatgac ccagtctcca tcttccgtgt ctgcatctgt aggagacaga     120

gtcaccatca cttgtcgggc gagtcagggt attagcagct ggttagcctg gtatcagcag     180

aaaccaggga aagcccctaa gctcctgatc tatgctgcat ccagtttgca aagtggggtc     240

ccatcaaggt tcagcggcag tggatctggg acagatttca ctctcaccat cagcagcctg     300

cagtctgaag attttgcaac ttactattgt caacaggcta acagtttccc aatcactttc     360

ggccctggga ccaaagtgga aatcaaacga actgtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgtta g              711

<210> SEQ ID NO 12
<211> LENGTH: 236
<212> TYPE: PRT
```

<213> ORGANISM: Homo sapiens

<400> SEQUENCE: 12

Met Asp Met Arg Val Pro Ala Gln Leu Leu Gly Leu Leu Leu Leu Trp
1 5 10 15

Phe Pro Gly Ser Arg Cys Asp Ile Gln Met Thr Gln Ser Pro Ser Ser
20 25 30

Val Ser Ala Ser Val Gly Asp Arg Val Thr Ile Thr Cys Arg Ala Ser
35 40 45

Gln Gly Ile Ser Ser Trp Leu Ala Trp Tyr Gln Gln Lys Pro Gly Lys
50 55 60

Ala Pro Lys Leu Leu Ile Tyr Ala Ala Ser Ser Leu Gln Ser Gly Val
65 70 75 80

Pro Ser Arg Phe Ser Gly Ser Gly Ser Gly Thr Asp Phe Thr Leu Thr
85 90 95

Ile Ser Ser Leu Gln Ser Glu Asp Phe Ala Thr Tyr Tyr Cys Gln Gln
100 105 110

Ala Asn Ser Phe Pro Ile Thr Phe Gly Pro Gly Thr Lys Val Glu Ile
115 120 125

Lys Arg Thr Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

Phe Tyr Pro Arg Glu Ala Lys Val Gln Trp Lys Val Asp Asn Ala Leu
165 170 175

Gln Ser Gly Asn Ser Gln Glu Ser Val Thr Glu Gln Asp Ser Lys Asp
180 185 190

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys
225 230 235

<210> SEQ ID NO 13
<211> LENGTH: 1389
<212> TYPE: DNA
<213> ORGANISM: Homo sapiens

<400> SEQUENCE: 13
atggagttgg ggctgtgctg ggttttcctt gttgctattt tagaaggtgt ccagtgtgag 60
gtgcagctgg tggagtctgg gggaggcttg gtacagcctg gggggtccct gagactctcc 120
tgtgcagcct ctggattcac cttcagtaga tatagcatga attgggtccg ccaggctcca 180
gggaaggggc tggagtgggt ttcatacatt agtagtagaa gtagtaccat atactacgca 240
gactctgtga agggccgatt caccatgtcc agagacaatg ccaagaactc actgtatatg 300
caaatgaaca gcctgagaga cgaggacacg gctgtgtatt actgtggcta cggtgactac 360
gactactttg actattgggg ccagggaacc ctggtcaccg tctcctcagc ctccaccaag 420
ggcccatcgg tcttccccct ggcgccctgc tccaggagca cctccgagag cacagcggcc 480
ctgggctgcc tggtcaagga ctacttcccc gaaccggtga cggtgtcgtg gaactcaggc 540
gctctgacca gcggcgtgca caccttccca gctgtcctac agtcctcagg actctactcc 600
ctcagcagcg tggtgaccgt gccctccagc aacttcggca cccagaccta cacctgcaac 660
gtagatcaca agcccagcaa caccaaggtg gacaagacag ttgagcgcaa atgttgtgtc 720

-continued

```
gagtgcccac cgtgcccagc accacctgtg gcaggaccgt cagtcttcct cttcccccca    780

aaacccaagg acaccctcat gatctcccgg acccctgagg tcacgtgcgt ggtggtggac    840

gtgagccacg aagaccccga ggtccagttc aactggtacg tggacggcgt ggaggtgcat    900

aatgccaaga caaagccacg ggaggagcag ttcaacagca cgttccgtgt ggtcagcgtc    960

ctcaccgttg tgcaccagga ctggctgaac ggcaaggagt acaagtgcaa ggtctccaac   1020

aaaggcctcc cagcccccat cgagaaaacc atctccaaaa ccaaagggca gccccgagaa   1080

ccacaggtgt acaccctgcc cccatcccgg gaggagatga ccaagaacca ggtcagcctg   1140

acctgcctgg tcaaaggctt ctaccccagc gacatcgccg tggagtggga gagcaatggg   1200

cagccggaga acaactacaa gaccacacct cccatgctgg actccgacgg ctccttcttc   1260

ctctacagca agctcaccgt ggacaagagc aggtggcagc aggggaacgt cttctcatgc   1320

tccgtgatgc atgaggctct gcacaaccac tacacgcaga agagcctctc cctgtctccg   1380

ggtaaatga                                                           1389
```

```
<210> SEQ ID NO 14
<211> LENGTH: 462
<212> TYPE: PRT
<213> ORGANISM: Homo sapiens

<400> SEQUENCE: 14

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Ser Met Asn Trp Val Arg Gln Ala Pro Gly Lys Gly Leu
    50                  55                  60

Glu Trp Val Ser Tyr Ile Ser Ser Arg Ser Ser Thr Ile Tyr Tyr Ala
65                  70                  75                  80

Asp Ser Val Lys Gly Arg Phe Thr Met Ser Arg Asp Asn Ala Lys Asn
                85                  90                  95

Ser Leu Tyr Met Gln Met Asn Ser Leu Arg Asp Glu Asp Thr Ala Val
            100                 105                 110

Tyr Tyr Cys Gly Tyr Gly Asp Tyr Asp Tyr Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255
```

```
Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 15
<211> LENGTH: 710
<212> TYPE: DNA
<213> ORGANISM: Homo sapiens

<400> SEQUENCE: 15

```
atggacatga gggtccccgc tcagctcctg gggctcctgc tgctctggtt cccaggttcc      60

agatgcgaca tccagatgac ccagtctcca tcttccgtgt ctgcatctgt aggagacaga     120

gtcataatca cttgtcgggc gagtcagggt attagcagct ggttagcctg gtatcagcag     180

aaaccaggga aagcccctaa gctcctgatc tatgctgcat ccagtttgaa aagtggggtc     240

ccatcaaggt tcagcggcag tggatctggg acagatttca ctgtcaccat cagcagcctg     300

cagcctgaag attttgcaac ttactatgtc aacagtctaa cagtttaccg tggacgttcg     360

gccaagggac caaggtggaa atcaaacgaa ctgtggctgc accatctgtc ttcatcttcc     420

cgccatctga tgagcagttg aaatctggaa ctgcctctgt tgtgtgcctg ctgaataact     480

tctatcccag agaggccaaa gtacagtgga aggtggataa cgccctccaa tcgggtaact     540

cccaggagag tgtcacagag caggacagca aggacagcac ctacagcctc agcagcaccc     600

tgacgctgag caaagcagac tacgagaaac acaaagtcta cgcctgcgaa gtcacccatc     660

agggcctgag ctcgcccgtc acaaagagct tcaacagggg agagtgttag                710
```

<210> SEQ ID NO 16
<211> LENGTH: 236
<212> TYPE: PRT
<213> ORGANISM: Homo sapiens

<400> SEQUENCE: 16

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Ile Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Lys Ser Gly Val
65                  70                  75                  80

Pro Ser Arg Phe Ser Gly Ser Gly Ser Gly Thr Asp Phe Thr Val Thr
                85                  90                  95

Ile Ser Ser Leu Gln Pro Glu Asp Phe Ala Thr Tyr Tyr Cys Gln Gln
            100                 105                 110

Ser Asn Ser Leu Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 17
<211> LENGTH: 129
<212> TYPE: PRT
<213> ORGANISM: Homo sapiens

<400> SEQUENCE: 17

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Leu Thr Phe Gly Gly Gly Thr Lys Val Glu Ile
        115                 120                 125

Lys
```

-continued

<210> SEQ ID NO 18
<211> LENGTH: 128
<212> TYPE: PRT
<213> ORGANISM: Homo sapiens

<400> SEQUENCE: 18

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125
```

<210> SEQ ID NO 19
<211> LENGTH: 129
<212> TYPE: PRT
<213> ORGANISM: Homo sapiens

<400> SEQUENCE: 19

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys
```

<210> SEQ ID NO 20
<211> LENGTH: 129
<212> TYPE: PRT
<213> ORGANISM: Homo sapiens

<400> SEQUENCE: 20

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
```

```
        35                  40                  45

Gln Gly Ile Ser Ser Trp Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Trp Thr Phe Gly Gln Gly Thr Lys Val Glu Ile
        115                 120                 125

Lys


<210> SEQ ID NO 21
<211> LENGTH: 132
<212> TYPE: PRT
<213> ORGANISM: Homo sapiens

<400> SEQUENCE: 21

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Tyr Ser Tyr Phe Trp Gly Gln Gly Thr Leu Val
        115                 120                 125

Thr Val Ser Ser
    130


<210> SEQ ID NO 22
<211> LENGTH: 149
<212> TYPE: PRT
<213> ORGANISM: Homo sapiens

<400> SEQUENCE: 22

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Gly Tyr Tyr Trp Ser Trp Ile Arg Gln His Pro Gly Lys
    50                  55                  60

Gly Leu Glu Trp Ile Gly Tyr Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95
```

-continued

Asn Gln Phe Ser Leu Lys Leu Ser Ser Val Thr Ala Ala Asp Thr Ala
100 105 110

Val Tyr Tyr Cys Ala Arg Gly Tyr Cys Ser Ser Thr Ser Cys Thr Gly
115 120 125

Asp Tyr Tyr Tyr Tyr Tyr Gly Met Asp Val Trp Gly Gln Gly Thr Thr
130 135 140

Val Thr Val Ser Ser
145

<210> SEQ ID NO 23
<211> LENGTH: 135
<212> TYPE: PRT
<213> ORGANISM: Homo sapiens

<400> SEQUENCE: 23

Met Lys His Leu Trp Phe Phe Leu Leu Leu Val Ala Ala Pro Arg Trp
1 5 10 15

Val Leu Ser Gln Leu Gln Leu Gln Glu Ser Gly Pro Gly Leu Val Lys
20 25 30

Pro Ser Glu Thr Leu Ser Leu Thr Cys Thr Val Ser Gly Gly Ser Ile
35 40 45

Ser Ser Ser Ser Tyr Tyr Trp Gly Trp Ile Arg Gln Pro Pro Gly Lys
50 55 60

Gly Leu Glu Trp Ile Gly Ser Ile Tyr Tyr Ser Gly Ser Thr Tyr Tyr
65 70 75 80

Asn Pro Ser Leu Lys Ser Arg Val Thr Ile Ser Val Asp Thr Ser Lys
85 90 95

Asn Gln Phe Ser Leu Lys Leu Ser Ser Val Thr Ala Ala Asp Thr Ala
100 105 110

Val Tyr Tyr Cys Ala Arg Ser Cys Tyr Phe Asp Tyr Trp Gly Gln Gly
115 120 125

Thr Leu Val Thr Val Ser Ser
130 135

<210> SEQ ID NO 24
<211> LENGTH: 136
<212> TYPE: PRT
<213> ORGANISM: Homo sapiens

<400> SEQUENCE: 24

Met Glu Leu Gly Leu Cys Trp Val Phe Leu Val Ala Ile Leu Glu Gly
1 5 10 15

Val Gln Cys Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Ser Met Asn Trp Val Arg Gln Ala Pro Gly Lys Gly Leu
50 55 60

Glu Trp Val Ser Tyr Ile Ser Ser Ser Ser Ser Thr Ile Tyr Tyr Ala
65 70 75 80

Asp Ser Val Lys Gly Arg Phe Thr Ile Ser Arg Asp Asn Ala Lys Asn
85 90 95

Ser Leu Tyr Leu Gln Met Asn Ser Leu Arg Asp Glu Asp Thr Ala Val
100 105 110

Tyr Tyr Cys Ala Arg Tyr Gly Asp Tyr Tyr Phe Asp Tyr Trp Gly Gln
115 120 125

Gly Thr Leu Val Thr Val Ser Ser 130 135

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (21)..(21)
<223> OTHER INFORMATION: i

<400> SEQUENCE: 25
caggtgcagc tggagcagtc ngg 23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 26
gctgagggag tagagtcctg agga 24

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 27
ttctctgatc agaattccta tcatttaccc ggagacaggg agag 44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 28
tatctaagct tctagacgcc accatggaca tgagggtccc cgct 44

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 29
tatctaagct tctagacgcc accatggaaa ccccagcgca gcttc 45

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 30
ttctttgatc agaattctca ctaacactct cccctgttga agc 43

<210> SEQ ID NO 31

-continued

```
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 31

tatctaagct tctagacgcc accatggact ggacctggag catc                44


<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 32

tatctaagct tctagacgcc accatgaaac acctgtggtt cttc                44


<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 33

tatctaagct tctagacgcc accatgaagc acctgtggtt cttc                44


<210> SEQ ID NO 34
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 34

tatctaagct tctagacgcc accatggagt tggggctgtg ctgg                44
```

ANTIBODIES TO C-MET

CROSS REFERENCE TO RELATED APPLICATIONS

This application is a continuation application of U.S. patent application Ser. No. 12/321,963, filed Jan. 26, 2009, now allowed, which is a divisional application of U.S. patent application Ser. No. 10/910,901, filed Aug. 3, 2004, now U.S. Pat. No. 7,498,420, which claims the benefit of U.S. Provisional Application No. 60/492,432 filed Aug. 4, 2003, The entire contents of each of the above-referenced patent applications are incorporated herein by this reference.

REFERENCE TO THE SEQUENCE LISTING

The present application is being filed along with a Sequence Listing in electronic format. The Sequence Listing is provided as a file entitled ABX-136-US-CNT_SeqListing-final.txt created Apr. 24, 2012 which is 48 KB in size. The information in the electronic format of the Sequence Listing is incorporated herein by reference in its entirety.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways.

In order to produce cellular effects, HGF must bind to its receptor, c-Met, a receptor tyrosine kinase. c-Met is a widely expressed heterodimeric protein comprising of a 50 kilodalton (kDa) α-subunit and a 145 kDa β-subunit (Maggiora et al., *J. Cell Physiol,* 173:183-186 (1997)). The c-Met β-subunit comprises the tyrosine kinase domain and two autophosphorylation sites, Y1349 and Y1356, that are critical for transmission of the HGF signal (Maggiora et al., *J. Cell Physiol,* 173:183-186 (1997); Ponzetto et al., *Cell,* 77:2610271 (1994); Maina et al., *Cell,* 87:531-542 (1996)).

HGF binding to c-Met results in activation of a number of signaling pathways that result in various cellular activities associated with diseases like cancer. These include promoting mitogenesis, cell survival, cell motility, invasion of the extracellular matrix (ECM), angiogenesis and metastasis, all of which are activities that promote transformation and disease progression (Jeffers et al., *J. Mol. Med.,* 74:505-513 (1996); Amicone et al., *EMBO J.,* 16:495-503 (1997); Matsumoto and Nakamura, *Biochem. Biophys. Res. Comm.,* 239: 639-644 (1997); Corps et al., *Int. J. Cancer,* 73:151-155 (1997)). Expression or over-expression of both HGF and c-Met can result in morphological transformation and tumorigenicity of several cell types (Jeffers et al., *J. Mol. Med.,* 74:505-513 (1996). HGF and c-Met expression or over-expression also promote mitogenesis and anchorage independent growth (Rubin et al., *Proc. Natl. Acad. Sci. USA,* 88:514-419 (1991); Kan et al., *Biochem. Biophys. Res. Commun.,* 174:331-337 (1991). In particular, invasion of the ECM has been reported when activation of c-Met causes the expression of proteases, such as urokinase-like plasminogen activator and collegenase, allowing cells to degrade and locally invade tissue (Jeffers et al., *J. Mol. Med,* 74:505-513 (1996). Further, several tumors that express or over-express only c-Met, and not HGF, utilize a paracrine rather than an autocrine signaling mechanism to support tumorigenesis (Beviglio et al., *Int. J. Cancer,* 74:301-309 (1997).

HGF and c-Met also have been implicated in the etiology of many human cancers. Concomitant expression or over-expression of HGF and c-Met has been observed in breast carcinoma (Nagy et al., *Surg. Oncol.,* 5:15-21 (1996); Tuck et al., *Am. J. Pathol.,* 148:225-232 (1996), pancreatic carcinoma (Ebert et al., *Cancer Res.,* 54:5775-5778 (1994), oral squamous cell carcinoma (Marshall and Kornberg, *Laryngoscope,* 108:1413-1417 (1998), gliomas (Koochekpour et al., *Cancer Res.,* 57:5391-5398 (1997), and malignant pleural mesotheliomas (Tolpay et al., *J. Cancer Res. Clin. Oncol.,* 124:291-296 (1998); Klominek et al. *Intl. J. Cancer,* 76:240-249 (1998)). In addition, over-production of c-Met may be important in the development of other tumors in which a role for HGF has yet to be substantiated. These cancers include hepatocellular carcinoma (Suzuki et al. *Hepatology,* 20:1231-1236 (1996), renal cell carcinoma (Natali et al., *Intl. J. Cancer,* 69:212-217 (1996), lung carcinoma (Harvey et al., *J. Pathol.,* 180:389-394 (1996), ovarian cancer (Nagy et al., *J. Surg. Oncol.,* 60:95-99 (1995), gastric carcinoma (Taniguchi et al., *Cancer,* 82:2112-2122 (1998), and colorectal carcinoma (Hiscox et al., *Cancer Invest.,* 15:513-521 (1997). In addition, germline and somatic mutations that activate the c-Met receptor in the absence of HGF in individuals with papillary renal carcinomas have been reported (Schmidt et al., *Nat. Genet.,* 16:68-73 (1997); Jeffers et al., *Proc. Natl. Acad. Sci. USA,* 94:11445-11450 (1997)). Other carcinomas, including those of the stomach, rectum, lung, pancreas, breast, and bile duct have been detected in individuals with c-Met containing activating mutations (Zbar et al., *J. Urol.,* 151:561-566 (1994).

A strategy for inhibiting c Met binding is needed to prevent activation of pathways leading to diseases such as cancer. C-Met function may attenuate c-Met activation and/or HGF-induced biological responses (Date et al., *FEBS Letters,* 420: 1-6 (1997); (Kaji et al, *Cancer Gene Ther.,* 3:393-404 (1996); (Li et al., *Clin. Exp. Metastasis,* 16:74-82 (1998)) and therefore inhibit tumor progression. Although mouse anti-c-Met monoclonal antibodies having anti-mitogenic activity in cell culture have been reported (U.S. Pat. Nos. 5,646,036, 6,207,152, 6,214,344), a mouse antibody cannot easily be used to treat human patients. Thus, there is a need for improved compositions that will bind c-Met, and that can be used, e.g., to inhibit HGF- and c-Met-dependent tumor growth by inhibiting mitogenesis, invasion, metastasis, and/or survival.

SUMMARY OF THE INVENTION

The present invention provides an isolated antibody or antigen-binding portion thereof that specifically binds c-Met and acts predominantly as a c-Met antagonist, and, in some instances, as a c-Met agonist antibody and compositions comprising said antibody or portion.

The invention provides a composition comprising the heavy and/or light chain, the variable domains thereof, or antigen-binding portions thereof an anti-c-Met antibody, or nucleic acid molecules encoding an antibody, antibody chain or variable domain thereof of the invention and a pharmaceutically acceptable carrier. Compositions of the invention may further comprise another component, such as a therapeutic agent or a diagnostic agent. Diagnostic and therapeutic methods are also provided by the invention.

The invention further provides an isolated cell line, that produces an anti-c-Met antibody or antigen-binding portion thereof.

The invention also provides nucleic acid molecules encoding the heavy and/or light chain of an anti-c-Met antibody, the variable domains thereof or antigen-binding portions thereof.

The invention provides vectors and host cells comprising the nucleic acid molecules, as well as methods of recombinantly producing the polypeptides encoded by the nucleic acid molecules.

Non-human transgenic animals or plants that express the heavy and/or light chain, or antigen-binding portions thereof, of an anti-c-Met antibody are also provided.

BRIEF DESCRIPTION OF THE DRAWINGS

FIG. 1A is a graph illustrating inhibition of ligand binding with anti-c-Met monoclonal antibodies of the invention. Anti-c-Met monoclonal antibodies 13.3.2L-A91T, H-E42K, S97T and 13.3.2 bind to the c-Met receptor and inhibit HGF binding.

FIG. 1B is a graph illustrating inhibition in a c-Met phosphorylation ELISA. Anti-c-Met monoclonal antibodies 13.3.2L-A91T, H-E42K, S97T and 13.3.2 inhibit c-Met tyrosine phosphorylation, as measured by a c-Met phosphorylation ELISA, in cells after stimulation with HGF.

FIG. 3A-3H are sequence alignments of the predicted amino acid sequences of light and heavy chain variable domains from four anti-c-Met antibodies compared with the germline amino acid sequences of the corresponding human genes. Differences between the antibody sequences and the germline sequence are indicated by shading of the antibody sequences. The underlined sequences in each alignment represent, from left to right, the germline signal peptide, CDR1, CDR2, and CDR3 sequences.

FIG. 3A shows an alignment of the predicted amino acid sequence of the light chain for antibody 13.3.2 (SEQ ID NO: 4, wherein $X_8$ is alanine) and the 13.3.2L-A91T (SEQ ID NO: 4, wherein $X_8$ is threonine) variant to the germline L5Vκ1, Jκ4 sequence (SEQ ID NO: 17).

FIG. 3B shows an alignment of the predicted amino acid sequence of the light chain for antibody 9.1.2 (SEQ ID NO: 8) to the germline A27Vκ3, Jκ2 sequence (SEQ ID NO: 18).

FIG. 3C shows an alignment of the predicted amino acid sequence of the light chain for antibody 8.70.2 (SEQ ID NO: 12) to the germline L5Vκ1, Jκ3 sequence (SEQ ID NO: 19).

FIG. 3D shows an alignment of the predicted amino acid sequence of the light chain for antibody 8.90.3 (SEQ ID NO: 16) to the germline L5Vκ1, Jκ1 sequence (SEQ ID NO: 20).

FIG. 3E shows an alignment of the predicted amino acid sequence of the heavy chain of antibody 13.3.2 (SEQ ID NO: 2, wherein $X_2$ is glutamate, $X_4$ is serine and $X_6$ is alanine); 13.3.2H-E42K (SEQ ID NO: 2, wherein $X_2$ is lysine, $X_4$ is serine and $X_6$ is alanine); 13.3.2H-E42K, S97T (SEQ ID NO: 2, wherein $X_2$ is lysine, $X_4$ is threonine and $X_6$ is alanine); 13.3.2H-A14P (SEQ ID NO: 2, wherein $X_2$ is glutamate, $X_4$ is serine and $X_6$ is proline); 13.3.2H-A14P, E42K (SEQ ID NO: 2, wherein $X_2$ is lysine, $X_4$ is serine and $X_6$ is proline); and 13.3.2H-A14P, E42K, S97T (SEQ ID NO: 2, wherein $X_2$ is lysine, $X_4$ is threonine and $X_6$ is proline) to the germline $V_H$1-18, D2-15, $J_H$4b sequence (SEQ ID NO: 21).

FIG. 3F shows an alignment of the predicted amino acid sequence of the heavy chain for antibody 9.1.2 (SEQ ID NO: 6) to the germline $V_H$ 4-31, D2-2, D7-27, $J_H$6b sequence (SEQ ID NO: 22).

FIG. 3G shows the alignment of the predicted amino acid sequence of the heavy chain for antibody 8.70.2 (SEQ ID NO: 10) to the germline $V_H$ 4-39, D2-2, $J_H$4b sequence (SEQ ID NO: 23).

FIG. 3H shows an alignment of the predicted amino acid sequence of the heavy chain for antibody 8.90.3 (SEQ ID NO: 14) to the germline $V_H$ 3-48, 4-17, $J_H$4b sequence (SEQ ID NO: 24).

FIG. 4A shows the results of an experiment demonstrating that anti-c-Met antibodies inhibit the growth of 3T3-S114 tumors.

FIG. 4B shows the results of an experiment demonstrating that anti-c-Met antibodies inhibit the growth of U87 tumors.

FIG. 4C shows the results of an experiment demonstrating that anti-c-Met antibodies inhibit the growth of A549 tumors.

FIG. 4D shows the results of an experiment demonstrating that anti-c-Met antibodies inhibit the growth of GTL-16 tumors.

FIG. 4E shows the results of an experiment demonstrating that anti-c-Met antibody 13.3.2L-A91T, H-E42K, S97T inhibits the growth of U87 tumors in a dose-dependent manner.

FIG. 5 also shows the relationship between anti-c-Met antibody 13.3.2L-A91T, H-E42K, S97T serum levels and c-Met downregulation in U87 tumors.

FIGS. 6A-6P are full length heavy and light chain nucleotide and predicted amino acid sequences from four anti-c-Met antibodies. The signal peptide for each heavy or light chain sequence is designated by underlined lower case type letters. The CDR1, CDR2 and CDR3 sequences for each heavy or light sequence are designated by underlined upper case type letters. The variable domain for each sequence are designated by upper case letters. The constant region for each sequence are designated by lower case type letters.

FIG. 6A shows the 13.3.2 Heavy Chain DNA sequence (SEQ ID NO: 1).

FIG. 6B shows the 13.3.2 Heavy Chain protein sequence (SEQ ID NO: 2).

FIG. 6C shows the 13.3.2 Light Chain [Kappa chain] DNA sequence (SEQ ID NO: 3).

FIG. 6D shows the 13.3.2 Light Chain [Kappa chain] protein sequence (SEQ ID NO: 4).

FIG. 6E shows the 9.1.2 Heavy Chain DNA sequence (SEQ ID NO: 5).

FIG. 6F shows the 9.1.2 Heavy Chain protein sequence (SEQ ID NO: 6).

FIG. 6G shows the 9.1.2 Light Chain [Kappa] DNA sequence (SEQ ID NO: 7).

FIG. 6H shows the 9.1.2 Light Chain [Kappa] protein sequence (SEQ ID NO: 8).

FIG. 6I shows the 8.70.2 Heavy Chain DNA sequence (SEQ ID NO: 9).

FIG. 6J shows the 8.70.2 Heavy Chain protein sequence (SEQ ID NO: 10).

FIG. 6K shows the 8.70.2 Light Chain [Kappa] DNA sequence (SEQ ID NO: 11).

FIG. 6L shows the 8.70.2 Light Chain [Kappa] protein sequence (SEQ ID NO: 12).

FIG. 6M shows the 8.90.3 Heavy Chain DNA sequence (SEQ ID NO: 13).

FIG. 6N shows the 8.90.3 Heavy Chain protein sequence (SEQ ID NO: 14).

FIG. 6O shows the 8.90.3 Light Chain [Kappa] DNA sequence (SEQ ID NO: 15).

FIG. 6P shows the 8.90.3 Light Chain [Kappa] protein sequence (SEQ ID NO: 16).

DETAILED DESCRIPTION OF THE INVENTION

Definitions and General Techniques

Figure 1A:
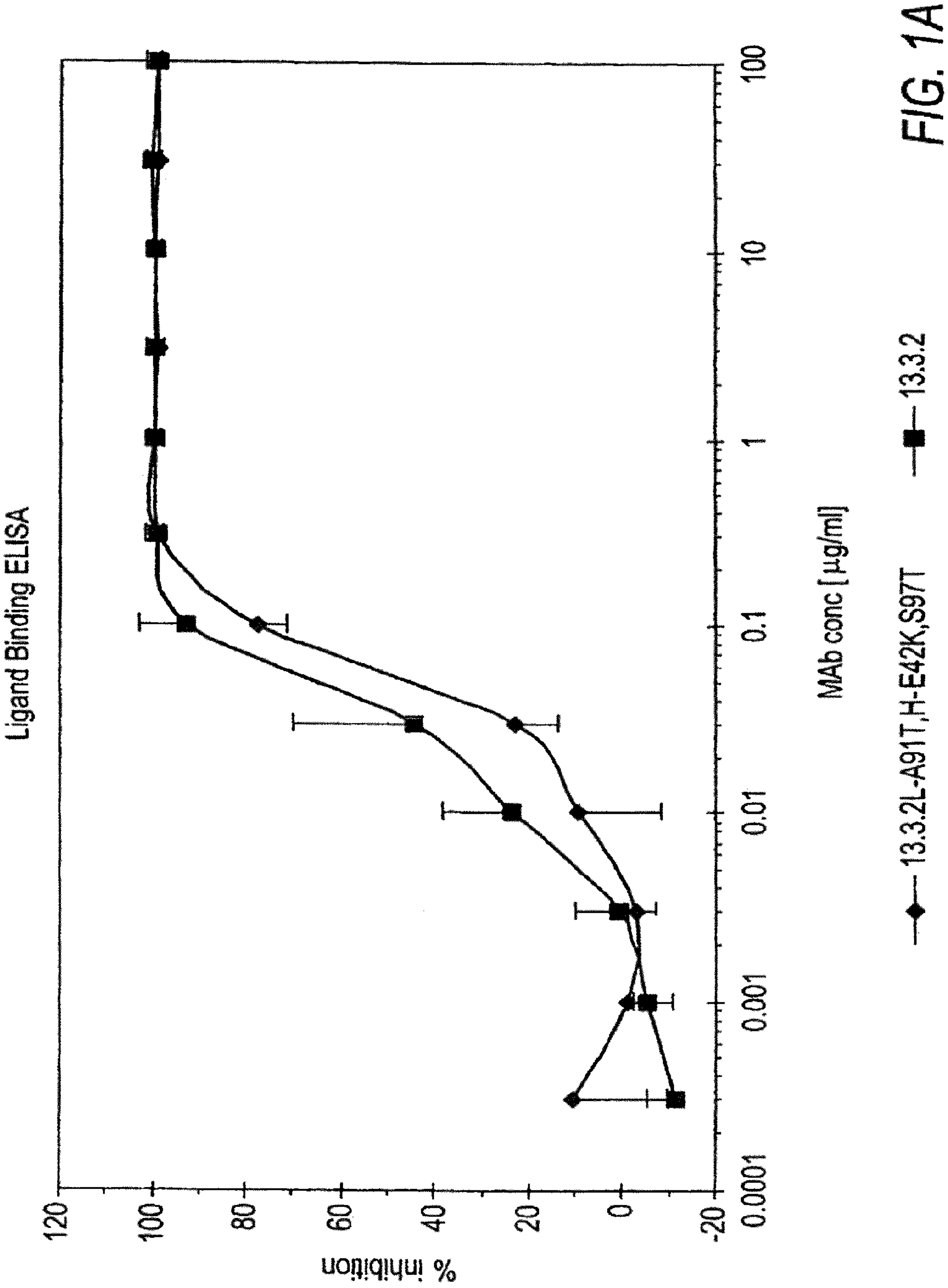
FIGS. 1A and 1B show that the anti-c-Met antibodies inhibit ligand binding to an isolated c-Met ECD/Fc protein and inhibits c-Met phosphorylation in cells after stimulation with HGF.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2nd ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane *Antibodies: A Laboratory Manual*, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include an anti-c-Met antibody that has been affinity purified using c-Met, an anti-c-Met antibody that has been synthesized by a hybridoma or other cell line in vitro, and a human anti-c-Met antibody derived from a transgenic mouse.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "polypeptide analog" as used herein refers to a polypeptide that comprises a segment that has substantial identity to a portion of an amino acid sequence and that has at least one of the following properties: (1) specific binding to c-Met under suitable binding conditions, (2) ability to inhibit or activate c-Met. Typically, polypeptide analogs comprise a conservative amino acid substitution (or insertion or deletion) with respect to the native sequence. Analogs typically are at least 20 or 25 amino acids long, preferably at least 50, 60, 70, 80, 90, 100, 150 or 200 amino acids long or longer, and can often be as long as a full-length polypeptide. Some embodiments of the invention include polypeptide fragments or polypeptide analog antibodies with 1, 2, 3, 4, 5, 6, 7, 8, 9, 10, 11, 12, 13, 14, 15, 16 or 17 substitutions from the germline amino acid sequence.

In certain embodiments, amino acid substitutions to an anti-c-Met antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to c-Met. Analogs can include various muteins of a sequence other than the normally-occurring peptide sequence. For example, single or multiple amino acid substitutions, preferably conservative amino acid substitutions, may be made in the normally-occurring sequence, preferably in the portion of the polypeptide outside the domain(s) forming intermolecular contacts. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al., *Nature* 354:105 (1991), incorporated herein by reference.

Non-peptide analogs are commonly used in the pharmaceutical industry as drugs with properties analogous to those of the template peptide. These types of non-peptide compound are termed "peptide mimetics" or "peptidomimetics." Fauchere, *J. Adv. Drug Res.* 15:29 (1986); Veber and Freidinger, *TINS* p. 392 (1985); and Evans et al., *J. Med. Chem.* 30:1229 (1987), incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference); for example, by adding internal cysteine residues capable of forming intramolecular disulfide bridges which cyclize the peptide.

Where an "antibody" is referred to herein with respect to the invention, it is normally understood that an antigen-binding portion thereof may also be used. An antigen-binding portion competes with the intact antibody for specific binding. See generally, *Fundamental Immunology*, Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', $F(ab')_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide.

From N-terminus to C-terminus, both the mature light and heavy chain variable domains comprise the regions FR1, CDR1, FR2, CDR2, FR3, CDR3 and FR4. The assignment of amino acids to each domain herein is in accordance with the definitions of Kabat, *Sequences of Proteins of Immunological Interest* (National Institutes of Health, Bethesda, Md. (1987 and 1991)), Chothia & Lesk, *J. Mol. Biol.* 196:901-917 (1987) or Chothia et al., *Nature* 342:878-883 (1989).

As used herein, an antibody that is referred to by number is the same as a monoclonal antibody that is obtained from the hybridoma of the same number. For example, monoclonal antibody 13.3.2 is the same antibody as one obtained from hybridoma 13.3.2, or a subclone thereof.

As used herein, a Fd fragment means an antibody fragment that consists of the $V_H$ and $C_H1$ domains; an Fv fragment consists of the $V_L$ and $V_H$ domains of a single arm of an antibody; and a dAb fragment (Ward et al., *Nature* 341:544-546 (1989)) consists of a $V_H$ domain.

In some embodiments, the antibody is a single-chain antibody (scFv) in which a $V_L$ and $V_H$ domains are paired to form a monovalent molecules via a synthetic linker that enables them to be made as a single protein chain. (Bird et al., *Science* 242:423-426 (1988) and Huston et al., *Proc. Natl. Acad. Sci. USA* 85:5879-5883 (1988).) In some embodiments, the antibodies are diabodies, i.e., are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites. (See e.g., Holliger P. et al., *Proc. Natl. Acad. Sci. USA* 90:6444-6448 (1993), and Poljak R. J. et al., *Structure* 2:1121-1123 (1994).) In some embodiments, one or more CDRs from an antibody of the invention may be incorporated into a molecule either covalently or noncovalently to make it an immunoadhesin that specifically binds to c-Met. In such embodiments, the CDR(s) may be incorporated as part of a larger polypeptide chain, may be covalently linked to another polypeptide chain, or may be incorporated noncovalently.

In embodiments having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies. In one embodiment, one or more of the CDRs of the chimeric antibody are derived from a human anti-c-Met antibody. In another embodiment, all of the CDRs are derived from a human anti-c-Met antibodies. In another embodiment, the CDRs from more than one human anti-c-Met antibodies are combined in a chimeric antibody. For instance, a chimeric antibody may comprise a CDR1 from the light chain of a first human anti-c-Met antibody, a CDR2 from the light chain of a second human anti-c-Met antibody and a CDR3 from the light chain of a third human anti-c-Met antibody, and CDRs from the heavy chain may be derived from one or more other anti-c-Met antibodies. Further, the framework regions may be derived from one of the anti-c-Met antibodies from which one or more of the CDRs are taken or from one or more different human antibodies.

In some embodiments, a chimeric antibody of the invention is a humanized anti-c-Met antibody. A humanized anti-c-Met antibody of the invention comprises the amino acid sequence of one or more framework regions and/or the amino acid sequence from at least a portion of the constant region of one or more human anti-c-Met antibodies of the invention and CDRs derived from a non-human anti-c-Met antibody.

An "activating antibody" (also referred to herein as an "agonist antibody" as used herein means an antibody that increases one or more c-Met activities by at least about 40% when added to a cell, tissue or organism expressing c-Met. In some embodiments, the antibody activates c-Met activity by at least 50%, 60%, 70%, 80%, 85%, 90%, 95%, 100% or greater than 100%. In some embodiments, the activating antibody is added in the presence of HGF. In some embodiments, an agonist antibody of the invention increases at least one activity of c-Met by 10-fold.

Fragments or analogs of antibodies or immunoglobulin molecules can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. See Bowie et al., *Science* 253:164 (1991).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., *Ann. Biol. Clin.* 51:19-26 (1993); Jonsson U. et al., *Biotechniques* 11:620-627 (1991); Jonsson B. et al., *J. Mol. Recognit.* 8:125-131 (1995); and Johnsson B. et al., *Anal. Biochem.* 198:268-277 (1991).

The term "$K_D$" refers to the equilibrium dissociation constant of a particular antibody-antigen interaction.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearally along the primary amino acid sequence of the protein. In a conformational epitope, the points of interaction occur across amino acid residues on the protein that are separated from one another. An antibody is said to specifically bind an antigen when the dissociation constant is ≤1 mM, preferably ≤100 nM and most preferably ≤10 nM. In certain embodiments, the $K_D$ is 1 pM to 500 pM. In other embodiments, the $K_D$ is between 500 pM to 1 μM. In other embodiments, the $K_D$ is between 1 μM to 100 nM. In other embodiments, the $K_D$ is between 100 mM to 10 nM. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 03/48731.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of a polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoranil-adate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked.

Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. One example of "high stringency" or "highly stringent" conditions is the incubation of a polynucleotide with another polynucleotide, wherein one polynucleotide may be affixed to a solid surface such as a membrane, in a hybridization buffer of 6×SSPE or SSC, 50% formamide, 5× Denhardt's reagent, 0.5% SDS, 100 μg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183:63-98 (1990); Pearson, *Methods Mol. Biol.* 132:185-219 (2000); Pearson, *Methods Enzymol.* 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

As used herein, the terms "percent sequence identity" and "percent sequence homology" are used interchangeably.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.* 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and a mutein thereof. See, e.g., GCG Version 6.1 (University of Wisconsin, WI). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul et al., *J. Mol. Biol.* 215:403-410 (1990); Altschul et al., *Nucleic Acids Res.* 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

Throughout this specification and claims, the word "comprise," or variations such as "comprises" or "comprising," will be understood to imply the inclusion of a stated integer or group of integers but not the exclusion of any other integer or group of integers.

Human Anti-c-Met Antibodies and Characterization Thereof

In one embodiment, the invention provides humanized anti-c-Met antibodies. In another embodiment, the invention provides human anti-c-Met antibodies. In some embodiments, human anti-c-Met antibodies are produced by immunizing a non-human transgenic animal, e.g., a rodent, whose genome comprises human immunoglobulin genes so that the transgenic animal produces human antibodies.

An anti-c-Met antibody of the invention can comprise a human kappa or a human lambda light chain or an amino acid sequence derived therefrom. In some embodiments comprising a kappa light chain, the light chain variable domain ($V_L$) is encoded in part by a human L5 $V_{\kappa 1}$ or A27 $V_{\kappa 3}$ gene.

In some embodiments, the $V_L$ of the c-Met antibody comprises one or more amino acid substitutions relative to the germline amino acid sequence. In some embodiments, the $V_L$ of the anti-c-Met antibody comprises 1, 2, 3, 4, 5, 6, 7, 8, 9, or 10 amino acid substitutions relative to the germline amino acid sequence. In some embodiments, one or more of those substitutions from germline is in the CDR regions of the light chain. In some embodiments, the amino acid substitutions relative to germline are at one or more of the same positions as the substitutions relative to germline in any one or more of the $V_L$ of antibodies 13.3.2; 9.1.2; 8.70.2; 8.90.3 or 13.3.2L-A91T. For example, the $V_L$ of the anti-c-Met antibody may contain one or more amino acid substitutions compared to germline found in the $V_L$ of antibody 9.1.2. or there may be one or more amino acid substitutions compared to germline found in the $V_L$ of antibody 13.3.2, which utilizes the same $V_K$ gene as antibody 8.70.2. In some embodiments, the amino acid changes are at one or more of the same positions, but involve a different substitution than in the reference antibody.

In some embodiments, amino acid changes relative to germline occur at one or more of the same positions as in any of the $V_L$ of antibodies 13.3.2; 9.1.2; 8.70.2; 8.90.3 or 13.3.2L-A91T, but the changes may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline is serine, one may conservatively substitute threonine for serine at that position. Conservative amino acid substitutions are discussed supra.

In some embodiments, the light chain of the human anti-c-Met antibody comprises the $V_L$ amino acid sequence of antibody 13.3.2 (SEQ ID NO: 4, wherein $X_8$ is alanine); 13.3.2L-A91T (SEQ ID NO: 4, wherein $X_8$ is threonine); 9.1.2 (SEQ ID NO: 8); 8.70.2 (SEQ ID NO: 12); or 8.90.3 (SEQ ID NO: 16) or said amino acid sequence having up to 1, 2, 3, 4, 5, 6, 7, 8, 9, or 10 conservative amino acid substitutions and/or a total of up to 3 non-conservative amino acid substitutions. In some embodiments, the light chain comprises the amino acid sequence from the beginning of the CDR1 to the end of the CDR3 of any one of the foregoing antibodies.

In some embodiments, the light chain may comprise CDR1, CDR2 and CDR3 regions independently selected from the light chain CDR1, CDR2 and CDR3, respectively of the light chain antibody 13.3.2; 9.1.2; 8.70.2; 8.90.3 or 13.3.2L-A91T, or CDR regions each having less than 4 or less than 3 conservative amino acid substitutions and/or a total of three or fewer non-conservative amino acid substitutions. In some embodiments, the light chain of the anti-c-Met antibody comprises a light chain CDR1, CDR2, and CDR3, each of which are independently selected from the light chain CDR1, CDR2 and CDR3 regions of monoclonal antibody 13.3.2 (SEQ ID NO: 4, wherein $X_8$ is alanine; SEQ ID NO: 3 wherein $X_7$ is guanosine); 13.3.2L-A91T (SEQ ID NO: 4, wherein $X_8$ is threonine; SEQ ID NO: 3, wherein $X_7$ is adenosine); 9.1.2. (SEQ ID NO: 8; SEQ ID NO: 7); 8.70.2 (SEQ ID NO: 12; SEQ ID NO: 11); or 8.90.3 (SEQ ID NO: 16; SEQ ID NO: 15). In certain embodiments, the light chain of the anti-c-Met antibody comprises the light chain CDR1, CDR2 and CDR3 regions of an antibody comprising the amino acid sequence of the $V_L$ region of an antibody selected from 13.3.2 (SEQ ID NO: 4, wherein $X_8$ is alanine); 9.1.2. (SEQ ID NO: 8); 8.70.2 (SEQ ID NO: 12); 8.90.3 (SEQ ID NO: 16) or 13.3.2L-A91T (SEQ ID NO: 4, wherein $X_8$ is threonine) or said CDR regions each having less than 4 or less than 3 conservative amino acid substitutions and/or a total of three or fewer non-conservative amino acid substitutions.

With regard to the heavy chain, in some embodiments, the variable domain ($V_H$) is encoded in part by a human $V_H$1-18, $V_H$4-31, $V_H$4-39, or $V_H$3-48 gene. In some embodiments, the $V_H$ sequence of the anti-c-Met antibody contains one or more amino acid substitutions, deletions or insertions (additions) relative to the germline amino acid sequence. In some embodiments, the variable domain of the heavy chain comprises 1, 2, 3, 4, 5, 6, 7, 8, 9, 10, 11, 12, 13, 14, 15, 16, or 17 mutations from the germline amino acid sequence. In some embodiments, the mutation(s) are non-conservative substitutions compared to the germline amino acid sequence. In some embodiments, the mutations are in the CDR regions of the heavy chain. In some embodiments, the amino acid changes are made at one or more of the same positions as the mutations from germline in any one or more of the $V_H$ of antibodies 13.3.2; 9.1.2; 8.70.2; 8.90.3; 13.3.2H-A14P; 13.3.2H-E42K; 13.3.2H-S97T; 13.3.214-A14P, E42K; 13.3.2H-E42K, S97T; or 13.3.2H-A14P, E42K, S97T. In other embodiments, the amino acid changes are at one or more of the same positions but involve a different mutation than in the reference antibody.

In some embodiments, the heavy chain comprises the $V_H$ amino acid sequence of antibody 13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine); 9.1.2 (SEQ ID NO: 6); 8.70.2 (SEQ ID NO: 10) or 8.90.3 (SEQ ID NO: 14); or said $V_H$ amino acid sequence having up to 1, 2, 3, 4, 6, 8, or 10 conservative amino acid substitutions and/or a total of up to 3 non-conservative amino acid substitutions. In some embodiments, the heavy chain comprises the amino acid sequence from the beginning of the CDR1 to the end of the CDR3 of any one of the foregoing antibodies.

In some embodiments, the heavy chain comprises the heavy chain CDR1, CDR2 and CDR3 regions of antibody 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T; or 13.3.2H-A14P, E42K, S97T or said CDR regions each having less than 8, less than 6, less than 4, or less than 3 conservative amino acid substitutions and/or a total of three or fewer non-conservative amino acid substitutions.

In some embodiments, the heavy chain CDR regions are independently selected from the CDR regions of two or more antibodies of 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T or 13.3.2H-A14P, E42K, S97T. In another embodiment, the heavy chain comprises CDR regions independently selected from two or more $V_H$ regions selected from 13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine); 9.1.2 (SEQ ID NO: 6); 8.70.2 (SEQ ID NO: 10) or 8.90.3 (SEQ ID NO: 14). In another embodiment, the antibody comprises a light chain as disclosed above and a heavy chain as disclosed above. In a further embodiment, the light chain CDRs and the heavy chain CDRs are from the same antibody.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to change any potential proteolytic sites in the antibody. Such sites may occur in a CDR or framework region of a variable domain or in the constant domain of an antibody. Substitution of cysteine residues and removal of proteolytic sites may decrease the risk of any heterogeneity in the antibody product and thus increase its homogeneity. Another type of amino acid substitution is to eliminate asparagine-glycine pairs, which form potential deamidation sites, by altering one or both of the residues.

In some embodiments, the C-terminal lysine of the heavy chain of the anti c-Met antibody of the invention is cleaved. In various embodiments of the invention, the heavy and light chains of the anti-c-Met antibodies may optionally include a signal sequence.

In one aspect, the invention relates to four inhibitory human anti-c-Met monoclonal antibodies and the hybridoma cell lines that produce them. Table 1 lists the sequence identifiers (SEQ ID NOs:) of the nucleic acids encoding the full-length heavy and light chains (including leader sequence), and the corresponding full-length deduced amino acid sequences.

TABLE 1

HUMAN ANTI-c-Met ANTIBODIES

| Monoclonal Antibody | SEQUENCE IDENTIFIER (SEQ ID NO:) Full Length — Heavy DNA | Heavy Protein | Light DNA | Light Protein |
|---|---|---|---|---|
| 13.3.2 | 1 | 2 | 3 | 4 |
| 9.1.2 | 5 | 6 | 7 | 8 |
| 8.70.2 | 9 | 10 | 11 | 12 |
| 8.90.3 | 13 | 14 | 15 | 16 |

The invention further provides heavy and/or light chain variants of certain of the above-listed human anti-c-Met antibodies, comprising one or more amino acid substitutions. To designate the variants, the first letter is the one letter symbol for the amino acid of the naturally-occurring antibody chain, the number refers to the position of the amino acid (wherein position one is the N-terminal amino acid), and the second letter is the one letter symbol for the variant amino acid. In some embodiments, the invention provides heavy chain variant of monoclonal antibody 13.3.2. One 13.3.2 heavy chain variant is E42K, which has a lysine at position $X_2$ of SEQ ID NO: 2. The DNA sequence encoding the E42K 13.3.2 variant has an adenosine at $X_1$ of SEQ ID NO: 1.

A second 13.3.2 heavy chain variant is S97T, which has a threonine residue at position $X_4$. The DNA sequence encoding the S97T 13.3.2 variant has an adenosine at $X_3$ of SEQ ID NO: 1. A third 13.3.2 heavy chain variant is A14P, which has a proline residue at $X_6$ of SEQ ID NO: 2. In the DNA sequence, the A14P 13.3.2 variant is encoded by SEQ ID NO:1, in which $X_5$ is an cytosine. The invention also provides a variant light chain of monoclonal antibody 13.3.2. A91T is 13.3.2 light chain variant, represented by SEQ ID NO: 4, in which $X_8$ is a threonine residue. In the DNA sequence, the A91T 13.3.2 variant is encoded by SEQ ID NO: 3, in which $X_7$ is an adenosine. Antibodies comprising a variant heavy or light chain and a wild type chain, are designated by the variant chain. Thus, an antibody containing a wild type light chain of antibody 13.3.2 and the E42K heavy chain variant is designated as 13.3.2H-E42K.

In other embodiments of the invention, antibodies containing combinations of amino acid variants can be produced, e.g., 13.3.2H-E42K, S97T. Further combinations of a variant heavy chain and the variant light chain of 13.3.2 are included. In a preferred embodiment, the anti-c-Met antibody is 13.3.2; 9.1.2; 8.70.2; 8.90.3; 13.3.2H-A14P; 13.3.2H-E42K; 13.3.2H-A14P, E42K; 13.3.2H-E42K, S97T; 13.3.2H-A14P, E42K, S97T; 13.3.2H-S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T. In still further embodiments, the invention includes antibodies comprising variable domain amino acid sequences with more than 80%, more than 85%, more than 90%, more than 95%, more than 96%, more than 97%, more than 98% or more than 99% sequence identity to an variable domain amino acid sequence of any of the above-listed human anti-c-Met antibodies.

Class and Subclass of Anti-c-Met Antibodies

The class and subclass of anti-c-Met antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In some embodiments, the anti-c-Met antibody is a monoclonal antibody. The anti-c-Met antibody can be an IgG, an IgM, an IgE, an IgA, or an IgD molecule. In a preferred embodiment, the anti-c-Met antibody is an IgG and is an IgG1, IgG2, IgG3, IgG4 subclass. In another preferred embodiment, the antibody is subclass IgG2.

Binding Affinity of Anti-c-Met Antibodies to c-Met

In some embodiments of the invention, the anti-c-Met antibodies bind to c-Met with high affinity. In some embodiments, the anti-c-Met antibody binds to c-Met with a $K_D$ of $2\times10^{-7}$M or less. In other preferred embodiments, the antibody binds to c-Met with a $K_D$ of $2\times10^{-8}$ M, $2\times10^{-9}$ M, or $5\times10^{-10}$ M or less. In an even more preferred embodiment, the antibody binds to c-Met with substantially the same $K_D$ as an antibody selected from 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T; 13.3.2H-A14P, E42K, S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T. In still another preferred embodiment, the antibody binds to c-Met with substantially the same $K_D$ as an antibody that comprises a heavy chain variable domain having the amino acid sequence of a $V_H$ region of SEQ ID NO: 2 [13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine)], 6, 10, or 14, a light chain variable domain having the amino acid sequence of a $V_L$ region of SEQ ID NO: 4 [13.3.2 (SEQ ID NO: 4, wherein $X_8$ is alanine); 13.3.2L-A91T (SEQ ID NO: 4, wherein $X_8$ is threonine)], 8, 12, or 16 or both. In another preferred embodiment, the antibody binds to c-Met with substantially the same $K_D$ as an antibody that comprises the CDR regions of a light chain variable domain having the amino acid sequence of a $V_L$ region of SEQ ID NO: 4 [13.3.2 (SEQ ID NO: 4, wherein $X_8$ is alanine); 13.3.2L-A91T (SEQ ID NO: 4, wherein $X_8$ is threonine)], 8, 12, or 16 or that comprises the CDR regions of a heavy chain variable domain having the amino acid sequence a $V_H$ region of SEQ ID NO: 2 [13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine)], 6, 10, or 14.

In some embodiments, the anti-c-Met antibody has a low dissociation rate constant ($k_{off}$) In some embodiments, the anti-c-Met antibody has a $k_{off}$ of $1.0\times10^{-3}$ s−1 or lower or a $k_{off}$ of $5.0\times10^{-4}$ $s^{-1}$ or lower. In other preferred embodiments, the antibody binds to c-Met with a $k_{off}$ of $2\times10^{4}$ $s^{-1}$ or lower. In some embodiments, the $k_{off}$ is substantially the same as an antibody described herein, including an antibody selected from 13.3.2; 9.1.2; 8.70.2; 8.90.3; 13.3.2H-A14P; 13.3.2H-S97T; 13.3.2H-E42K; 13.3.2H-A14P, E42K; 13.3.2H-E42K, S97T; 13.3.2H-A14P, E42K, S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T. In some embodiments, the antibody binds to c-Met with substantially the same $k_{off}$ as an antibody that comprises the CDR regions of a heavy chain; or the CDR regions of a light chain from an antibody selected from 13.3.2; 9.1.2; 8.70.2; 8.90.3 or 13.3.2L-A91T. In some embodiments, the antibody binds to c-Met with substantially the same $k_{off}$ as an antibody that comprises a heavy chain variable domain having the amino acid sequence of a $V_H$ region of SEQ ID NO: 2 [13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine)], 6, 10, or 14, a light chain variable domain having the amino acid sequence of a $V_L$ region of SEQ ID NO: 4 [13.3.2 (SEQ ID NO: 4, wherein $X_8$ is alanine); 13.3.2L-A91T (SEQ ID NO: 4, wherein $X_8$ is threonine)], 8, 12, or 16 or both. In another preferred embodiment, the antibody binds to c-Met with substantially the same $k_{off}$ as an antibody that comprises the CDR regions of a light chain variable domain having the amino acid sequence of a $V_L$ region of SEQ ID NO: 4 [13.3.2 (SEQ ID NO: 4, wherein $X_8$ is alanine) and the 13.3.2L-A91T (SEQ ID NO: 4, wherein $X_8$ is threonine)], 8, 12, or 16; or the CDR regions of a heavy chain variable domain having the amino acid sequence of a $V_H$ region of SEQ ID NO: 2 [13.3.2 (SEQ ID NO: 2, wherein $X_2$ is glutamate, $X_4$ is serine); 13.3.2H-E42K (SEQ ID NO: 2, wherein $X_2$ is lysine, $X_4$ is serine); 13.3.2H-E42K, S97T (SEQ ID NO: 2, wherein $X_2$ is lysine, $X_4$ is threonine)], 6, 10, or 14.

The binding affinity and dissociation rate of an anti-c-Met antibody to c-Met can be determined by methods known in the art. The binding affinity can be measured by ELISAs, RIAs, flow cytometry, surface plasmon resonance, such as BIACORE™. The dissociate rate can be measured by surface plasmon resonance. Preferably, the binding affinity and dissociation rate is measured by surface plasmon resonance. More preferably, the binding affinity and dissociation rate are measured using BIACORE™. One can determine whether an antibody has substantially the same $K_D$ as an anti-c-Met antibody by using methods known in the art. Example VIII exemplifies a method for determining affinity constants of anti-c-Met monoclonal antibodies by BIACORE™.

Identification of c-Met Epitopes Recognized by Anti-c-Met Antibodies

The invention provides a human anti-c-Met monoclonal antibody that binds to c-Met and competes or cross-competes with and/or binds the same epitope as: (a) an antibody selected from 13.3.2; 9.1.2; 8.70.2; 8.90.3; 13.3.2H-A14P; 13.3.2H-E42K; 13.3.2H-A14P, E42K; 13.3.2H-E42K, S97T; 13.3.2H-A14P, E42K, S97T; 13.3.2H-S97T; 13.3.2L-A91 T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T; (b) an antibody that comprises a heavy chain variable domain having an amino acid sequence of SEQ ID NO: 2, 6, 10 or 14, (c) an antibody that comprises a light chain variable domain having an amino acid sequence of SEQ ID NO: 4, 8, 12, or 16, or (d) an antibody that comprises both a heavy chain variable domain as defined in (b) and a light chain variable domain as defined in (c).

One can determine whether an antibody binds to the same epitope or cross competes for binding with an anti-c-Met antibody by using methods known in the art. In one embodiment, one allows the anti-c-Met antibody of the invention to bind to c-Met under saturating conditions and then measures the ability of the test antibody to bind to c-Met. If the test antibody is able to bind to c-Met at the same time as the anti-c-Met antibody, then the test antibody binds to a different epitope as the anti-c-Met antibody. However, if the test antibody is not able to bind to c-Met at the same time, then the test antibody binds to the same epitope, an overlapping epitope, or an epitope that is in close proximity to the epitope bound by the human anti-c-Met antibody. This experiment can be performed using ELISA, RIA, BIACORE™, or flow cytometry. In a preferred embodiment, the experiment is performed using ELISA. Methods of determining $K_D$ are discussed further below.

Inhibition of c-Met Activity by Anti-c-Met Antibody

In another embodiment, the invention provides an anti-c-Met antibody that inhibits the binding of HGF to the c-Met receptor. In a preferred embodiment, the c-Met receptor is human. In another preferred embodiment, the anti-c-Met antibody is a human antibody. The $IC_{50}$ can be measured in a ligand binding assay by ELISA, RIA, or other assays and cell-based assays such as scattering assay, soft agar growth and tubulomorphogenesis assay. In one embodiment, the antibody or portion thereof inhibits ligand binding between HGF and c-Met with an $IC_{50}$ of no more than 5 μg/ml, preferably no more than 1 μg/ml, more preferably than 0.5 μg/ml, even more preferably no more than 0.20 μg/ml as measured by an ELISA assay. (See FIG. 1A) Example III exemplifies this type of assay.

Figure 1B:
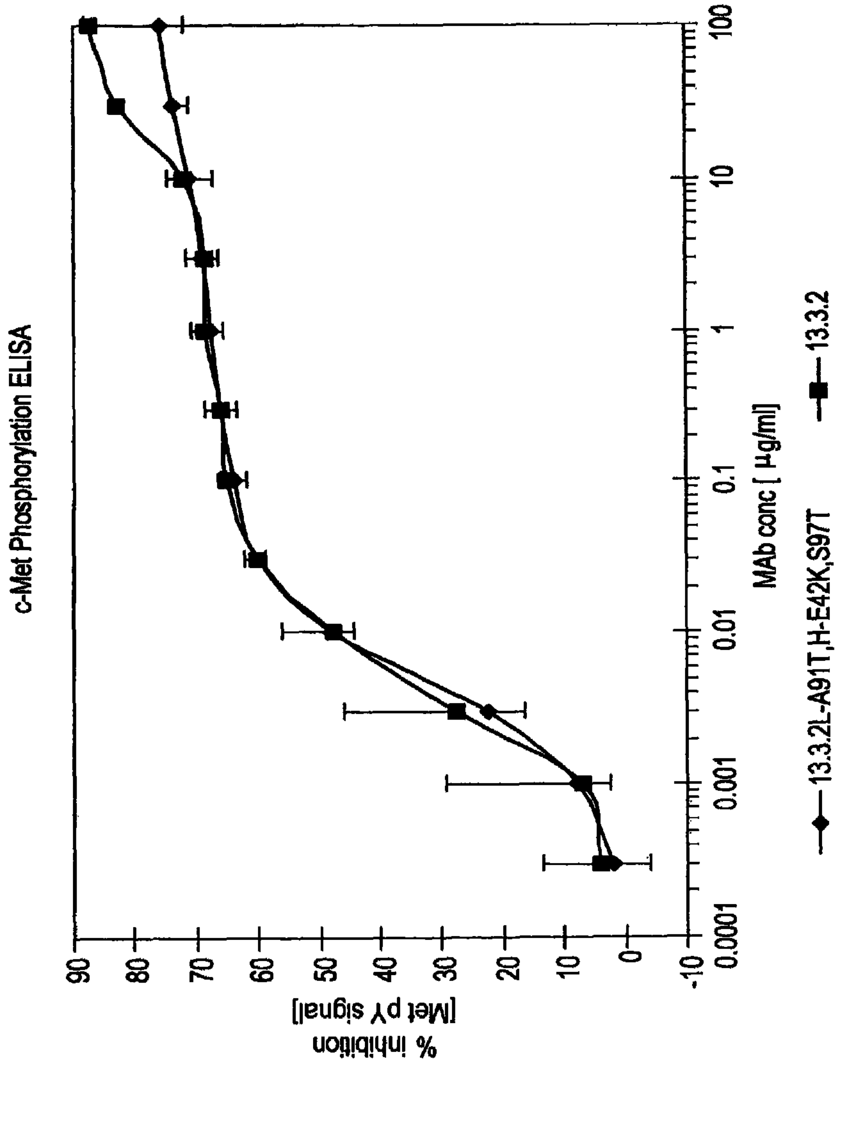

In another embodiment, the invention provides an anti-c-Met antibody that prevents activation of c-Met in the presence of HGF. In a preferred embodiment, the anti-c-Met antibody inhibits HGF-induced tyrosine phosphorylation that occurs upon binding to c-Met. One can determine whether an anti-c-Met antibody can prevent activation of c-Met in the presence of HGF by determining the levels of autophosphorylation for c-Met by Western blotting or an ELISA assay. In a preferred embodiment, one would determine the levels of autophosphorylation of c-Met using an ELISA assay. In another preferred embodiment, the $IC_{50}$, measured using an ELISA assay, is no more than 5 μg/ml, preferably no more than 1 μg/ml, more preferably than 0.5 μg/ml, even more preferably no more than 0.20 μg/ml. Example IV exemplifies one type of assay that measures inhibition of c-Met activation by an anti-c-Met antibody in the presence of HGF (See FIG. 1B).

In another aspect of the invention, the antibody may cause a downregulation of cell surface c-Met levels after an incubation with the antibody. In some embodiments, the incubation can be a short time period (e.g., 4 hours) or a longer time period (e.g., 24 hours). A downregulation of cell surface c-Met levels can be measured using western blotting or ELISA. In particular embodiments of the invention, the antibody may cause preferably a 6% downregulation of cell surface c-Met levels, preferably a 10% downregulation, or more preferably a 20% downregulation, more preferably a 50% downregulation or even more preferably at least 50% downregulation of cell surface c-Met levels as measured by western blotting or ELISA. Example V exemplifies one type of an ELISA measuring downregulation of cell surface c-Met levels after a short incubation with the antibody.

In another embodiment, the invention provides an anti-c-Met antibody that inhibits colony formation in soft agar. In various embodiments, the $IC_{50}$, as measured by a soft agar growth assay, is no more than 25 μg/ml, preferably no more than 20 μg/ml, more preferably no more than 5 μg/ml, even more preferably no more than 1 μg/ml. In another embodiment, a tubular morphogenesis assay can be used to measure the percent of inhibition of c-Met dependent morphological changes in cells grown in the presence of HGF and treated with antibodies of the invention. Preferably, the percent of inhibition measured with the tubular morphogenesis assay is no less than 20%, preferably no less than 60%, or even more preferably is no less than 80%. Examples VI and VII exemplify various types of assays.

Inhibition of Tumor Cell Growth In Vivo with Anti-c-Met Antibodies

According to some embodiments, the invention provides an anti-c-Met antibody that inhibits the proliferation of tumor cells in vivo. The tumor cell may be derived from any cell type including, without limitation, epidermal, epithelial, endothelial or mesodermal cells. The tumor cells may be derived from solid or non-solid tumors including, but not limited to, leukemia, sarcoma, multiple myeloma, glioblastoma, choriocarcinoma, Kaposi or cervical intraepithelial neoplasia. In another embodiment, the anti-c-Met antibody inhibits prostate, colon, breast, ovarian, gastric, lung and glioblastoma tumor growth in an animal. Examples of cells that the c-Met antibodies inhibit S114, an NIH-3T3 cell line engineered to express human HGF and human c-Met (Rong et al., *Mol. Cell. Biol.,* 12(11):5152-5158; (1992); U.S. Pat. No. 4,405,712). In some embodiments, an anti-c-Met antibody of the invention is used to treat lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

In a preferred embodiment, the antibody inhibits tumor cell growth as compared to the growth of the tumor in an untreated animal. In a more preferred embodiment, the anti-c-Met antibody inhibits tumor cell growth by at least 30%, 35%, 40%, 45%, 50%, 55%, 60%, 65%, 70%, 75%, 80%, 85%, 90%, 95% or 100%. In one embodiment, the inhibition of tumor cell growth is measured at least 7 days after the animals have started treatment with the antibody. In another embodiment, the inhibition of tumor cell growth is measured at least 14 days after the animals have started treatment with the antibody. See Example IX. In another embodiment, the anti-c-Met antibody result in tumor regression of at least 10% to 100%.

Activation of c-Met by Anti-c-Met Antibody

Another aspect of the present invention involves an anti-c-Met antibody that is an activating antibody, i.e., a c-Met agonist. An activating antibody amplifies or substitutes for the effects of HGF on c-Met. In some embodiments, the activating antibody is essentially a mimic of HGF, and competes with HGF for binding to c-Met. In some embodiments, the antibody does not compete with HGF for binding to c-Met, but amplifies the effect of HGF binding to c-Met. In some embodiments, the anti-c-Met antibody activates c-Met in the presence or absence of HGF. The anti-c-Met antibody agonist activity can be measured using a c-Met activation ELISA assay. In some embodiments of the invention, agonist activity is 2 to 3-fold stimulation over cells not stimulated with HGF. In other embodiments, the agonist activity is at least 6-fold. Example X describes an example a of c-Met activation assay. The anti-c-Met antibody agonist activity can be measured using a tubular morphogenesis assay. In one embodiment of the invention, weak agonist activity may be measured by using a tubular morphogenesis assay that measures c-Met agonist activity. Example X exemplifies one type of a tubular morphogenesis assay that measures c-Met agonist activity.

Species and Molecular Selectivity

In another aspect of the invention, the anti-c-Met antibodies demonstrate both species and molecular selectivity. In some embodiments, the anti-c-Met antibody binds to human and cynomologus and rhesus monkey c-Met. In another embodiment, the anti-c-Met antibody additionally binds to rat c-Met. In another embodiment, the anti-c-Met antibody does not bind to mouse or dog c-Met. Following the teachings of the specification, one may determine the species selectivity for the anti-c-Met antibody using methods well known in the art. For instance, one may determine the species selectivity using Western blot, flow cytometry, ELISA, immunoprecipitation or MA. In a preferred embodiment, one may determine the species selectivity using flow cytometry.

Figure 2:
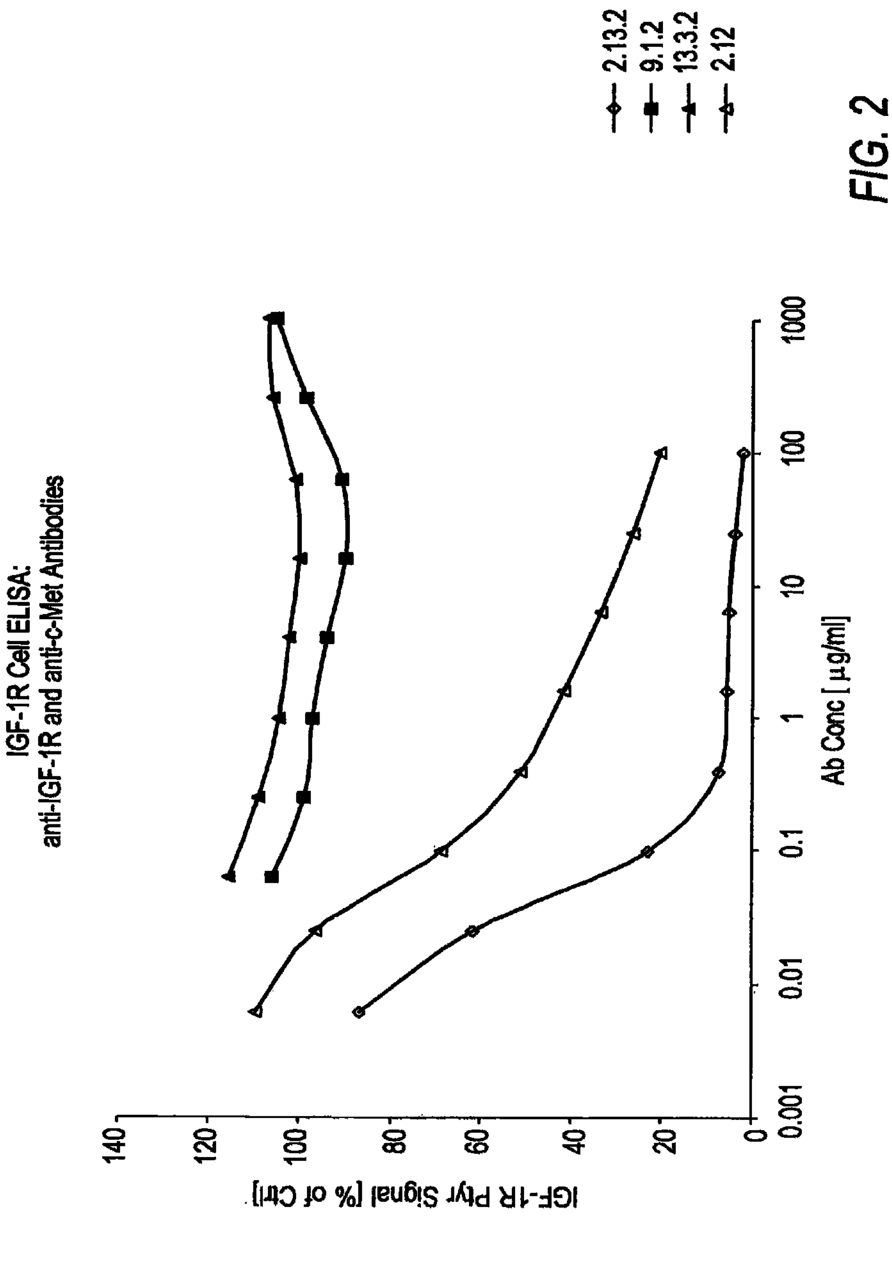
FIG. 2 is a graph illustrating anti-c-Met monoclonal antibody specificity. Anti-IGF-1R monoclonal antibodies 2.13.2 and 2.12.1 bind to IGF-1R and cause a decrease in tyrosine phosphorylation of the IGF-1R following treatment with IGF-1. Anti-c-Met antibodies 9.1.2 and 13.3.2 do not bind to IGF-IR, even at high concentrations of antibody, and do not cause a decrease in tyrosine phosphorylation of the IGF-1R.
Figure 4B:
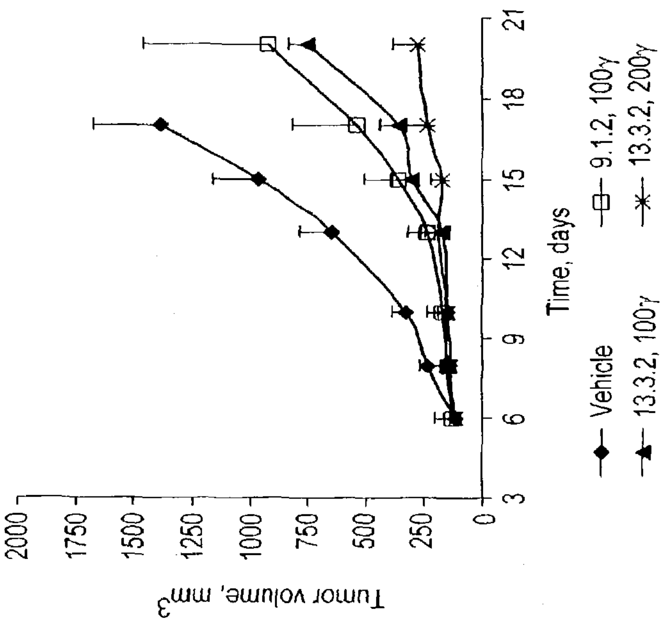
FIG. 4A-4E show that anti-c-Met antibodies inhibit tumor growth in vivo. The arrows along the x-axis represent anti-c-Met antibody doses administered.
Figure 4A:
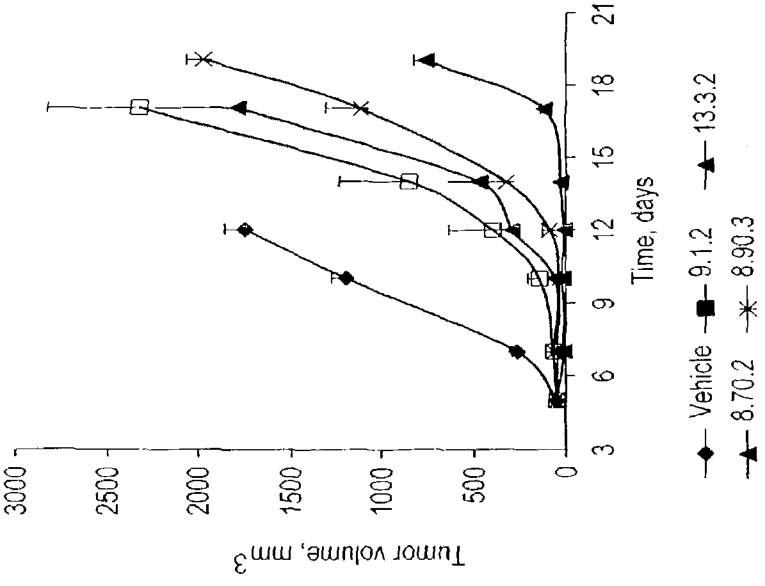
Figure 4C:
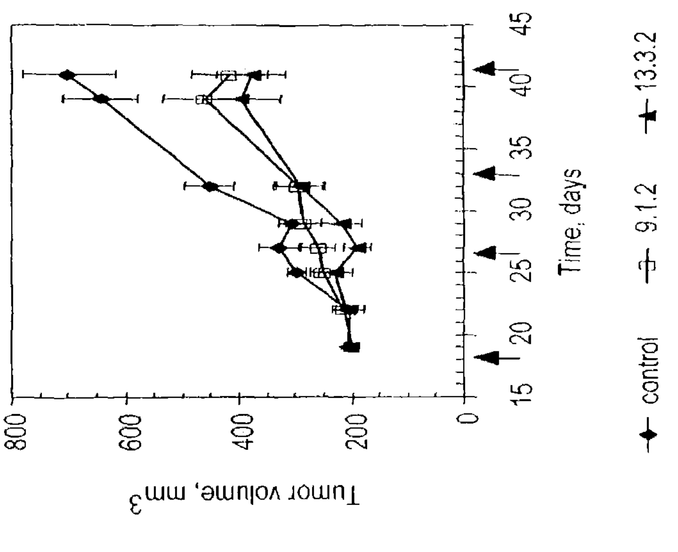
Figure 4D:
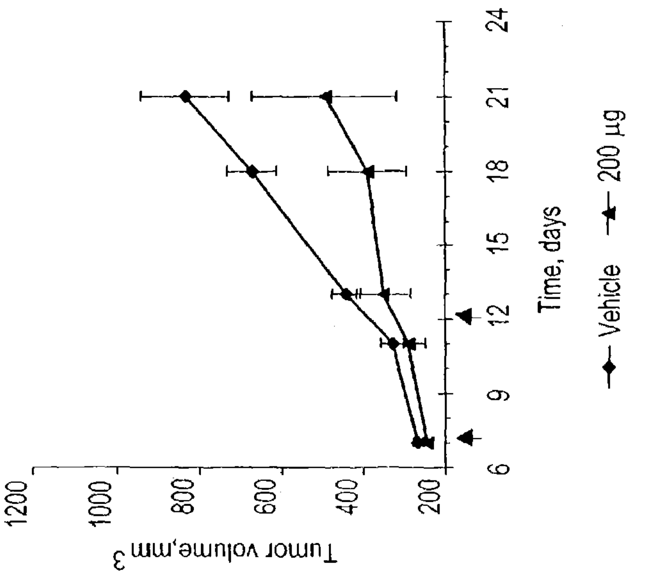
Figure 4E:
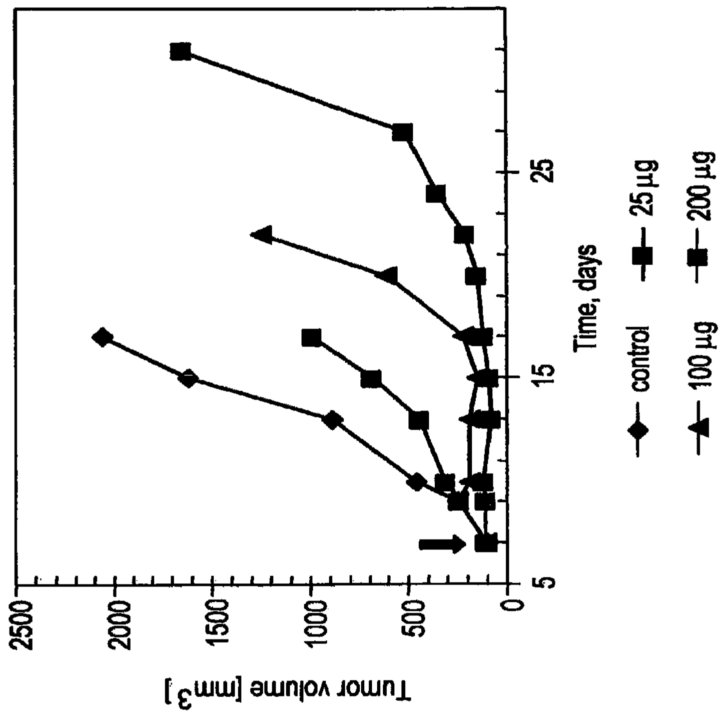

In another embodiment, the anti-c-Met antibody has a selectivity for c-Met that is more than 100 times greater than its selectivity for IGF-1R (Insulin-like Growth Factor 1 Receptor) (See FIG. 2). In some embodiments, the anti-c-Met antibody does not exhibit any appreciable specific binding to any other protein other than c-Met. One can determine the selectivity of the anti-c-Met antibody for c-Met using methods well known in the art following the teachings of the specification. For instance one can determine the selectivity using Western blot, flow cytometry, ELISA, immunoprecipitation or RIA.

Methods of Producing Antibodies and Antibody Producing Cell Lines

Immunization

In some embodiments, human antibodies are produced by immunizing a non-human, transgenic animal comprising within its genome some or all of human immunoglobulin heavy chain and light chain loci with a c-Met antigen. In a preferred embodiment, the non-human animal is a XENOMOUSE™ animal. (Abgenix, Inc., Fremont, Calif.).

XENOMOUSE™ mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-c-Met antibodies from non-human, non-mouse animals by immunizing non-human transgenic animals that comprise human immunoglobulin loci with a c-Met antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle or horses.

XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE™ mice further contain approximately all of the human lambda light chain locus. See Mendez et al., *Nature Genetics* 15:146-156 (1997), Green and Jakobovits, *J. Exp. Med.* 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-c-Met antibodies. In some embodiments, non-human animals are immunized with a c-Met antigen as described below under conditions that permit antibody production. Antibody-producing cells are isolated from the animals, fused with myelomas to produce hybridomas, and nucleic acids encoding the heavy and light chains of an anti-c-Met antibody of interest are isolated. These nucleic acids are subsequently engineered using techniques known to those of skill in the art and as described further below to reduce the amount of non-human sequence, i.e., to humanize the antibody to reduce the immune response in humans In some embodiments, the c-Met antigen is isolated and/or purified c-Met. In a preferred embodiment, the c-Met antigen is human c-Met. In some embodiments, the c-Met antigen is a fragment of c-Met. In some embodiments, the c-Met fragment is the extracellular domain of c-Met. In some embodiments, the c-Met fragment comprises at least one epitope of c-Met. In other embodiments, the c-Met antigen is a cell that expresses or overexpresses c-Met or an immunogenic fragment thereof on its surface. In some embodiments, the c-Met antigen is a c-Met fusion protein. In some embodiments, the c-Met is a synthetic peptide immunogen.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994,619. In a preferred embodiment, the c-Met antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example I exemplifies a method for producing anti-c-Met monoclonal antibodies in XenoMouse™ mice.

Production of Antibodies and Antibody-Producing Cell Lines

After immunization of an animal with a c-Met antigen, antibodies and/or antibody-producing cells can be obtained from the animal. In some embodiments, anti-c-Met antibody-containing serum is obtained from the animal by bleeding or sacrificing the animal. The serum may be used as it is obtained from the animal, an immunoglobulin fraction may be obtained from the serum, or the anti-c-Met antibodies may be purified from the serum.

In some embodiments, antibody-producing immortalized cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using c-Met, a portion thereof, or a cell expressing c-Met. In a preferred embodiment, the initial screening is performed using an enzyme-linked immunoassay (ELISA) or a radioimmunoassay. An example of ELISA screening is provided in WO 00/37504, incorporated herein by reference.

Anti-c-Met antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE™ mouse and the myeloma cell line is a non-secretory mouse myeloma. In an even more preferred embodiment, the myeloma cell line is P3-X63-Ag8.653 (American Type Culture Collection. See, e.g., Example I.

Thus, in one embodiment, the invention provides methods for producing a cell line that produces a human monoclonal antibody or a fragment thereof directed to c-Met comprising (a) immunizing a non-human transgenic animal described herein with c-Met, a portion of c-Met or a cell or tissue expressing c-Met; (b) allowing the transgenic animal to mount an immune response to c-Met; (c) isolating antibody-producing cells from transgenic animal; (d) immortalizing the antibody-producing cells; (e) creating individual monoclonal populations of the immortalized antibody-producing cells; and (f) screening the immortalized antibody-producing cells to identify an antibody directed to c-Met.

In another aspect, the invention provides hybridomas that produce a human anti-c-Met antibody. In a preferred embodiment, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In one embodiment of the invention, antibody-producing cells are isolated and expressed in a host cell, for example myeloma cells. In another preferred embodiment, a transgenic animal is immunized with c-Met, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FR1 regions of human heavy and light chain variable region genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and x or λ constant domains. See Babcook, J. S. et al., Proc. Natl. Acad. Sci. USA 93:7843-48, 1996, incorporated herein by reference. Anti c-Met antibodies may then be identified and isolated as described herein.

In another embodiment, phage display techniques can be used to provide libraries containing a repertoire of antibodies with varying affinities for c-Met. For production of such repertoires, it is unnecessary to immortalize the B cells from the immunized animal. Rather, the primary B cells can be used directly as a source of DNA. The mixture of cDNAs obtained from B cell, e.g., derived from spleens, is used to prepare an expression library, for example, a phage display library transfected into *E. coli*. The resulting cells are tested for immunoreactivity to c-Met. Techniques for the identification of high affinity human antibodies from such libraries are described by Griffiths et al., *EMBO J,* 13:3245-3260 (1994); Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for c-Met and the genetic material recovered from the appropriate clone. Further rounds of screening can increase affinity of the original antibody isolated.

Nucleic Acids, Vectors, Host Cells, and Recombinant Methods of Making Antibodies Nucleic Acids The present invention also encompasses nucleic acid molecules encoding anti-c-Met antibodies. In some embodiments, different nucleic acid molecules encode a heavy chain and a light chain of an anti-c-Met immunoglobulin. In other embodiments, the same nucleic acid molecule encodes a heavy chain and a light chain of an anti-c-Met immunoglobulin. In one embodiment, the nucleic acid encodes a c-Met antibody of the invention.

In some embodiments, the nucleic acid molecule encoding the variable domain of the light chain ($V_L$) comprises a human L5Vκ1 or A27Vκ3 gene, and a Jκ1, Jκ2, Jκ3, or Jκ4 gene.

In some embodiments, the nucleic acid molecule encoding the light chain, encodes an amino acid sequence comprising 1, 2, 3, 4, 5, 6, 7, 8, 9, or 10 substitutions from the germline amino acid sequence(s). In some embodiments, the nucleic acid molecule comprises a nucleotide sequence that encodes a $V_L$ amino acid sequence comprising 1, 2, 3, 4, 5, 6, 7, 8, 9, or 10 conservative amino acid substitutions and/or 1, 2, or 3 non-conservative substitutions compared to germline $V_L$ and $J_K$ sequences. Substitutions may be in the CDR regions, the framework regions, or in the constant domain.

In some embodiments, the nucleic acid molecule encodes a $V_L$ amino acid sequence comprising one or more variants compared to germline sequence that are identical to the variations found in the $V_L$ of one of the antibodies 13.3.2, 9.1.2; 8.70.2; 8.90.3 or 13.3.2L-A91T.

In some embodiments, the nucleic acid molecule encodes at least three amino acid substitutions compared to the germline sequence found in the $V_L$ of one of the antibodies 13.3.2; 9.1.2; 8.70.2; 8.90.3 or 13.3.2L-A91T.

In some embodiments, the nucleic acid molecule comprises a nucleotide sequence that encodes the $V_L$ amino acid sequence of monoclonal antibody 13.3.2 (SEQ ID NO: 4, wherein $X_8$ is alanine); 13.3.2L-A91T (SEQ ID NO: 4, wherein $X_8$ is threonine); 9.1.2 (SEQ ID NO: 8); 8.70.2 (SEQ ID NO: 12); or 8.90.3 (SEQ ID NO: 16), or a variant or portion thereof. In some embodiments, the nucleic acid encodes an amino acid sequence comprising the light chain CDRs of one of said above-listed antibodies. In some embodiments, said portion is a contiguous portion comprising CDR1-CDR3.

In some embodiments, the nucleic acid molecule comprises a nucleotide sequence that encodes the amino acid sequence of one of SEQ ID NOs: 4[13.3.2 (SEQ ID NO: 4, wherein $X_8$ is alanine); 13.3.2L-A91T (SEQ ID NO: 4, wherein $X_8$ is threonine)], 8, 12, or 16, or said sequence lacking the signal sequence. In some preferred embodiments, the nucleic acid molecule comprises the nucleotide sequence of SEQ ID NOs: 3 [13.3.2 (SEQ ID NO: 3 wherein $X_7$ is guanosine); 13.3.2L-A91T (SEQ ID NO: 3, wherein $X_7$ is adenosine)], 7, 11, or 15, or a portion thereof, said sequences optionally lacking the signal sequence.

In some embodiments, the nucleic acid encodes the amino acid sequence of the light chain CDRs of said antibody. In some embodiments, said portion encodes a contiguous region from CDR1-CDR3 of the light chain of an anti-c-Met antibody.

In some embodiments, the nucleic acid molecule encodes a $V_L$ amino acid sequence that is at least 70%, 75%, 80%, 85%, 90%, 95%, 97%, 98% or 99% identical to a $V_L$ amino acid sequences shown in FIG. 3A-3D or to a $V_L$ amino acid sequence of any one of a $V_L$ region of antibodies 13.3.2; 9.1.2; 8.70.2; 8.90.3 or 13.3.2L-A91T, or an amino acid sequence of a $V_L$ region of any one of SEQ ID NOs: 4 [13.3.2 (SEQ ID NO: 4, wherein $X_8$ is alanine); 13.3.2L-A91T (SEQ ID NO.: 4, wherein $X_8$ is threonine)], 8, 12, or 16. Nucleic acid molecules of the invention include nucleic acids that hybridize under highly stringent conditions, such as those described above, to a nucleic acid sequence encoding the amino acid sequence of a nucleic acid molecule encoding a $V_L$ region of SEQ ID NOs: 4 [13.3.2 (SEQ ID NO: 4, wherein $X_8$ is alanine); 13.3.2L-A91T (SEQ ID NO: 4, wherein $X_8$ is threonine)], 8, 12, or 16, or that has the nucleic acid sequence of a nucleic acid molecule encoding a $V_L$ region of SEQ ID NOs: 3 [13.3.2 (SEQ ID NO: 3 wherein $X_7$ is guanosine); 13.3.2L-A91T (SEQ ID NO: 3, wherein $X_7$ is adenosine)], 7, 11, or 15.

In another embodiment, the nucleic acid encodes a full-length light chain of an antibody selected from 13.3.2; 9.1.2; 8.70.2; 8.90.3 or 13.3.2L-A91T, or a light chain comprising the amino acid sequence of SEQ ID NOs: 4[13.3.2 (SEQ ID NO: 4, wherein $X_8$ is alanine); 13.3.2L-A91T (SEQ ID NO: 4, wherein $X_8$ is threonine)], 8, 12, or 16, or a light chain comprising a mutation, such as one disclosed herein. Further, the nucleic acid may comprise the nucleotide sequence of SEQ ID NOs: 3 [13.3.2 (SEQ ID NO: 3 wherein $X_7$ is guanosine); 13.3.2L-A91T (SEQ ID NO: 3, wherein $X_7$ is adenosine)], 7, 11, or 15, or a nucleic acid molecule encoding a light chain comprise a mutation, such as one disclosed herein.

In another preferred embodiment, the nucleic acid molecule encodes the variable domain of the heavy chain ($V_H$) that comprises a human 1-18, 4-31, 4-39 or 3-48 $V_H$ gene sequence or a sequence derived therefrom. In various embodiments, the nucleic acid molecule comprises a human 1-18 $V_H$ gene, a D2-15 gene and a human $J_H$4b gene; a human 4-31 $V_H$ gene, a human D2-2 and D7-27 genes and a $J_H$6b gene; a human 4-31 $V_H$ gene, a human D2-2 gene and a human $J_H$6b gene; a human 4-31 $V_H$ gene, a human D7-27 gene and a human $J_H$6b gene; a human 4-39 $V_H$ gene, a human D2-2 gene and a human $J_H$4b gene; a human 3-48 $V_H$ gene, a human D4-17 gene and a human $J_H$4b gene, or sequence derived from the human genes.

In some embodiments, the nucleic acid molecule encodes an amino acid sequence comprising 1, 2, 3, 4, 5, 6, 7, 8, 9, 10, 11, 12, 13, 14, 15, 16, 17 or 18 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes one or more amino acid mutations compared to the germline sequence that are identical to amino acid mutations found in the $V_H$ of monoclonal antibody 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T or 13.3.2H-A14P, E42K, S97T. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence that encodes at least a portion of the $V_H$ amino acid sequence of a monoclonal antibody selected from 13.3.2 (SEQ ID NO: 2, wherein $X_2$ is glutamate and $X_4$ is serine); 13.3.2H-E42K (SEQ ID NO: 2, wherein $X_2$ is lysine and $X_4$ is serine); 13.3.2H-E42K, S97T (SEQ ID NO: 2, wherein $X_2$ is lysine and $X_4$ is threonine); 9.1.2 (SEQ ID NO: 6); 8.70.2 (SEQ ID NO: 10); or 8.90.3 (SEQ ID NO: 14), a variant thereof, or said sequence having conservative amino acid mutations and/or a total of three or fewer non-conservative amino acid substitutions. In various embodiments the sequence encodes one or more CDR regions, preferably a CDR3 region, all three CDR regions, a contiguous portion including CDR1-CDR3, or the entire $V_H$ region, with or without a signal sequence.

In some embodiments, the nucleic acid molecule comprises a nucleotide sequence that encodes the amino acid sequence of one of SEQ ID NOs: 2, 6, 10, or 14, or said sequence lacking the signal sequence. In some preferred embodiments, the nucleic acid molecule comprises at least a portion of the nucleotide sequence of SEQ ID NO: 1[13.3.2 (SEQ ID NO: 1, wherein $X_1$ is guanosine, $X_3$ is threonine and $X_5$ is guanosine); 13.3.2H-E42K (SEQ ID NO: 1, wherein $X_1$ is adenosine, $X_3$ is threonine and $X_5$ is guanosine); 13.3.2H-E42K, S97T (SEQ ID NO: 1, wherein $X_1$ is adenosine, $X_3$ is adenosine and $X_5$ is guanosine); 13.3.2H-A14P (SEQ ID NO: 1, wherein $X_1$ is guanosine, $X_3$ is threonine and $X_5$ is cytosine); 13.3.2H-A14P, E42K (SEQ ID NO: 1, wherein $X_1$ is adenosine, $X_3$ is threonine and $X_5$ is cytosine); 13.3.2H-A14P, E42K, S97T (SEQ ID NO: 1, wherein $X_1$ is adenosine, $X_3$ is adenosine and $X_5$ is cytosine)], 5, 9, or 13, or said sequence lacking the signal sequence. In some embodiments, said portion encodes the $V_H$ region (with or without a signal sequence), a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequences shown in FIGS. 3E-3H or to a $V_H$ amino acid sequence of any one of SEQ ID NOs: 2 [13.3.2 (SEQ ID NO: 2, wherein $X_2$ is glutamate and $X_4$ is serine); 13.3.2H-E42K (SEQ ID NO: 2, wherein $X_2$ is lysine and $X_4$ is serine); 13.3.2H-E42K, S97T (SEQ ID NO: 2, wherein $X_2$ is lysine and $X_4$ is threonine)], 6, 10, or 14. Nucleic acid molecules of the invention include nucleic acids that hybridize under highly stringent conditions, such as those described above, to a nucleic acid sequence encoding the amino acid sequence of SEQ ID NOs: 2 [13.3.2 (SEQ ID NO: 2, wherein $X_2$ is glutamate, $X_4$ is serine and $X_6$ is alanine); 13.3.2H-E42K (SEQ ID NO: 2, wherein $X_2$ is lysine, $X_4$ is serine and $X_6$ is alanine); 13.3.2H-E42K, S97T (SEQ ID NO: 2, wherein $X_2$ is lysine, is threonine and $X_6$ is alanine); 13.3.2H-A14P (SEQ ID NO: 2, wherein $X_2$ is glutamate, $X_4$ is serine and $X_6$ is proline); 13.3.2H-A14P, E42K (SEQ ID NO: 2, wherein $X_2$ is lysine, $X_4$ is serine and $X_6$ is proline); 13.3.2H-A14P, E42K, S97T (SEQ ID NO: 2, wherein $X_2$ is lysine, $X_4$ is threonine and $X_6$ is proline)], 6, 10, or 14, or to a $V_H$ region thereof, or that has the nucleic acid sequence of SEQ ID NOs: 1 [13.3.2 (SEQ ID NO: 1, wherein $X_1$ is guanosine, $X_3$ is threonine and $X_5$ is guanosine); 13.3.2H-E42K (SEQ ID NO: 1, wherein $X_1$ is adenosine, $X_3$ is threonine and $X_5$ is guanosine); 13.3.2H-E42K, S97T (SEQ ID NO: 1, wherein $X_1$ is adenosine, $X_3$ is adenosine and $X_5$ is guanosine); 13.3.2H-A14P (SEQ ID NO: 1, wherein $X_1$ is guanosine, $X_3$ is threonine and $X_5$ is cytosine); 13.3.2H-A14P, E42K (SEQ ID NO: 1, wherein $X_1$ is adenosine, $X_3$ is threonine and $X_5$ is cytosine); 13.3.2H-A14P, E42K, S97T (SEQ ID NO: 1, wherein $X_1$ is adenosine, $X_3$ is adenosine and $X_5$ is cytosine)], 5, 9, or 13 or that encodes a $V_H$ region thereof.

In another embodiment, the nucleic acid encodes a full-length heavy chain of an antibody selected from 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T or 13.3.2H-A14P, E42K, S97T, or a heavy chain having the amino acid sequence of SEQ ID NOs: 2 [13.3.2 (SEQ ID NO: 2, wherein $X_2$ is glutamate, $X_4$ is serine and $X_6$ is alanine); 13.3.2H-E42K (SEQ ID NO: 2, wherein $X_2$ is lysine, $X_4$ is serine and $X_6$ is alanine); 13.3.2H-E42K, S97T (SEQ ID NO: 2, wherein $X_2$ is lysine, $X_4$ is threonine and $X_6$ is alanine); 13.3.2H-A14P (SEQ ID NO: 2, wherein $X_2$ is glutamate, $X_4$ is serine and $X_6$ is proline); 13.3.2H-A14P, E42K (SEQ ID NO: 2, wherein $X_2$ is lysine, $X_4$ is serine and $X_6$ is proline); 13.3.2H-A14P, E42K, S97T (SEQ ID NO: 2, wherein $X_2$ is lysine, $X_4$ is threonine and $X_6$ is proline)], 6, 10, or 14, with or without a signal sequence, or a heavy chain comprising a mutation, such as one of the variants discussed herein. Further, the nucleic acid may comprise the nucleotide sequence of SEQ ID NOs: 1 [13.3.2 (SEQ ID NO: 1, wherein $X_1$ is guanosine, $X_3$ is threonine and $X_5$ is guanosine); 13.3.2H-E42K (SEQ ID NO: 1, wherein $X_1$ is adenosine, $X_3$ is threonine and $X_5$ is guanosine); 13.3.2H-E42K, S97T (SEQ ID NO: 1, wherein $X_1$ is adenosine, $X_3$ is adenosine and $X_5$ is guanosine); 13.3.2H-A14P (SEQ ID NO: 1, wherein $X_1$ is guanosine, $X_3$ is threonine and $X_5$ is cytosine); 13.3.2H-A14P, E42K (SEQ ID NO: 1, wherein $X_1$ is adenosine, $X_3$ is threonine and $X_5$ is cytosine); 13.3.2H-A14P, E42K, S97T (SEQ ID NO: 1, wherein $X_1$ is adenosine, $X_3$ is adenosine and $X_5$ is cytosine)], 5, 9, or 13, with or without a signal sequence, or a nucleic acid molecule encoding a heavy chain comprising a mutation, such as one of the variants discussed herein.

A nucleic acid molecule encoding the heavy or light chain of an anti-c-Met antibody or portions thereof can be isolated from any source that produces such antibody. In various embodiments, the nucleic acid molecules are isolated from a B cell isolated from an animal immunized with c-Met or from an immortalized cell derived from such a B cell that expresses an anti-c-Met antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin-producing cell from a non-human transgenic animal. In an even more preferred embodiment, the human immunoglobulin producing cell is isolated from a XENOMOUSE™ animal. In another embodiment, the human immunoglobulin-producing cell is from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies.

In some embodiments, a nucleic acid encoding a heavy chain of an anti-c-Met antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-c-Met antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the art. See, e.g., Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-c-Met antibody isolated.

The nucleic acid molecules may be used to recombinantly express large quantities of anti-c-Met antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-c-Met antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies 13.3.2; 9.1.2; 8.70.2; 8.90.3 or variants thereof as described herein.

Vectors

The invention provides vectors comprising nucleic acid molecules that encode the heavy chain of an anti-c-Met antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-c-Met antibodies or antigen-binding portions of the invention are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding anti-c-Met antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-c-Met antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-c-Met antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with c-Met or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding an anti-c-Met antibody of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* $2^{nd}$ ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to c-Met, preferably human c-Met. In some embodiments, the transgenic animals comprise nucleic acid molecules encoding a modified antibody such as a single-chain antibody, a chimeric antibody or a humanized antibody. The anti-c-Met antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-c-Met antibody or antigen-binding portion thereof comprising the steps of synthesizing a library of human antibodies on phage, screening the library with c-Met or a portion thereof isolating phage that bind c-Met, and obtaining the antibody from the phage. By way of example, one method for preparing the library of antibodies for use in phage display techniques comprises the steps of immunizing a non-human animal comprising human immunoglobulin loci with c-Met or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-c-Met antibodies of the invention may be obtained in this way.

Recombinant anti-c-Met human antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al.,

*EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-c-Met antibodies with the desired characteristics, a human anti-c-Met antibody as described herein is first used to select human heavy and light chain sequences having similar binding activity toward c-Met, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. The scFv antibody libraries preferably are screened using human c-Met as the antigen.

Once initial human $V_L$ and $V_H$ domains are selected, "mix and match" experiments are performed, in which different pairs of the initially selected $V_L$ and $V_H$ segments are screened for c-Met binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to c-Met.

Following screening and isolation of an anti-c-Met antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Class Switching

Another aspect of the invention provides a method for converting the class or subclass of an anti-c-Met antibody to another class or subclass. In some embodiments, a nucleic acid molecule encoding a $V_L$ or $V_H$ that does not include sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, an anti-c-Met antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of an anti-c-Met antibody and a nucleic acid encoding a light chain of an anti-c-Met antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the anti-c-Met antibody with the desired isotype.

Deimmunized Antibodies

In another aspect of the invention, the antibody may be deimmunized to reduce its immunogenicity using the techniques described in, e.g., PCT Publication Nos. WO98/52976 and WO00/34317 (incorporated herein by reference).

Mutated Antibodies

In another embodiment, the nucleic acid molecules, vectors and host cells may be used to make mutated anti-c-Met antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for c-Met, to increase or decrease $k_{off}$, or to alter the binding specificity of the antibody. Techniques in site-directed mutagenesis are well-known in the art. See, e.g., Sambrook et al. and Ausubel et al., supra. In another embodiment, one or more mutations are made at an amino acid residue that is known to be changed compared to the germline in monoclonal antibody 13.3.2; 9.1.2; 8.70.2; 8.90.3; 13.3.2H-A14P; 13.3.2H-E42K; 13.3.2H-S97T; 13.3.2H-A14P, E42K; 13.3.2H-E42K, S97T; 13.3.2H-A14P, E42K, S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of an amino acid sequence selected from SEQ ID NOs: 2 [13.3.2 (SEQ ID NO: 2, wherein $X_2$ is glutamate, $X_4$ is serine and $X_6$ is alanine); 13.3.2H-E42K (SEQ ID NO: 2, wherein $X_2$ is lysine, $X_4$ is serine and $X_6$ is alanine); 13.3.2H-E42K, S97T (SEQ ID NO: 2, wherein $X_2$ is lysine, $X_4$ is threonine and $X_6$ is alanine); 13.3.2H-A14P (SEQ ID NO: 2, wherein $X_2$ is glutamate, $X_4$ is serine and $X_6$ is proline); 13.3.2H-A14P, E42K (SEQ ID NO: 2, wherein $X_2$ is lysine, $X_4$ is serine and $X_6$ is proline); 13.3.2H-A14P, E42K, S97T (SEQ ID NO: 2, wherein $X_2$ is lysine, $X_4$ is threonine and $X_6$ is proline)], 4 [13.3.2 (SEQ ID NO: 4, wherein $X_8$ is alanine) and the 13.3.2L-A91T (SEQ ID NO: 4, wherein $X_8$ is threonine)], 6, 8, 10, 12, 14 or 16 or whose nucleic acid sequence is presented in SEQ ID NOs: 1 [13.3.2 (SEQ ID NO: 1, wherein $X_1$ is guanosine, $X_3$ is threonine and $X_5$ is guanosine); 13.3.2H-E42K (SEQ ID NO: 1, wherein $X_1$ is adenosine, $X_3$ is threonine and $X_5$ is guanosine); 13.3.2H-E42K, S97T (SEQ ID NO: 1, wherein $X_1$ is adenosine, $X_3$ is adenosine and $X_5$ is guanosine); 13.3.2H-A14P (SEQ ID NO: 1, wherein $X_1$ is guanosine, $X_3$ is threonine and $X_5$ is cytosine); 13.3.2H-A14P, E42K (SEQ ID NO: 1, wherein $X_1$ is adenosine, $X_3$ is threonine and $X_5$ is cytosine); 13.3.2H-A14P, E42K, S97T (SEQ ID NO: 1, wherein $X_1$ is adenosine, $X_3$ is adenosine and $X_5$ is cytosine)], 3 [13.3.2 (SEQ ID NO: 3 wherein $X_7$ is guanosine); 13.3.2L-A91T (SEQ ID NO: 3, wherein $X_7$ is adenosine)], 5, 7, 9, 11, 13 or 15.

In another embodiment, the framework region is mutated so that the resulting framework region(s) have the amino acid sequence of the corresponding germline gene. A mutation may be made in a framework region or constant domain to increase the half-life of the anti-c-Met antibody. See, e.g., PCT Publication No. WO 00/09560, incorporated herein by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 8, including any number in between, amino acid mutations in either the $V_H$ or $V_L$ domains of the mutated anti-c-Met antibody compared to the anti-c-Met antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-c-Met antibody of the invention linked to another polypeptide. In a preferred embodiment, only the variable domains of the anti-c-Met antibody are linked to the polypeptide. In another preferred embodiment, the $V_H$ domain of an anti-c-Met antibody is linked to a first polypeptide, while the $V_L$ domain of an anti-c-Met antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. The fusion antibody is useful for directing a polypeptide to a c-Met-expressing cell or tissue. The polypeptide may be a therapeutic agent, such as a toxin, growth factor or other regulatory protein, or may be a diagnostic agent, such as an enzyme that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to c-Met and to another molecule.

In other embodiments, other modified antibodies may be prepared using anti-c-Met antibody encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol.* 148:1547-1553 (1992). In addition, bispecific antibodies may be formed as "diabodies" or "Janusins." In some embodiments, the bispecific antibody binds to two different epitopes of c-Met. In some embodiments, the bispecific antibody has a first heavy chain and a first light chain from monoclonal antibody. 13.3.2; 9.1.2; 8.70.2; 8.90.3; 13.3.2H-A14P; 13.3.2H-E42K; 13.3.2H-A14P, E42K; 13.3.2H-S97T; 13.3.2H-E42K, S97T; 13.3.2H-A14P, E42K, S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-c-Met monoclonal antibody provided herein.

Derivatized and Labeled Antibodies

An anti-c-Met antibody or antigen-binding portion of the invention can be derivatized or linked to another molecule (e.g., another peptide or protein). In general, the antibodies or portion thereof are derivatized such that the c-Met binding is not affected adversely by the derivatization or labeling. Accordingly, the antibodies and antibody portions of the invention are intended to include both intact and modified forms of the human anti-c-Met antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Il.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-c-Met antibody can also be labeled with a radiolabeled amino acid. The radiolabel can be used for both diagnostic and therapeutic purposes. For instance, the radiolabel can be used to detect c-Met-expressing tumors by x-ray or other diagnostic techniques. Further, the radiolabel can be used therapeutically as a toxin for cancerous cells or tumors. Examples of labels for polypeptides include, but are not limited to, the following radioisotopes or radionuclides—$^{3}H$, $^{14}C$, $^{15}N$, $^{35}S$, $^{90}Y$, $^{99}Tc$, $^{111}In$, $^{125}I$, and $I^{131}$.

An anti-c-Met antibody can also be derivatized with a chemical group such as polyethylene glycol (PEG), a methyl or ethyl group, or a carbohydrate group. These groups are useful to improve the biological characteristics of the antibody, e.g., to increase serum half-life or to increase tissue binding.

Pharmaceutical Compositions and Kits

The invention relates to compositions comprising a human anti-c-Met antibody with agonist properties for the treatment of patients in need of a therapeutic procedure including, but not limited to, tissue regeneration or wound healing. In some embodiments, the subject of treatment is a human. In other embodiments, the subject is a veterinary subject. Examples of tissues, in need of tissue regeneration include but are not limited to liver tissue (as in the case of acute, chronic or alcoholic hepatitis or cirrhosis), lung tissue, stomach tissue (as in the case of gastric ulcers) and kidney tissue (as in the case of acute renal failure). Agonist anti-c-Met antibodies of the invention and compositions comprising them, can be administered in combination with one or more other therapeutic, diagnostic, or prophylactic agents. In some embodiments, one or more agonist c-Met antibodies of the invention can be used as a vaccine or as adjuvants to a vaccine. Treatment may involve administration of one or more agonist anti-c-Met monoclonal antibodies of the invention, or antigen-binding fragments thereof, alone or with a pharmaceutically acceptable carrier.

In a further aspect, an anti-c-Met antibody of the invention that has inhibitory properties can involve any tissue or organ including but not limited to brain, lung, squamous cell, bladder, gastric, pancreatic, breast, head, neck, liver, renal, ovarian, prostate, colorectal, esophageal, gynecological, nasopharynx, or thyroid cancers, melanomas, lymphomas, leukemias, multiple myelomas, choriocarcinoma, Kaposi or cervical intraepithelial neoplasia. Other disorders that may be treated or prevented by an anti-c-Met antibody of the invention that has inhibitory properties include, but are not limited to, proliferative vitreoretinopathy, proliferative diabetic retinopathy, endometriosis and arthritis. In other embodiments of the invention, anti-c-Met antibodies can be used to inhibit plaque formation in Alzheimer's disease and to inhibit cellular mitogenic responses. Anti-c-Met antibodies of the invention could be used to inhibit embryo implantation by inclusion in an injectable contraceptive. Anti-c-Met antibodies can be used to treat tumor growth by inhibiting proliferation, treat/inhibit tumor angiogenesis, or treat metatstatic spread/dissemination of metastases. In particular, human anti-c-Met antibodies of the invention with inhibitory properties are useful to treat glioblastoma, sarcomas, or carcinomas, for example, of the breast, ovary, prostate, colon, or lung.

Treatment may involve administration of one or more inhibitory anti-c-Met monoclonal antibodies of the invention, or antigen-binding fragments thereof, alone or with a pharmaceutically acceptable carrier. Inhibitory anti-c-Met antibodies of the invention and compositions comprising them, can be administered in combination with one or more other therapeutic, diagnostic or prophylactic agents. Additional therapeutic agents include other anti-neoplastic, anti-tumor, anti-angiogenic or chemotherapeutic agents. Such additional agents may be included in the same composition or administered separately. In some embodiments, one or more inhibitory anti-c-Met antibodies of the invention can be used as a vaccine or as adjuvants to a vaccine.

In addition to cancer vaccines comprised of cancer-associated antigens, vaccines useful in combination with the antibody include, without limitation, GM-CSF DNA and cell-based vaccines, dendritic cell vaccines, recombinant viral (e.g. vaccinia virus) vaccines, and heat shock protein (HSP) vaccines. Useful vaccines also include tumor vaccines, such as those formed of melanoma cells; and may be autologous or allogeneic. The vaccines may be, e.g., peptide, DNA or cell based.

As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-c-Met antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

In certain embodiments, an anti-c-Met antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-c-Met antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, an inhibitory anti-c-Met antibody of the invention is co-formulated with and/or co-administered with one or more additional therapeutic agents. These agents include, without limitation, antibodies that bind other targets, antineoplastic agents, antitumor agents, chemotherapeutic agents, peptide analogues that inhibit c-Met, or antibodies or other molecules that bind to HGF and prevent its binding to or activation of c-Met. Such combination therapies may require lower dosages of the inhibitory anti-c-met antibody as well as the co-administered agents, thus avoiding possible toxicities or complications associated with the various monotherapies.

Inhibitory anti-c-Met antibodies of the invention and compositions comprising them also may be administered in combination with other therapeutic regimens, in particular in combination with radiation treatment.

In certain embodiments, an activating or inhibiting anti-c-Met antibody of the invention is co-formulated with and/or co-administered with one or more additional therapeutic agents. In the case of an activating c-Met antibody, these agents include, without limitation, one or more chemical agents that activate c-Met and/or other agents known in the art to enhance a therapeutic procedure such as tissue regeneration or wound healing. In the case of an inhibitory antibody, these agents include those that inhibit c-Met. Further, such combination therapies may also be used to treat diseases like arteriosclerosis obliterans, renal tubulointerstitial fibrosis, refractory skin ulcers, gastric ulcers or problems associated with transplant. Such combination therapies may require lower dosages of the inhibitory or agonist anti-c-met antibody as well as the co-administered agents, thus avoiding possible toxicities or complications associated with the various monotherapies.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-c-Met antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/ml of antibody in a buffer of 20 mM sodium citrate, pH 5.5, 140 mM NaCl, and 0.2 mg/ml polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-c-Met antibody or antibody portion of the invention or a composition comprising such an antibody. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

This invention also relates to compositions for inhibiting abnormal cell growth in a mammal comprising an amount of an antibody of the invention in combination with an amount of a chemotherapeutic agent, wherein the amounts of the compound, salt, solvate, or prodrug, and of the chemotherapeutic agent are together effective in inhibiting abnormal cell growth. Many chemotherapeutic agents are presently known in the art. In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g., anti-androgens, and anti-angiogenesis agents.

Anti-angiogenic agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with an anti-c-Met antibody of the invention. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference.

Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo [3.2.1]octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

An anti-c-Met antibody of the invention also can be used with signal transduction inhibitors, such as agents that can inhibit EGF-R (epidermal growth factor receptor) responses, including but not limited to EGF-R antibodies, EGF antibodies, and molecules that are EGF-R inhibitors; VEGF (vascular endothelial growth factor) and VEGF receptor (VEGF-R) inhibitors; and erbB2 receptor inhibitors, such as organic molecules or antibodies that bind to the erbB2 receptor, for example, HERCEPTIN™ (Genentech, Inc.). EGF-R inhibitors are described in, for example, in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), all incorporated herein by reference, and such substances can be used in the present invention as described herein.

EGF-R-inhibiting agents include, but are not limited to, the monoclonal antibodies C225 and anti-EGF-R 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and IRESSA™ (ZD-1839) (AstraZeneca), PKI-166 (Novartis), PKI-166/CGP-75166 (Novartis), PTK 787 (Novartis), CP 701 (Cephalon), leflunomide (Pharmacia/Sugen), Tarceva™ (OSI, Roche and Genetech), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)). These and other EGF-R-inhibiting agents can be used in the present invention.

VEGF-R and VEGF inhibitors, for example SU-5416, SU-11248 and SU-6668 (Sugen Inc.), SH-268 (Schering), and NX-1838 (NeXstar) can also be combined with the compound of the present invention. VEGF and VEGF-R inhibitors are described in, for example in WO 99/24440 (published May 20, 1999), PCT International Application PCT/IB99/

00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference.

Other examples of some specific VEGF-R and VEGF inhibitors useful in the present invention are IM862 (Cytran Inc.); Avastin™; and angiozyme, a synthetic ribozyme from Ribozyme and Chiron. These and other VEGF and VEGF-R inhibitors can be used in the present invention as described herein.

ErbB2 receptor inhibitors, such as GW-282974 (Glaxo Wellcome plc), and the monoclonal antibodies AR-209 (Aronex Pharmaceuticals Inc.) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,465,449 (issued Oct. 15, 2002), and in U.S. Pat. No. 6,284,764 (issued Sep. 4, 2001), incorporated herein by reference. The erbB2 receptor inhibitor compounds and substances described in the aforementioned patent documents, as well as other compounds and substances that inhibit the erbB2 receptor, can be used with the compound of the present invention in accordance with the present invention.

An anti-c-Met antibody of the invention also can be used with inhibitors of PDGFR, BCR-ABL or c-kit such as Gleevec™ (Novaritis).

An anti-c-Met antibody of the invention also can be used with anti-IGF-IR antibodies such as those described in WO 02053596 (published Jul. 11, 2002), for example an antibody having the sequence of antibody 2.12.1, 2.13.2, 2.14.3, 3.1.1, 4.9.2 or 4.17.3. The antibody of the invention can also be used with CTLA-4 antibodies, such as those described in U.S. Pat. No. 6,682,736, including an antibody having the sequence of antibody 3.1.1, 4.1.1, 4.8.1, 4.10.2, 4.13.1, 4.14.3, 6.1.1, 11.2.1, 11.6.1, 11.7.1, 12.3.1.1, or 12.9.1.1. The antibody can also be used with CD40 antibodies, such as those described in WO03040170 published May 15, 2003, including one having the sequence of antibody 3.1.1, 3.1.11-1-A78T, 3.1.1H-A78T-V88A-V97A, 7.1.2, 10.8.3, 15.1.1, 21.4.1, 21.2.1, 22.1.1, 22.1.1H-C109A, 23.5.1, 23.25.1, 23.28.1, 23.28.1H-D16E, 23.29.1 or 24.2. The antibodies can also be combined with anti-integrin agents, such as anti-integrin antibodies.

Some specific examples of agents that the antibody may be combined with include the following: (1) the alkylating agents nitrogen mustard N-oxide, cyclophosphamide, ifosfamide, melphalan, busulfanmitobronitol, carboquone, thiotepa, ranimustine, nimustine, and temozolomide; (2) the anti-metabolites methotrexate, 6-mercaptopurine, riboside, mercaptopurine, 5-FU, tegafur, doxifluridine, carmofur, cytarabine, cytarabine, ocfosfate, enocitabine, S-1, Gemcitabine, Fludarabine, and Capecitabine; (3) the antibiotics actinomycin D, doxorubicin, daunorubicin, neocarzinostatin, bleomycin, peplomycin, mitomycin C, aclarubicin, pirarubicin, epirubicin, zinostatin, stimalamer, and idarubicin; (4) the plant-derived antitumor agents vincristine, vinblastine, vindeshine, etoposide, sobuzoxane, docetaxel, paclitaxel, and vinorelbine; (5) the platinum-coordinated compounds cisplatin, carboplatin, nedaplatin, and oxaliplatin; (6) camptothecin derivates irinotecan, topotecan and campthotecin; (7) tyrosine kinase inhibitors Iressa™ (gefitinib) and SU5416; (8) anti-CD20 agents such as Rituxan™ (Rituximab) Bexxar (tositumomab), and Zevalin™ (Ibritumomab tiuxetan); (9) interferons interferon alpha, interferon alpha-2a, interferon alpha-2b, interferon beta, interferon gamma-1a and interferon gamma-n1; (10) biological response modifiers krestin, lentinan, sizofuran, picibanil and ubenimex; or (11) other antitumor agents mitoxantrone, 1-asparaginase, procarbazine, dacarbazine, hydroxycarbamide, pentostatin, and Tretinoin. In addition, the antibody of the invention can be combined with anti-cancer agents such as exemestane, Edotecarin™ (J-107088), and SU11248.

Diagnostic Methods of Use

In another aspect, the invention provides diagnostic methods. The anti-c-Met antibodies can be used to detect c-Met in a biological sample in vitro or in vivo. In one embodiment, the invention provides a method for diagnosing the presence or location of an c-Met-expressing tumor in a subject in need thereof, comprising the steps of injecting the antibody into the subject, determining the expression of c-Met in the subject by localizing where the antibody has bound, comparing the expression in the subject with that of a normal reference subject or standard, and diagnosing the presence or location of the tumor.

The anti-c-Met antibodies can be used in a conventional immunoassay, including, without limitation, an ELISA, an RIA, flow cytometry, tissue immunohistochemistry, Western blot or immunoprecipitation. The anti-c-Met antibodies of the invention can be used to detect c-Met from humans. In another embodiment, the anti-c-Met antibodies can be used to detect c-Met from cynomolgus monkeys or rhesus monkeys. In another embodiment, the anti-c-Met antibodies can be used to detect c-Met from rats.

The invention provides a method for detecting c-Met in a biological sample comprising contacting the biological sample with an anti-c-Met antibody of the invention and detecting the bound antibody. In one embodiment, the anti-c-Met antibody is directly labeled with a detectable label. In another embodiment, the anti-c-Met antibody (the first antibody) is unlabeled and a second antibody or other molecule that can bind the anti-c-Met antibody is labeled. As is well known to one of skill in the art, a second antibody is chosen that is able to specifically bind the particular species and class of the first antibody. For example, if the anti-c-Met antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been disclosed supra, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

In other embodiments, c-Met can be assayed in a biological sample by a competition immunoassay utilizing c-Met standards labeled with a detectable substance and an unlabeled anti-c-Met antibody. In this assay, the biological sample, the labeled c-Met standards and the anti-c-Met antibody are combined and the amount of labeled c-Met standard bound to the unlabeled antibody is determined. The amount of c-Met in the biological sample is inversely proportional to the amount of labeled c-Met standard bound to the anti-c-Met antibody.

One can use the immunoassays disclosed above for a number of purposes. For example, the anti-c-Met antibodies can be used to detect c-Met in cultured cells. In a preferred embodiment, the anti-c-Met antibodies are used to determine the amount of c-Met on the surface of cells that have been treated with various compounds. This method can be used to identify compounds that modulate c-Met protein levels. According to this method, one sample of cells is treated with a test compound for a period of time while another sample is left untreated. If the total level of c-Met is to be measured, the cells are lysed and the total c-Met level is measured using one of the immunoassays described above. The total level of c-Met in the treated versus the untreated cells is compared to determine the effect of the test compound.

A preferred immunoassay for measuring total c-Met levels is flow cytometry or immunohistochemistry. If the cell surface level of c-Met is to be measured, the cells are not lysed, and the cell surface levels of c-Met are measured using one of the immunoassays described above. A preferred immunoassay for determining cell surface levels of c-Met includes the steps of labeling the cell surface proteins with a detectable label, such as biotin or $^{125}I$, immunoprecipitating the c-Met with an anti-c-Met antibody and then detecting the labeled c-Met.

Another preferred immunoassay for determining the localization of c-Met, e.g., cell surface levels, is by using immunohistochemistry. A preferred immunoassay to detect cell surface levels of c-Met includes binding of an anti-c-Met antibody labeled with an appropriate fluorophore, such as fluorescein or phycoerythrin, and detecting the primary antibody using flow cytometry. In another embodiment, the anti-c-Met antibody is unlabeled and a second antibody or other molecule that can bind the anti-c-Met antibody is labeled Methods such as ELISA, RIA, flow cytometry, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of c-Met.

The anti-c-Met antibodies of the invention also can be used to determine the levels of c-Met in a tissue or in cells derived from the tissue. In some embodiments, the tissue is a diseased tissue. In some embodiments, the tissue is a tumor or a biopsy thereof. In some embodiments of the method, a tissue or a biopsy thereof is excised from a patient. The tissue or biopsy is then used in an immunoassay to determine, e.g., total c-Met levels, cell surface levels of c-Met or localization of c-Met by the methods discussed above.

The above-described diagnostic method can be used to determine whether a tumor expresses high levels of c-Met, which could be indicative that the tumor is a target for treatment with anti-c-Met antibody. The diagnostic method can also be used to determine whether a tissue or cell expresses insufficient levels of c-Met or activated c-Met, and thus is a candidate for treatment with activating anti-c-Met antibodies, HGF and/or other therapeutic agents for increasing c-Met levels or activity.

The antibodies of the present invention also can be used in vivo to identify tissues and organs that express c-Met. In some embodiments, the anti-c-Met antibodies are used to identify c-Met-expressing tumors. One advantage of using the human anti-c-Met antibodies of the present invention is that they may safely be used in vivo without eliciting a substantial immune response to the antibody upon administration, unlike antibodies of non-human origin or with humanized or chimeric antibodies.

The method comprises the steps of administering a detectably labeled anti-c-Met antibody or a composition comprising them to a patient in need of such a diagnostic test and subjecting the patient to imaging analysis to determine the location of the c-Met-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radioisotopes, such as $^{99}Tc$. In another embodiment, the anti-c-Met antibody will be unlabeled and will be imaged by administering a second antibody or other molecule that is detectable and that can bind the anti-c-Met antibody. In embodiment, a biopsy is obtained from the patient to determine whether the tissue of interest expresses c-Met.

Therapeutic Methods of Use

In another embodiment, the invention provides a method for inhibiting c-Met activity by administering an anti-c-Met antibody to a patient in need thereof. In another embodiment, the invention provides a method for activating c-Met activity by administering an anti-c-Met antibody to a patient in need thereof. Any of the types of antibodies described herein may be used therapeutically. In a preferred embodiment, the anti-c-Met antibody is a human, chimeric or humanized antibody. In another preferred embodiment, the c-Met is human and the patient is a human patient. Alternatively, the patient may be a mammal that expresses a c-Met that the anti-c-Met antibody cross-reacts with. The antibody may be administered to a non-human mammal expressing c-Met with which the antibody cross-reacts (i.e. a rat, or a cynomologus monkey) for veterinary purposes or as an animal model of human disease. Such animal models may be useful for evaluating the therapeutic efficacy of antibodies of this invention.

As used herein, the term "a disorder in which c-Met activity is detrimental" is intended to include diseases and other disorders in which the presence of high levels of c-Met in a subject suffering from the disorder has been shown to be or is suspected of being either responsible for the pathophysiology of the disorder or a factor that contributes to a worsening of the disorder. Such disorders may be evidenced, for example, by an increase in the levels of c-Met on the cell surface or in increased tyrosine autophosphorylation of c-Met in the affected cells or tissues of a subject suffering from the disorder. The increase in c-Met levels may be detected, for example, using an anti-c-Met antibody as described above.

In one embodiment, an anti-c-Met antibody may be administered to a patient who has an c-Met-expressing tumor. A tumor may be a solid tumor or may be a non-solid tumor, such as a lymphoma. In a more preferred embodiment, an anti-c-Met antibody may be administered to a patient who has an c-Met-expressing tumor that is cancerous. In an even more preferred embodiment, the anti-c-Met antibody is administered to a patient who has a c-Met-expressing tumor of the lung, breast, prostate, or colon. In another preferred embodiment, the anti-c-Met antibody is administered to a patient who has a glioblastoma tumor that expresses c-Met. In a highly preferred embodiment, the method causes the tumor not to increase in weight or volume or to decrease in weight or volume. In another embodiment, the method prevents HGF binding to c-Met on the surface of the tumor cells or results in a down-regulation of c-Met cell surface protein. In a preferred embodiment, the antibody is selected from 13.3.2; 9.1.2; 8.70.2; 8.90.3; 13.3.2H-A14P; 13.3.2H-E42K; 13.3.2H-A14P, E42K; 13.3.2H-S97T; 13.3.2H-E42K, S97T; 13.3.2H-A14P, E42K, S97T; 13.3.2L-A91T; 13.3.2L-A91T, H-A14P; 13.3.2L-A91T, H-E42K; 13.3.2L-A91T, H-A14P, E42K; 13.3.2L-A91T, H-E42K, S97T or 13.3.2L-A91T, H-A14P, E42K, S97T, or comprises a heavy chain, light chain or antigen-binding region thereof.

In another preferred embodiment, an anti-c-Met antibody may be administered to a patient who expresses inappropriately high levels of c-Met. It is known in the art that high-level expression of c-Met can lead to a variety of common cancers. In one embodiment, said method relates to the treatment of cancer such as brain, squamous cell, bladder, gastric, pancreatic, breast, head and neck, esophageal, prostate, colorectal, lung, renal, kidney, ovarian, gynecological or thyroid cancer. Patients that can be treated with a compounds of the invention according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, especially hereditary and sporadic papillary renal cell carcinomas that have activating mutations in the c-Met kinase domain, carcinoma of the renal pelvis), or neoplasms of the central nervous system (e.g., primary CNS lymphoma, spinal axis tumors, brain stem gliomas or pituitary adenomas). In a more preferred embodiment, the anti-c-Met antibody is administered to a patient with breast cancer, prostate cancer, lung cancer, colon cancer or a glioblastoma. In an even more preferred embodiment, the method causes the cancer to stop proliferating abnormally, or not to increase in weight or volume or to decrease in weight or volume.

The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via an oral, mucosal, buccal, intranasal, inhalable, intravenous, subcutaneous, intramuscular, parenteral, intratumor or topical route. The antibody may be administered at the site of the tumor, into the tumor, or at a site distant from the site of the tumor. The antibody may be administered once, at least twice or for at least the period of time until the condition is treated, palliated or cured. The antibody generally will be administered for as long as the tumor is present provided that the antibody causes the tumor or cancer to stop growing or to decrease in weight or volume. The antibody will generally be administered as part of a pharmaceutical composition as described supra. The dosage of antibody will generally be in the range of 0.1-100 mg/kg, more preferably 0.5-50 mg/kg, more preferably 1-20 mg/kg, and even more preferably 1-10 mg/kg. The serum concentration of the antibody may be measured by any method known in the art.

In another aspect, the anti-c-Met antibody may be co-administered with other therapeutic agents, such as anti-neoplastic drugs or molecules, to a patient who has a hyperproliferative disorder, such as cancer or a tumor. In one aspect, the invention relates to a method for the treatment of the hyperproliferative disorder in a mammal comprising administering to said mammal a therapeutically effective amount of a compound of the invention in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, the anti-c-Met antibody may be administered with an antibody or other agent that is known to inhibit tumor or cancer cell proliferation, e.g., an antibody or agent that inhibits erbB2 receptor, EGF-R, CD20 or VEGF.

Co-administration of the antibody with an additional therapeutic agent (combination therapy) encompasses administering a pharmaceutical composition comprising the anti-c-Met antibody and the additional therapeutic agent as well as administering two or more separate pharmaceutical compositions, one comprising the anti-c-Met antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent, for example after a patient has failed therapy with the additional agent. Similarly, administration of the anti-c-Met antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months and once every six months, or may be administered continuously via a minipump. The combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the antibody causes the tumor or cancer to stop growing or to decrease in weight or volume.

In a still further embodiment, the anti-c-Met antibody is labeled with a radiolabel, an immunotoxin or a toxin, or is a fusion protein comprising a toxic peptide. The anti-c-Met antibody or anti-c-Met antibody fusion protein directs the radiolabel, immunotoxin, toxin or toxic peptide to the c-Met-expressing tumor or cancer cell. In a preferred embodiment, the radiolabel, immunotoxin, toxin or toxic peptide is internalized after the anti-c-Met antibody binds to the c-Met on the surface of the tumor or cancer cell.

In another aspect, the anti-c-Met antibody may be used to treat non-cancerous diseases or conditions that are associated with c-Met. In one embodiment, the method comprises the step of administering an anti-c-Met antibody to a patient who has a non-cancerous pathological state caused or exacerbated by c-Met activity. In a more preferred embodiment, the anti-c-Met antibody slows the progress of the non-cancerous pathological state. In a more preferred embodiment, the anti-c-Met antibody stops or reverses, at least in part, the non-cancerous pathological state.

In another aspect, the invention provides a method of administering an activating anti-c-Met antibody to a patient in need thereof. In some embodiments, the activating antibody or a pharmaceutical composition comprising it is administered to a patient in need thereof an amount effective to increase c-Met activity. In a preferred embodiment, the activating antibody is able to restore normal c-Met activity. In another preferred embodiment, the activating antibody may be administered to a patient who is need of tissue regeneration. In another embodiment, the activating antibody may be administered to a patient to treat renal or tubulointerstitial fibrosis. In another embodiment, the activating anti-c-Met antibody may be administered to a patient to treat problems associated with transplant surgery, for example, to treat ischemia associated with kidney transplant rejection. In another embodiment, the activating antibody can be used to attenuate toxicity associated with cyclosporin treatment after transplant surgery. In another embodiment, the activating anti-c-Met antibody may be administered to treat myocardial infarction, cardiac ischemia due to reperfusion injury, restenosis after angioplasty, or vascular diseases such as arteriosclerosis obliterans. In another embodiment, the activating antibody may be administered to heal a wound, for example, refractory skin ulcers or to treat gastic ulcers. In another preferred embodiment, the activating antibody may be administered with one or more other factors that enhances a therapeutic procedure such as tissue regeneration or increase c-Met activity. Such factors include growth factors such as HGF, and/or analogues of HGF that activate c-Met. In a preferred embodiment, the antibody is selected from 13.3.2; 9.1.2; 8.70.2; 8.90.3, variants thereof or comprises a heavy chain, light chain or antigen-binding portion thereof.

Gene Therapy

The nucleic acid molecules of the present invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-c-Met antibody and expressing the nucleic acid molecule. In another embodiment, the gene therapy method comprises the steps' of administering an isolated nucleic acid molecule encoding the light chain or an antigen-binding portion thereof of an anti-c-Met antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-c-Met antibody of the invention and expressing the nucleic acid molecules. The gene therapy method may also comprise the step of administering another anti-cancer agent, such as taxol or adriamycin.

In order that this invention may be better understood, the following examples are set forth. These examples are for purposes of illustration only and are not to be construed as limiting the scope of the invention in any manner.

EXAMPLE I

Generation of Hybridomas Producing Anti-c-Met Antibody

Antibodies of the invention were prepared, selected, and assayed as follows:

Eight to ten week old XenoMouse™ mice were immunized intraperitoneally or in their hind footpads with either a c-Met extracellular domain fusion protein (10 μg/dose/mouse) (R&D Systems, Catalog #358MT) or with a NIH-3T3 transfected cell line that express human c-Met on its plasma membrane ($10\times10^6$ cells/dose/mouse). This dose was repeated five to seven times over a three to eight week period. Four days before fusion, the mice were given a final injection of the extracellular domain fusion protein of human c-Met in PBS. The spleen and lymph node lymphocytes from immunized mice were fused with the non-secretory myeloma P3-X63-Ag8.653 cell line, and these fused cells were subjected to HAT selection as previously described (Galfre and Milstein, *Methods Enzymol.* 73:3-46, 1981). A panel of hybridomas was recovered that all secrete c-Met specific human IgG2 antibodies. Four hybridomas were selected for further study and were designated 13.3.2; 9.1.2; 8.70.2 and 8.90.3. The hybridomas were deposited under terms in accordance with the Budapest Treaty with the American Type Culture Collection (ATCC), 10801 University Blvd., Manassas, Va. 20110-

2209 on Mar. 4, 2003. The hybridomas have been assigned the following accession numbers:

| | |
|---|---|
| Hybridoma 13.3.2 (LN 15883) | PTA-5026 |
| Hybridoma 9.1.2 (LN 15884) | PTA-5027 |
| Hybridoma 8.70.2 (LN 15885) | PTA-5028 |
| Hybridoma 6.90.3 (LN 15886) | PTA-5029 |

EXAMPLE II

Sequences of Anti-c-Met-Antibodies Prepared in Accordance with the Invention To analyze the structure of antibodies produced in accordance with the invention, nucleic acids were cloned that encode heavy and light chain fragments from hybridomas producing anti-c-Met monoclonal antibodies 13.3.2; 9.1.2; 8.70.2 and 8.90.3. Cloning and sequencing was accomplished as follows:

Poly(A)$^+$ mRNA was isolated using a Fast-Track kit (Invitrogen) from approximately $2\times10^5$ hybridoma cells derived from XenoMouse™ mice immunized with human c-Met. cDNA was synthesized from the mRNA by using random primers. The random primed cDNA was amplified using human $V_H$ or human Vκ family specific variable domain primers (Marks et al., "Oligonucleotide primers for polymerase chain reaction amplification of human immunoglobulin variable genes and design of family-specific oligonucleotide probes." *Eur. J. Immunol.* 21:985-991 (1991)) or a universal human $V_H$ primer [MG-30, 5'-CAGGTGCAGCTGGAGCAGTCIGG-3' (SEQ ID NO: 25)], in conjunction with primers specific for the human Cγ2 constant region, MG-40d [5'-GCTGAGGGAGTAGAGTCCTGAGGA-3' (SEQ ID NO: 26)] or a Cκ constant region [hκP2; as previously described in Green et al., 1994]. Nucleic acid molecules were obtained that encode human heavy and kappa light chain transcripts from the anti-c-Met producing hybridomas by direct sequencing of PCR products generated from poly(A$^+$) RNA using the primers described above. The PCR products were cloned into pCRII (Invitrogen) using a TA cloning kit (Invitrogen) and both strands were sequenced using Prism dye-terminator sequencing kits (Applied Biosystems Inc) and an ABI 377 sequencing machine (Applied Biosystems Inc). All sequences were analyzed by alignments to the "V BASE sequence directory" (Tomlinson et al., MRC Centre for Protein Engineering, Cambridge, UK) using MacVector and Geneworks software programs.

Monoclonal antibodies 13.3.2; 9.1.2; 8.70.2 and 8.90.3 were subjected to full length DNA cloning and sequencing. For such sequencing, RNA was isolated from approximately $2\times10^6$ hybridoma cells using QIAGEN RNeasy RNA isolation kit (QIAGEN). The mRNA was reverse transcribed using random hexamers (Roche Applied Science) and the SuperScript II RNase H-reverse transcriptase kit (Invitrogen). V Base was used to design forward amplification primers that included restriction sites, optimal Kozak sequence, the ATG start site and part of the signal sequence of the heavy chain. Table 2 lists the forward amplification primers used to obtain the antibody clones.

TABLE 2

| Clone | Forward Primer Heavy Chain | SEQ ID NO: |
|---|---|---|
| 13.3.2 | TATCTAAGCTTCTAGACGCCACCATGGACTGGACCTGG AGCATC | 31 |
| 9.1.2 | TATCTAAGCTTCTAGACGCCACCATGAAACACCTGTGG TTCTTC | 32 |
| 8.70.2 | TATCTAAGCTTCTAGACGCCACCATGAAGCACCTGTGG TTCTTC | 33 |
| 8.90.3 | TATCTAAGCTTCTAGACGCCACCATGGAGTTGGGGCTG TGCTGG | 34 |

The same method was used to design a primer to include the 3' coding sequences, the stop codon of the IgG2 constant region [5'-TTCTCTGATCAGAATTCC TATCATTTACCCGGAGACAGGGAGAG-3' (SEQ ID NO:27)] and restriction sites.

The same method was used to design a primer around the ATG start site of the kappa chain [5'-TATCTAAGCTTCTAGACGCCACCATGGACATGAGGGTCCCCGCT-3' (SEQ ID NO:28)] An optimal Kozak sequence (CCGCCACC) was added 5' to the ATG start site. This primer was used to PCR clone the light chains of antibody clones 13.3.2; 8.70.2 and 8.90.3. A second forward primer [5% TATCTAAGCTTCTAGACGCCACCATGGAAACCCCAGCGCAGCTTC-3' (SEQ ID NO:29)] was used to clone the light chain of clone 9.1.2. The same method also was used to design a primer around the stop codon of the kappa constant region [5'-TTCTTTGATCAGAATTCTCACTAACACTCTCCCCTGTTGAAGC-3' (SEQ ID NO:30)]. Platinum Pfx DNA Polymerase (Invitrogen) was used with the primer pairs to amplify the cDNAs. The PCR product was cloned into pCR-Blunt-II-TOPO (Invitrogen) to obtain the sequence of three to five clones for each kappa chain gene using standard techniques (e.g., primer walking) which employed dye-terminator sequencing kits and an ABI PRISM 3700 DNA Analyzer (Applied Biosystems Inc). The PCR product was cloned into a mammalian expression vector and clones were sequenced to confirm somatic mutations. For each clone, the sequence was verified on both strands in at least three reactions.

Gene Utilization Analysis

From the nucleic acid sequence and predicted amino acid sequence of the antibodies, the gene usage was identified for each antibody chain. Table 3 sets forth the gene utilization of selected hybridoma clones of antibodies in accordance with the invention:

TABLE 3

| Heavy and Light Chain Gene Utilization | | | | | | | |
|---|---|---|---|---|---|---|---|
| | Heavy Chain Germline | | | | Kappa Light Chain Germline | | |
| Clone | SEQ ID NO: | $V_H$ | $D_H$ | $J_H$ | SEQ ID NO: | Vκ | Jκ |
| 13.3.2 | 21 | 1-18 | D2-15 | $J_H$4b | 17 | L5Vκ1 | 4 |
| 9.1.2 | 22 | 4-31 | D2-2, D7-27 | $J_H$6b | 18 | A27Vκ3 | 2 |
| 8.70.2 | 23 | 4-39 | D2-2 | $J_H$4b | 19 | L5Vκ1 | 3 |
| 8.90.3 | 24 | 3-48 | D4-17 | $J_H$4b | 20 | L5Vκ1 | 1 |

Mutagenesis of specific residues of the heavy and light chains was carried out by designing primers and using the QuickChange Site Directed Mutagenesis Kit from Stratagene, according to the manufacturer's instructions. Mutations were confirmed by automated sequencing, and mutagenized inserts were subcloned into expression vectors. These expression vectors were transfected into NSO (ECACC #85110503) and HEK-293T cells (American Type Culture Collection) to express recombinant antibodies of the invention.

EXAMPLE III

Human Anti-c-Met Antibodies Block Binding of HGF to c-Met

In vitro assays to measure HGF binding to c-Met in the presence of anti-c-Met antibodies were conducted to determine if the anti-c-Met antibodies were capable of inhibiting HGF binding to c-Met and their degree of inhibition.

Wells of a 96-well tissue culture plate were coated with 100 μl of a 5 μg/ml solution comprising c-Met ECD/Fc (R&D Systems #358 MT) in phosphate buffered saline (PBS) overnight at room temperature. The plates were kept at 4° C. until needed for experiments. The wells were washed four times with Tris-buffered saline (pH=8.0) with 0.05% TWEEN-20 (TBS-T). Next, 200 μl/well of blocking buffer (3% bovine serum albumin (BSA) in TBS-T) was added for 60 minutes (min) at room temperature to block non-specific binding sites. The wells were washed 4 times with 300 μl/well TBS-T. Next, 100 μl of Dulbecco's Modified Eagle medium (DMEM) supplemented with 10% FBS containing anti-c-Met antibodies from hybridoma supernatants or purified antibodies in either PBS or 20 mM sodium acetate (pH=5.5), 140 mM NaCl at various concentrations (e.g., 10, 3, 1, 0.3, 0.1, 0.03, and 0.01 μg/ml, based on human IgG2 concentrations in the supernatants) was added to each well. Anti-c-Met antibody was not added to the control wells of the experiment. The samples were mixed for 4 hours (hrs) at room temperature. Next, 10 μl of 100 μg/ml HGF in serum-free DMEM was added to each well. The samples were mixed for 15 minutes at room temperature. The wells were washed 4 times with 300 μl/well/wash TBS-T. Next, 100 μl of a 1:2000 dilution of 100 μg/ml anti-HGF biotinylated antibody in blocking buffer was added. The solutions were incubated in the wells for 30 min at room temperature. The wells were washed 5 times with 300 μl/well TBS-T. Next, 100 μl/well of a 1.25 mg/ml streptavidin-horseradish peroxidase (HRP) at a 1:5000 dilution in blocking buffer was added. The samples were incubated for 30 min at room temperature. The wells were washed 5 times with TBS-T, about 300 μl/well/wash. Next, 100 μl/well of 3,3',5,5'-tetramethylbenzidine (TMB) peroxidase substrate (Kirkegaard & Perry Laboratories) was added and developed for 1-2 min at room temperature. To stop the reaction, 100 μl/well of TMB stop solution (Kirkegaard & Perry Laboratories, #50-85-04) was added. The samples were read at a wavelength of 450 nanometers (nm) on a 96-well plate reader and no background was subtracted.

These experiments demonstrate that the anti-c-Met antibodies inhibited the binding of HGF compared to control samples. Ligand Binding Assay (Table 4) shows the $IC_{50}$ for inhibition of ligand binding for antibodies 13.3.2; 9.1.2; 8.70.2 and 8.90.3.

TABLE 4

| | Antibody | | | | |
|---|---|---|---|---|---|
| Assay | 9.1.2 | 8.90.3 | 13.3.2 | 8.70.2 | 13.3.2L-A91T, H-E42K, S97T |
| Ligand Binding Assay [$IC_{50}$, μg/ml] | 0.093 | 0.110 | 0.090 | 0.115 | 0.127 |
| Cellular pTyr Assay [$IC_{50}$, μg/ml] | 0.033 | 0.086 | 0.033 | 0.143 | 0.032 |
| Cellular Met Levels [% loss at 1.0 μg/ml] | 46.9 | 17.5 | 23.8; 21.9 | 11.0 | 28.5 |
| Soft Agar Growth [$IC_{50}$, μg/ml] | 5.5 | 10.5 | 8.5 | 25 | ND |
| Tubular Morphogenesis Antagonism [% inhibition at 1 μg/ml] | 84 | 61 | ND | 25 | ND |
| Agonist Activity [maximum fold stimulation] | 6.5 | 2.3 | 2.7 | 2.5 | 2.5 |
| Tubular Morphogenesis Agonism [fold stimulation at 50 μg/ml] | 2.2 | 2.5 | ND | 8.2 | ND |

ND: Not Done

EXAMPLE IV

Inhibition of c-Met Phosphorylation by Anti-c-Met Antibodies

Anti-c-Met antibodies of the invention were used to measure inhibition of c-Met phosphorylation in cells after stimulation with HGF.

A549 cells were plated at a density of $1\times10^5$ cells per well in a total volume of 200 μl/well DMEM supplemented with 10% FBS in 96-well U-bottom tissue culture treated plates (Falcon, #3077). The plates were incubated at 37° C. in a 10% $CO_2$ atmosphere for 24 hrs. The media was gently aspirated from each well of the plates. Hybridoma supernatants to be tested were micro-centrifuged at 14,000 rpm for 5-10 min and cells were treated with 200 μl/well of the hybridoma supernatant or a dilution thereof, or purified antibodies in either PBS or 20 mM sodium acetate (pH=5.5), 140 mM NaCl. An irrelevant hybridoma supernatant was added to negative control wells. The cells were incubated at 37° C. for a short time period (e.g., 4 hours) or a longer time period (e.g., 24 hours) and then stimulated by the addition of 22 μl/well of a 2 μg/ml solution of HGF in serum-free DMEM media or Hank's buffer to give a final concentration 44 ng/well of HGF. The plates were incubated for 15 min at 37° C., then the media was gently aspirated from the wells of the plates. The cells were washed with cold PBS containing 1 mM $Na_3VO_4$ and the solution was gently aspirated from the plates. The cells were lysed with 50 μl lysis buffer (NP-40 Lysis buffer: 150 mM NaCl, 20 mM Tris-HCl pH=8.0, 1% NP-40, 10 mM EDTA, 10% glycerol), with freshly added 1 mM $Na_3VO_4$ and protease inhibitors (Complete tablet, Roche #1-873-580, used according to manufacturer's directions). The plates were shaken at room temperature for 10 minutes. The plates could then be stored at −20° C. until needed for ELISA.

An ELISA was used to determine c-Met phosphorylation levels. For ELISA plate preparation, Reacti-Bind Goat anti-rabbit coated plates were washed three times with wash buffer (TBS-T Sigma #T-9039). Next, 100 μl of c-Met polyclonal capture antibody (Santa Cruz, sc-10) in dilution buffer (10% SuperBlock from Pierce in TBS-T) (final concentration of 5 μg/ml) was added. The plates were incubated at room temperature with shaking for 2 hrs and then the plates were washed five times with TBS-T. Non-specific binding sites were blocked with 200 μl/well Superblock in TBS-T for 30 min at room temperature, while shaking. Just before use, the blocking solution from Reacti-Bind plates, was aspirated.

Cell lysates were prepared by adding 100 μl of dilution buffer containing 1 mM $Na_3VO_4$ and pipetting the lysates up and down and scraping the wells with the tips. Next, 100 μl/well of cell lysates diluted 1:3 were added to the Reacti-Bind plates and the plates were incubated at room temperature for 60 min while shaking. The plates were washed five times with TBS-T. Next, 100 μl/well of 1 μg/ml anti-phosphotyrosine antibody PY20-HRP (Transduction Labs, #P11625) in 3% bovine serum albumin-TBS-T containing 1 mM $Na_3VO_4$ was added. The plates were incubated for 2 hrs at room temperature while shaking. The plates were washed five times with TBS-T, with the washes removed by aspiration. The plates were blotted on paper towels to remove excess liquid. Next, 100 μl/well of TMB peroxidase substrate solution (Kirkegaard & Perry Laboratories, #50-76-04) was added and was developed while gently shaking for 4-5 min at room temperature. The reactions were stopped with 100 μl/well of TMB stop solution (Kirkegaard & Perry Laboratories, #50-85-04). The plates were read at a wavelength of 450 nm using a 96-well plate reader.

These experiments demonstrate that the anti-c-Met antibodies inhibited c-Met phosphorylation in cells stimulated with HGF compared to control cells. Cellular phospho-Tyrosine Assay (Table 4) shows the $IC_{50}$ for inhibition of cellular c-Met phosphorylation for antibodies 13.3.2; 9.1.2; 8.70.2 and 8.90.3 (Cellular pTyr Assay).

EXAMPLE V

Downregulation of c-Met with Anti-c-Met Antibodies in Cells Following Stimulation with HGF An assay was conducted to measure the inhibitory effect of anti-c-Met antibodies on c-Met expression levels in cells stimulated with HGF.

A549 cells lysates were prepared as described in Example IV. To determine c-Met levels, an ELISA was performed. The ELISA was performed essentially as described in Example IV with the following changes: instead of using an anti-phospho-tyrosine antibody, 100 μl UBI 05-237 antibody (ascites) (Anti-Met, ECD, clone DO24 Upstate Biotechnology, #21601) diluted 1:1000 in 3% BSA-TBS-T (with 1 mM $Na_3VO_4$) was added to each well. The incubation and wash steps were the same as in Example IV. Next, 100 μl/well of 0.8 mg/ml Goat Anti-Mouse IgG conjugated to (H+L)-HRP (Jackson ImmunoResearch Labs, #115-035-146 reconstituted in 750 μl water+750 μl glycerol), diluted 1:5000 in 3% BSA-TBS-T, was added. The plates were incubated for 60 min at room temperature while shaking. The wash and detection steps were the same as in Example IV.

These experiments demonstrate that c-Met levels are somewhat downregulated in cells after stimulation with HGF in the presence of the anti-c-Met antibodies, compared to control cells stimulated with HGF (Cellular Met Levels Downregulation, See Cellular Met Levels Table 4).

EXAMPLE VI

Anti-Proliferative Effects of Anti-c-Met Antibodies on Cells Grown in Soft Agar Soft agar growth assays were conducted to measure the anti-proliferative effects of anti-c-Met antibodies.

S114 tumor cells, NIH-3T3 cells engineered to express human HGF and human c-Met, were maintained in DMEM supplemented with 10% Calf Serum, 1,000 units/ml penicillin, 1,000 μg/ml streptomycin and 2 mM L-glutamine (growth medium). The cell cultures were trypsinized and washed in serum-free DMEM and adjusted the concentration to 50,000 cells/ml. The purified antibodies in either PBS or 20 mM sodium acetate (pH=5.5), 140 mM NaCl were prepared in 15 ml tubes at 10 times the various final concentrations used. Two agar layers of 0.5 (bottom) and 0.35% (top) diluted in cell growth media in 35 mm petri dishes were prepared. The bottom layer consisted of growth medium containing 0.5% agar in a total volume of 2 ml. The top layer consisted of growth media containing 0.35% agar, 5,000 S114 cells, and the antibody treatment at a final concentration of between 0.625-50 μg/ml in a 1 ml total volume, which was plated on top of the bottom agar layer. This solution was allowed to solidify at room temperature and incubated overnight at 37° C. in a 10% $CO_2$ atmosphere. 24 hrs later, 0.5 ml media was added with an appropriate antibody treatment to keep it moist and the dishes were incubated at 37° C. in a 10% $CO_2$ atmosphere for an additional 7-10 days. The media was removed and replaced with 0.5 ml of 1 mg/ml p-Iodonitrotetrazolium violet in PBS for 48 hrs. The number of colonies was counted with ROBOT (Ludel Electronics, Ltd.) using ETC3000 software (Engineering Technology Center).

These experiments demonstrate that the anti-c-Met antibodies inhibited proliferation of cells grown in soft agar. Soft Agar Growth (Table 4) shows the $IC_{50}$ for inhibition of proliferation of the cells in soft agar for antibodies 13.3.2; 9.1.2; 8.70.2 and 8.90.3.

EXAMPLE VII

Inhibition of c-Met-Dependent Cellular Morphological Changes in Cells with Anti-c-Met Antibodies HepG2 cells, which express c-Met, form tubular structures when grown in MATRIGEL™ (Becton-Dickinson), an extracellular matrix material containing components of the basement membrane, in the presence of HGF. Assays were conducted using HepG2 cells to measure tube formation (tubular morphogenesis) and its inhibition when cells are grown in the presence of HGF and treated with anti-c-Met antibodies.

Two ml of a media-MATRIGEL™ solution (MATRIGEL™ (Becton-Dickinson) diluted in Opti-MEM I (Invitrogen), 10% heat inactivated FBS, 2 mM L-glutamine, and 1× penicillin/streptomycin)) was plated in 35 millimeter (mm) tissue culture plates. After the media-MATRIGEL™ solution solidified, 1 ml medium supplemented with 10% serum and 40,000 HepG2 cells was added. Next, HGF (final concentration 50 ng/ml) and/or c-Met antibodies (final concentration of 1, 5 or 10 μg/ml) were added to the medium. The cells were grown for 4 days at 37° C. in a 10% $CO_2$ atmosphere. At the end of the 4 days, the top medium was removed and 0.5 ml of 1 mg/ml p-Iodonitrotetrazolium violet in PBS was added for 48 hrs. Pictures were taken of the stained 35 mm plates and analyzed using ImagePro (Media Cybernetics, Silver Spring, Md.).

These experiments demonstrate that the anti-c-Met antibodies inhibit c-Met-dependent tubular morphologenic changes when cells expressing c-Met are grown in the presence of HGF compared to control samples. Table 4 shows inhibition of tubular morphogenesis for antibodies 9.1.2; 8.70.2 and 8.90.3 at 1 μg/ml concentration.

EXAMPLE VIII

Determination of Affinity Constants ($K_D$) of Anti-c-Met Monoclonal Antibodies by BIACORE™

The binding affinity of purified antibodies was determined using surface plasmon resonance using the BIACORE™

3000 instrument (Pharmacia Biosensor AB, Uppsala, Sweden and Piscataway, N.J.), following the manufacturer's protocols.

Experiments were performed in a BIACORE™ 3000 instrument at 25° C. in Dulbecco's phosphate buffered saline containing 0.0005% Tween-20. Protein concentrations were obtained from sedimentation velocity experiments or by measuring the wavelength of the sample at 280 nm using theoretical extinction coefficients derived from amino acid sequences. For experiments measuring the binding of antibody to immobilized antigens, 220 RU (resonance units) of c-Met ECD-Fc (human or cynomologus) was immobilized on a B1 chip (BIACORE™) by standard direct amine coupling procedures. Antibody samples were prepared at 0.69 μM for 13.3.2; 8.70.2 and 8.90.3 and at 0.23 μM for 9.1.2. These samples were diluted 3-fold serially to 8.5 nM or 2.8 nM for roughly a 100-fold range in concentrations. For each concentration, samples were injected in duplicate at 5 μl/min flow for 4 min. The dissociation was monitored for 2000 seconds. The data were fit globally to a simple 1:1 binding model using BIACORE™ Biavel software. In addition, to determine the $k_{off}$ independent of any potential error in the active concentration or fitting model, the dissociation data were fit globally and independently from association data to a simple dissociation model. In all cases, this method was used to obtain $k_{off}$ and found that they compared well to data obtained from global fit of association and dissociation data.

Table 5 displays $K_D$ and $k_{off}$ data generated with antibodies 13.3.2; 8.70.2; 8.90.3 and 9.1.2.

TABLE 5

| | 13.3.2 | 9.1.2 | 8.70.2 | 8.90.3 | 13.3.2L-A91T, H-E42K, S97T |
|---|---|---|---|---|---|
| $K_D$ (M) (human) | $2.2 \times 10^{-10}$ | $8.2 \times 10^{-10}$ | $3.3 \times 10^{-10}$ | $5.3 \times 10^{-10}$ | $2.0 \times 10^{-10}$ |
| $k_{off}$ (1/s) (human) | $1.5 \times 10^{-4}$ | $6.8 \times 10^{-5}$ | $6.1 \times 10^{-5}$ | $1.5 \times 10^{-4}$ | $1.8 \times 10^{-4}$ |
| $K_D$ (M) (cynomologus) | $6.0 \times 10^{-10}$ | $1.1 \times 10^{-9}$ | $3.2 \times 10^{-10}$ | $1.22 \times 10^{-9}$ | $6.1 \times 10^{-10}$ |
| $k_{off}$ (1/s) (cynomologus) | $2.9 \times 10^{-4}$ | $9.8 \times 10^{-5}$ | $6.5 \times 10^{-5}$ | $2.5 \times 10^{-4}$ | $4.0 \times 10^{-4}$ |

EXAMPLE IX

Determination of Affinity Constants $K_D$ of Anti-c-Met Monoclonal Antibodies with Flow Cytometry The binding affinity of purified antibodies for c-Met expressed on the surface of human A549 lung carcinoma cells and cynomolgus kidney cells was determined by flow cytometry using the BD™ Biosciences LSR flow cytometer according to manufacturer's protocols.

Cells grown in culture were washed with PBS, briefly incubated in the presence of 0.25% trypsin-EDTA (Invitrogen) and collected. The collected cells were washed in PBS wash buffer containing 0.025% sodium azide and 2% heat inactivated serum, pelleted and $5 \times 10^5$ cells and resuspended in 500 μl of the same buffer. The time required to achieve equilibrium binding at room temperature for each antibody was determined independently to be between six and eight hours by incubating subsaturating concentrations of each antibody with cells. Next, half-maximal binding ($K_D$) of each antibody was determined from the geometric mean of fluorescence intensity for antibody concentrations ranging from 0.1 ng/ml to 3 μg/ml. Each antibody was incubated with detached cells for 6 to 8 hours at room temperature depending on the time required to reach equilibrium. Cells were washed, resuspended and incubated in 500 μl of a 1:500 dilution of biotinylated mouse anti-human IgG (Jackson Labs) in PBS wash buffer for 45 minutes on ice. Next, cells were washed, resuspended and incubated with 10 μg/ml streptavidin R-phycoerythrin conjugate (Caltag) in 200 μl PBS wash buffer for 15 min on ice protected from light. Cells were washed and signal was detected with a BD Biosciences LSR flow cytometer according to manufacturer's protocols.

These experiments demonstrate that each of the described anti-c-Met antibodies bind to human and cynomologus c-Met expressed on the cell surface with comparable affinities (see Table 6).

TABLE 6

| | 13.3.2 | 9.1.2 | 8.70.2 | 8.90.3 | 13.3.2L-A91T, H-E42K, S97T |
|---|---|---|---|---|---|
| $K_D$ (M) (human) | $3.93 \times 10^{-11}$ | $1.69 \times 10^{-10}$ | $4.07 \times 10^{-11}$ | $2.60 \times 10^{-11}$ | $5.60 \times 10^{-11}$ |
| $k_{off}$ (1/s) (human) | ND | ND | ND | ND | ND |
| $K_D$ (M) (cynomologus) | $4.86 \times 10^{-11}$ | $1.68 \times 10^{-10}$ | $5.53 \times 10^{-11}$ | $3.93 \times 10^{-10}$ | $7.33 \times 10^{-11}$ |
| $k_{off}$ (1/s) (cynomologus) | ND | ND | ND | ND | ND |

EXAMPLE X

Inhibition of Tumor Growth In Vivo with Anti-c-Met Antibodies

In vivo assays were conducted to measure tumor growth inhibition of solid tumors after treatment with anti-c-Met antibodies.

S114, U87 (human glioblastoma cells), GTL-16 (human gastric tumor cells) and A549 (human lung carcinoma epithelial cells) were maintained in DMEM (Invitrogen) supplemented with 10% heat inactivated FBS (Invitrogen), 2 mM L-Glutamine (Invitrogen), and 1% [volume/volume] penicillin (1,000 units/ml)-streptomycin (1,000 μg/ml)(Invitrogen) in a 37° C./10% $CO_2$ tissue culture incubator. To inoculate athymic (nu/nu) mice with tumor cells, 0.25% trypsin in 1 mM EDTA was used to remove tumor cells from their tissue culture flasks. The cells were counted and diluted with Hank's Buffered Saline Solution. Using $1.0\text{-}5.0\times10^6$ tumor cells in a final volume of 0.2 ml Hank's Buffered Saline Solution, the tumor cells were inoculated subcutaneously into each animal subject. Once tumors had reached 100-200 $mm^3$ in size (day 5 post-inoculation for S114 and U87 tumors, about 15-20 days for A549 tumors and about 6 days for GTL-16 tumors), 200 μl of antibody solution was injected. The antibodies were stored in 20 mM sodium acetate, pH 5.5, 140 mM sodium chloride and were diluted with sterile phosphate buffered saline to the desired antibody concentration. Either 100 μg or 200 μg antibody were injected into the intraperitoneal (IP) cavity of each experimental animal subject. Vehicle solutions were administered to control animals. Tumor sizes were measured in the mice using calipers every two to three days following IP delivery of the antibody solution until the termination of the experiments.

These experiments demonstrate that all of the anti-c-Met antibodies inhibit the growth of solid tumors in vivo compared to control animals. Further, by using various concentrations of antibodies, the percent of tumor growth inhibition by antibodies 13.3.2; 9.1.2; 8.70.2, 8.90.3 and 13.3.2L-A91T, H-E42K, S97T (See Table 7) was determined. In the experiment summarized in Table 7, all antibodies were administered at a single intraperitoneal dose, except for the 41-day experiment with A549 tumor-bearing animals, which involved four doses of antibody and the 21 day experiment with GTL-16 tumor-bearing animals, which involved two doses of antibody. Doses used were 200 μg for the S114 tumors, 100 μg for the U87 tumors, 200 μg for the A549 tumors and 200 μg for the GTL-16 tumors. The value in parentheses corresponds to a 200 μg dose of 13.3.2 in the U87 model. ND, not done in the experiment shown.

TABLE 7

| | Tumor Type: | | | |
|---|---|---|---|---|
| | % Inhibition (Tumor Volume) | | | |
| Antibody: | S114 (Day 12) | U87 (Day 17) | A549 (Day 41) | GTL-16 (Day 21) |
| 9.1.2 | 77.2 | 61.4 | 40.6 | ND |
| 13.3.2 | 99.1 | 74.2 (83.1) | 45.9 | ND |
| 8.70.2 | 83.2 | ND | ND | ND |
| 8.90.3 | 94.8 | 49.0 | ND | ND |
| 13.3.2L-A91T, H-E42K, S97T | ND | ND | ND | 55.7 |

EXAMPLE XI

Agonist Activity with Anti-c-Met Antibodies

Activation of c-Met by Anti-c-Met Antibodies in the Absence of HGF Stimulation

The activation of c-Met in cells incubated with anti-c-Met antibodies in the absence of HGF was measured to determine the agonist activity of the c-Met antibodies of the invention. An ELISA was used to determine whether c-Met was activated in the cells by measuring phosphorylation of c-Met. Between 0.01-10 μg/ml of antibody was added to A549 cells plated as described in Example IV, except the cells were not stimulated with HGF. The A549 cell lysates were prepared as described in Example IV. An ELISA was conducted as described in Example IV.

These experiments demonstrate that three of the antibodies tested show a weak, approximately 2-3 fold activation of c-Met, in the absence of HGF compared to cells not incubated with anti-c-Met antibody or HGF (See Table 4); however, antibody 9.1.2 showed a higher fold activation.

c-Met-Dependent Cellular Morphological Changes in Cells Treated with Anti-c-Met Antibodies in the Absence of HGF Tubular morphogenesis assays were conducted to measure anti-c-Met antibody agonist activity. The assays were conducted as described in Example VII, except that the cells are grown in the absence of HGF and treated with anti-c-Met antibodies (1, 10 and 50 μg/ml). The amount of tubular morphogenesis was determined as described in Example VII. The assay shows that three anti-c-Met antibodies tested have weak to moderate agonist activity. Table 4 shows the amount of agonist activity as measured by tubular morphogenesis for antibodies 9.1.2; 8.70.2 and 8.90.3

EXAMPLE XII

Inhibition of c-Met Phosphorylation and Induction of c-Met Degradation by Anti-c-Met Antibodies in vivo We determined the effects of the anti-c-Met antibodies on the phosphorylation state and protein levels of c-Met in vivo. Human tumor cells were introduced into athymic mice resulting in the formation of xenograft tumors according to the methods of V. A. Pollack et al., ("Inhibition of epidermal growth factor receptor-associated tyrosine phosphorylation in human carcinomas with CP-358,774: Dynamics of receptor inhibition in situ and antitumor effects in athymic mice," J. Pharmacol. Exp. Ther. 291:739-748 (1999)).

U87 human glioblastoma cells ($5\times10^6$) were injected subcutaneously into 3-4 week-old athymic (nu/nu) mice, and subsequently an anti-c-Met antibody of the present invention was injected intraperitoneally into mice harboring established tumors (approximately 300 $mm^3$). Tumors were extracted at various times (1, 3, 6, 12, 24, 48, 72, 96, 168, and 216 hours) after antibody injection and homogenates were produced (1 ml lysis buffer/100 mg tumor weight) in order to assess c-Met phosphorylation and protein levels. Lysates containing two milligrams of protein were immunoprecipitated with 25 μl of sc-10 agarose beads (Santa Cruz) specific for c-Met for 2 hours at 4° C. The beads were washed and bound protein was eluted by boiling in Laemmli sample buffer for 5 min and separated by SDS-PAGE using 4-12% gradient Novex™ gels. Immunocaptured proteins were then electroblotted to 0.45 μM PVDF membranes (Invitrogen). The membranes were blocked in 3% BSA in PBS-T (0.5% Tween 20) for 1 hour at room temperature and probed with the anti-phosphotyrosine-specific antibody PY100 (Cell Signaling Technology) followed by anti-mouse IgG-HRP to detect phosphoMet or sc-10-HRP (Invitrogen) to detect total Met protein. Signal was developed with ECL reagent (Amersham Biosciences) and detected by exposure of radiographic film (Kodak).

Figure 5:
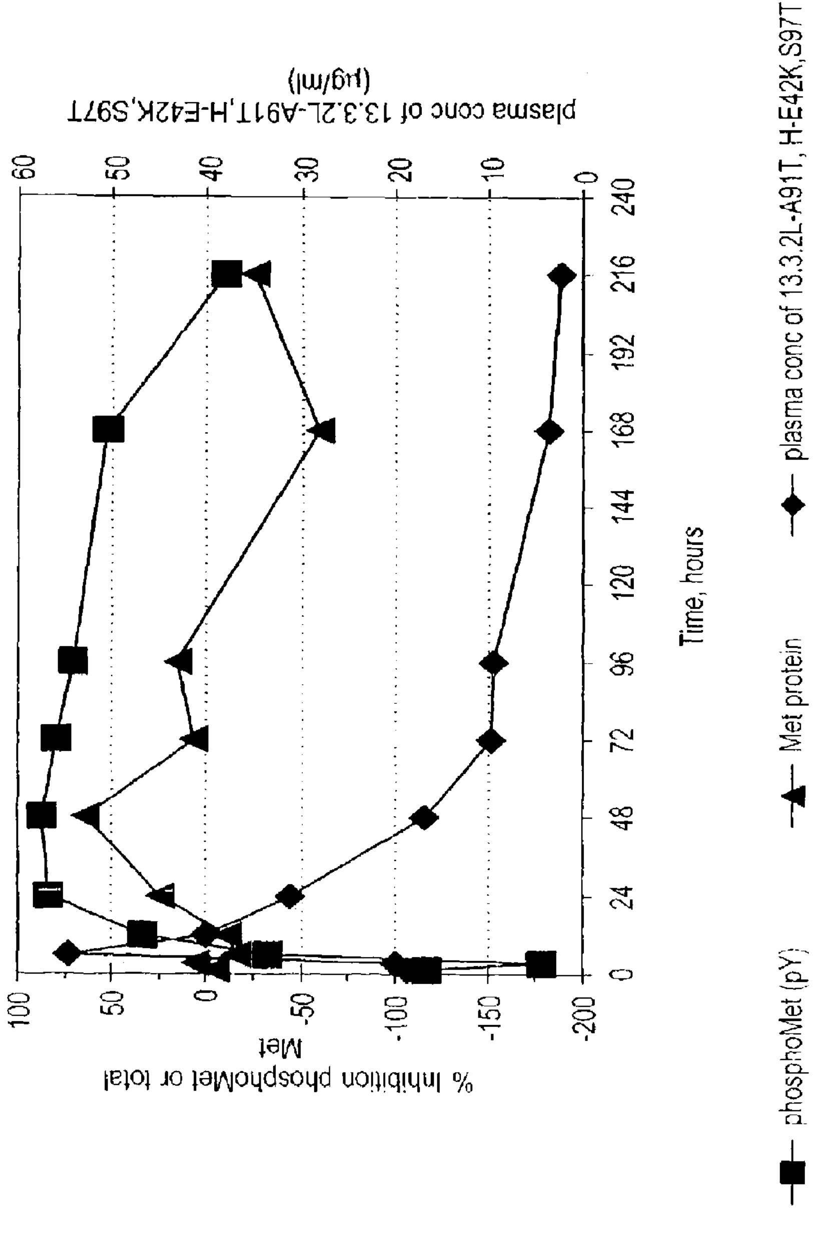
FIG. 5 shows the relationship between anti-c-Met antibody 13.3.2L-A91T, H-E42K, S97T serum levels and inhibition of c-Met activity.

FIG. 5 shows the serum 13.3.2L-A91T, H-E42K, S97T antibody levels, phospho c-Met levels and total c-Met protein levels over time. The experiment demonstrates that the decreased phospho c-Met and total c-Met protein levels are related to the antibody and that the degree of c-Met inhibition is dose proportional to the serum concentration of the antibody.

EXAMPLE XIII

Epitope Mapping Studies

Competition experiments using an ELISA format were performed to define epitope classes recognized by the antibodies of the invention.

Wells of a 96-well plate were coated with 50 μl/well of a 0.5 μg/ml stock of human Met ECD-Fc in 0.1 M $NaHCO_3$ buffer, pH 9.6 overnight at 4° C. or for 2 hours at 37° C. The plates were washed in PBS, 0.05% Tween-20 (PBS-T) and blocked with 200 μl/well of blocking buffer (PBS containing 0.5% BSA, 0.1% Tween-20, and 0.01% thimerosal) at room temperature for one hour. After washing, 100 μl of antibody at various concentrations (15, 5, 1.7, and 0.6 μg/ml) in blocking buffer was added and the plates were incubated at room temperature for 1 hour. Next, 100 μl of a 83 μg/ml solution of biotinylated antibody (~4 biotins/molecule) in blocking buffer was added and the plates were incubated at room temperature for 1 hour. After washing, streptavidin-HRP was added and the plates were incubated at room temperature for 15 minutes. Binding was indicated by color development following the addition of 100 μl/well undilulted TMB peroxidase solution (BioFX Labs). Color development was terminated with 100 μl/well undiluted Stop solution (BioFX Labs) and quantitated by measurement at $OD_{450nm}$.

These experiments demonstrate that monoclonal antibodies 13.3.2, 13.3.2L-A91T, H-E42K, S97T, 8.70.2, and 8.90.3 bind to a common epitope (bin 1) on the extracellular domain of c-Met and that monoclonal antibody 9.1.2 binds to a distinct epitope (bin 2).

All publications and patent applications cited in this specification are incorporated herein by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated monoclonal antibody or an antigen-binding portion thereof that cross-competes for binding to human c-Met and binds the same epitope as, an antibody selected from the group consisting of 13.3.2 (ATCC accession PTA-5026); 9.1.2 (ATCC accession PTA-5027); 8.70.2 (ATCC accession PTA-5028); and 8.90.3 (ATCC accession PTA-5029).

2. The antibody or antigen-binding portion thereof according to claim 1, wherein competition is determined by ELISA.

3. The antibody or antigen-binding portion thereof according to claim 2 that binds human c-MET with a $K_D$ of 0.5 nM or less.

4. The antibody or antigen binding portion thereof according to claim 2 that inhibits human HGF binding to human c-MET with an $IC_{50}$ of less than 0.20 μg/ml.

5. The antibody or antigen-binding portion thereof according to claim 2 that binds human c-MET with a $K_D$ of 0.5 nM or less as determined by surface plasmon resonance and inhibits human HGF binding to human c-MET with an $IC_{50}$ of less than 0.20 μg/ml.

6. The antibody or antigen-binding portion thereof according to claim 2 that is a Fab, a Fab', a F(ab')2, a Fv or a scFv.

7. The antibody or antigen-binding portion thereof according to claim 5 that is a Fab, a Fab', a F(ab')2, a Fv or a scFv.

8. The antibody or antigen-binding portion thereof according to claim 2 that is a human or humanized antibody or antigen-binding portion thereof.

9. The antibody or antigen-binding portion thereof according to claim 5 that is a human or humanized antibody or antigen-binding portion thereof.

10. The antibody or antigen-binding portion thereof according to claim 7 that is a human or humanized antibody or antigen-binding portion thereof.

11. A pharmaceutical composition comprising the antibody or antigen-binding portion thereof according to claim 2 and a pharmaceutically acceptable carrier.

12. A pharmaceutical composition comprising the antibody or antigen-binding portion thereof according to claim 5 and a pharmaceutically acceptable carrier.

13. A pharmaceutical composition comprising the antibody or antigen-binding portion thereof according to claim 7 and a pharmaceutically acceptable carrier.

14. The antibody or antigen-binding portion thereof according to claim 1 that cross-competes and binds the same epitope as antibody 13.3.2 (ATCC accession PTA-5026).

15. The antibody or antigen-binding portion thereof according to claim 1 that cross-competes and binds the same epitope as antibody 9.1.2 (ATCC accession PTA-5027).

16. The antibody or antigen-binding portion thereof according to claim 1 that cross-competes and binds the same epitope as antibody 8.70.2 (ATCC accession PTA-5028).

17. The antibody or antigen-binding portion thereof according to claim 1 that cross-competes and binds the same epitope as antibody 8.90.3 (ATCC accession PTA-5029).

18. The antibody or antigen-binding portion thereof according to claim 5 that cross-competes and binds the same epitope as antibody 13.3.2 (ATCC accession PTA-5026).

19. The antibody or antigen-binding portion thereof according to claim 5 that cross-competes and binds the same epitope as antibody 9.1.2 (ATCC accession PTA-5027).

20. The antibody or antigen-binding portion thereof according to claim 5 that cross-competes and binds the same epitope as antibody 8.70.2 (ATCC accession PTA-5028).

21. The antibody or antigen-binding portion thereof according to claim 5 that cross-competes and binds the same epitope as antibody 8.90.3 (ATCC accession PTA-5029).

* * * * *